United States Patent
Goldberg

(10) Patent No.: US 8,080,651 B2
(45) Date of Patent: Dec. 20, 2011

(54) JUVENILE HEMOCHROMATOSIS GENE (HFE2A), EXPRESSION PRODUCTS AND USES THEREOF

(75) Inventor: Yigal P. Goldberg, Vancouver (CA)

(73) Assignee: Xenon Pharmaceuticals Inc., Burnaby, B.C. (CA)

( * ) Notice: Subject to any disclaimer, the term of this patent is extended or adjusted under 35 U.S.C. 154(b) by 6 days.

(21) Appl. No.: 12/456,667

(22) Filed: Jun. 19, 2009

(65) Prior Publication Data

US 2010/0041139 A1    Feb. 18, 2010

Related U.S. Application Data

(63) Continuation of application No. 10/552,158, filed as application No. PCT/CA2004/00522 on Apr. 8, 2004, now abandoned.

(60) Provisional application No. 60/462,867, filed on Apr. 15, 2003, provisional application No. 60/488,607, filed on Jul. 18, 2003, provisional application No. 60/498,458, filed on Aug. 28, 2003.

(51) Int. Cl.
*C07H 21/04* (2006.01)
*A61K 31/70* (2006.01)

(52) U.S. Cl. ........................ 536/24.5; 514/44

(58) Field of Classification Search .............. None
See application file for complete search history.

(56) References Cited

U.S. PATENT DOCUMENTS

| | | | |
|---|---|---|---|
| 6,943,241 B2 | 9/2005 | Isogai et al. | |
| 7,250,496 B2 * | 7/2007 | Bentwich | 536/23.1 |
| 7,511,018 B2 | 3/2009 | Goldberg et al. | |
| 7,534,764 B2 | 5/2009 | Ganz et al. | |
| 7,696,155 B2 | 4/2010 | Woolf et al. | |
| 7,696,156 B2 | 4/2010 | Woolf et al. | |
| 7,745,407 B2 | 6/2010 | Ganz et al. | |
| 7,893,206 B2 | 2/2011 | Goldberg et al. | |
| 2004/0102376 A1 | 5/2004 | Mueller | |
| 2007/0004618 A1 | 1/2007 | Ganz et al. | |

FOREIGN PATENT DOCUMENTS

| | | |
|---|---|---|
| WO | WO 96/13518 | 5/1996 |
| WO | WO 9640162 A1 * | 12/1996 |
| WO | WO 00/73801 | 12/2000 |
| WO | WO 01/74901 | 10/2001 |
| WO | WO 02/051438 | 7/2002 |
| WO | WO 02/074961 | 9/2002 |
| WO | WO 2004/092405 | 10/2004 |

OTHER PUBLICATIONS

Afanassiev et al., Mutation Research, vol. 464, pp. 297-308 (2000).
Collins et al., PNAS USA, vol. 99(26), pp. 16899-16903 (2002).
Goldberg et al., Amer. J. Human Gen., vol. 73, p. 205 (2003) (Abstract).
Gonzalez et al., Curr. Opin. Biotechnology, vol. 9, pp. 624-631 (1998).
Hertzberg et al., Curr. Op. Chem. Biol., vol. 4, pp. 445-451 (2000).
Koller et al., Trends in Pharmacol. Sci., vol. 21, pp. 142-148 (2000).
Leong and Lonnerdal, J. Nutrition, vol. 134, pp. 1-4 (2004).
Lin et al., Blood, vol. 106, pp. 2884-2889 (2005).
Mattheakis et al., Chem. & Biol., Curr. Biol., vol. 6, pp. 835-844 (1999).
Mueller, B.K., Ann. Rev. Neurosci., vol. 22, pp. 351-388 (1999).
Muller et al., Current Biology, vol. 6, pp. 1497-1502 (1996).
Pender et al., J. Med. Chem., vol. 44, pp. 36-45 (2001).
Taupin et al., J. Immun. Methods, vol. 256, pp. 77-87 (2001).
Ganz, T., J. Am. Soc. Nephrol., vol. 18, pp. 394-400 (2007).

* cited by examiner

*Primary Examiner* — Tracy Vivlemore
(74) *Attorney, Agent, or Firm* — Carella, Byrne, et al.; Elliot M. Olstein; Alan J. Grant

(57) ABSTRACT

Polynucleotide and polypeptide sequences for HFE2A, as well as mutations associated with juvenile hemochromatosis, and methods of utilizing these for the screening and identification of agents for the treatment of diseases of iron metabolism, including small organic compounds, are disclosed along with methods of treating and/or ameliorating diseases of iron metabolism, especially in human patients are disclosed. Diagnostic compounds, kits and methods using HFE2A are also described.

35 Claims, 19 Drawing Sheets

```
                  *           180            *             200           *
LOC148738  : K.CIPI.STH----IHIHTFICIWPLTNILVQATSEPMILSS :  46
gnl|CDD|192 : SVSED.YTITLIKITIPNITYVLAITSIPSISVIL.IVI--GIG :  48

220              *           240            *           260
LOC148738  : NAT.ISK.I.IEIMI.QKVYQIVI---IIIAIGSI       :  87
gnl|CDD|192 : DAICISVIBLNDILIEIKIIIIVAIQIISLIYKTSDGSIR    :  93
```

Figure 7D

```
                    ↓        *
Human      :  PGDPHVRSF------ :  9
Chicken_RGM :  PGDPHLRTF------ :  9
```

Figure 7E

```
1    ATGGGGGAGCCAGGCCAGTCCCCTAGTCCCAGGTCCTCCCATGGCAGTCCCCCAACTCTA
1    -M--G--E--P--G--Q--S--P--S--P--R--S--S--H--G--S--P--P--T--L-
                       +     +     +  +           +        +

61   AGCACTCTCACTCTCCTGCTGCTCCTCTGTGGACATGCTCATTCTCAATGCAAGATCCTC
21   -S--T--L--T--L--L--L--L--C--G--H--A--H--S--Q--C--K--I--L-
                                                ▲

121  CGCTGCAATGCTGAGTACGTATCGTCCACTCTGAGCCTTAGAGGTGGGGGTTCATCAGGA
41   -R--C--N--A--E--Y--V--S--S--T--L--S--L--R--G--G--G--S--G-

181  GCACTTCGAGGAGGAGGAGGAGGAGGCCGGGGTGGAGGGGTGGGCTCTGGCGGCCTCTGT
61   -A--L--R--G--G--G--G--G--G--R--G--G--G--V--G--S--G--G--L--C-

241  CGAGCCCTCCGCTCCTATGCGCTCTGCACTCGGCGCACCGCCCGCACCTGCCGCGGGGAC
81   -R--A--L--R--S--Y--A--L--C--T--R--R--T--A--R--T--C--R--G--D-
                                                          ● ● ●

301  CTCGCCTTCCATTCGGCGGTACATGGCATCGAAGACCTGATGATCCAGCACAACTGCTCC
101  -L--A--F--H--S--A--V--H--G--I--E--D--L--M--I--Q--H--N--C--S-
                                                          ♦ ♦ ♦

361  CGCCAGGGCCCTACAGCCCCTCCCCCGCCCCGGGGCCCCGCCCTTCCAGGCGCGGGCTCC
121  -R--Q--G--P--T--A--P--P--P--R--G--P--A--L--P--G--A--G--S-
                    +

421  GGCCTCCCTGCCCCGGACCCTTGTGACTATGAAGGCCGGTTTTCCCGGCTGCATGGTCGT
141  -G--L--P--A--P--D--P--C--D--Y--E--G--R--F--S--R--L--H--G--R-

481  CCCCCGGGGTTCTTGCATTGCGCTTCCTTCGGGGACCCCCATGTGCGCAGCTTCCACCAT
161  -P--P--G--F--L--H--C--A--S--F--G--D--P--H--V--R--S--F--H--H-
                                            ↑
```

Figure 8A – 1

```
541  CACTTTCACACATGCCGTGTCCAAGGAGCTTGGCCTCTACTGGATAATGACTTCCTCTTT
181  -H--F--H--T--C--R--V--Q--G--A--W--P--L--L--D--N--D--F--L--F-

601  GTCCAAGCCACCAGCTCCCCCATGGCGTTGGGGGCCAACGCTACCGCCACCCGGAAGCTC
201  -V--Q--A--T--S--S--P--M--A--L--G--A--N--A--T--A--T--R--K--L-
                                        ♦  ♦  ♦
661  ACCATCATATTTAAGAACATGCAGGAATGCATTGATCAGAAGGTGTATCAGGCTGAGGTG
221  -T--I--I--F--K--N--M--Q--E--C--I--D--Q--K--V--Y--Q--A--E--V-

721  GATAATCTTCCTGTAGCCTTTGAAGATGGTTCTATCAATGGAGGTGACCGACCTGGGGGA
241  -D--N--L--P--V--A--F--E--D--G--S--I--N--G--G--D--R--P--G--G-

781  TCCAGTTTGTCGATTCAAACTGCTAACCCTGGGAACCATGTGGAGATCCAAGCTGCCTAC
261  -S--S--L--S--I--Q--T--A--N--P--G--N--H--V--E--I--Q--A--A--Y-
                          ✝
841  ATTGGCACAACTATAATCATTCGGCAGACAGCTGGGCAGCTCTCCTTCTCCATCAAGGTA
281  -I--G--T--T--I--I--R--Q--T--A--G--Q--L--S--F--S--I--K--V-

901  GCAGAGGATGTGGCCATGGCCTTCTCAGCTGAACAGGACCTGCAGCTCTGTGTTGGGGGG
301  -A--E--D--V--A--M--A--F--S--A--E--Q--D--L--Q--L--C--V--G--G-

961  TGCCCTCCAAGTCAGCGACTCTCTCGATCAGAGCGCAATCGTCGGGGAGCTATAACCATT
321  -C--P--P--S--Q--R--L--S--R--S--E--R--N--R--R--G--A--I--T--I-
                                                  ⬆⬆
1021 GATACTGCCAGACGGCTGTGCAAGGAAGGGCTTCCAGTGGAAGATGCTTACTTCCATTCC
341  -D--T--A--R--R--L--C--K--E--G--L--P--V--E--D--A--Y--F--H--S-
```

Figure 8A - 2

```
1081  TGTGTCTTTGATGTTTTAATTTCTGGTGATCCCAACTTTACCGTGGCAGCTCAGGCAGCA
361   -C--V--F--D--V--L--I--S--G--D--P--N--F--T--V--A--A--Q--A--A-
                                   ♦   ♦   ♦

1141  CTGGAGGATGCCCGAGCCTTCCTGCCAGACTTAGAGAAGCTGCATCTCTTCCCCTCAGAT
381   -L--E--D--A--R--A--F--L--P--D--L--E--K--L--H--L--F--P--S--D-
                                                                ■

1201  GCTGGGGTTCCTCTTTCCTCAGCAACCCTCTTAGCTCCACTCCTTTCTGGGCTCTTTGTT
401   -A--G--V--P--L--S--S--A--T--L--L--A--P--L--L--S--G--L--F--V-

1261  CTGTGGCTTTGCATTCAGTAAGGGGACCATCAGTCCCATTACTAGTTTGGAAATGATTTG
421   -L--W--L--C--I--Q--*..........................................
```

Figure 8B

Open circle/square = Unknown (no data)
Crossed circle/square = Unaffected
Filled circle/square = Affected
Grey circle/square = Unknown (ambiguous)
Slash circle/square = Deceased
Figure 9
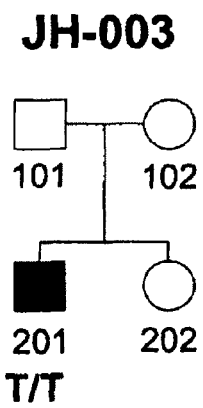
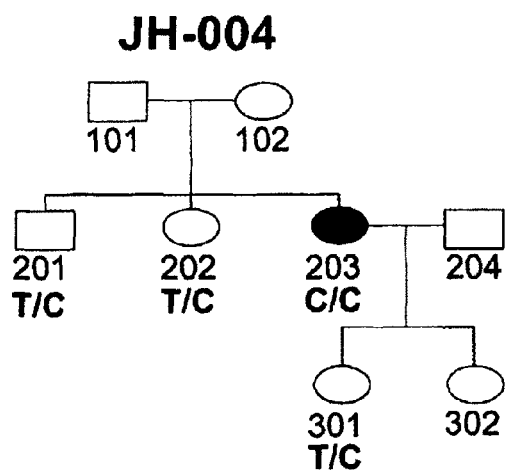
Figure 9A    Figure 9B

SEQUENCE LISTING

```
<160> NUMBER OF SEQ ID NOS: 71

<210> SEQ ID NO 1
<211> LENGTH: 149
<212> TYPE: DNA
<213> ORGANISM: Homo sapiens

<400> SEQUENCE: 1
cttctctggt tccctgacct cagtgagaca gcagccggcc tggggacctg ggggagacac    60
```

-continued

```
ggaggacccc ctggctggag ctgacccaca gagtagggaa tcatggctgg agaattggat      120
agcagagtaa tgtttgacct ctggaaaca                                        149
```

<210> SEQ ID NO 2
<211> LENGTH: 204
<212> TYPE: DNA
<213> ORGANISM: Homo sapiens

<400> SEQUENCE: 2

```
ccaaatttct tttttcagtc acttacaggg cttccggtca aaattcacta ggtaggaggg       60
tcatcagctg ggaagaaccg cgcctggga aacctggctg gataggtatg ggggagccag       120
gccagtcccc tagtcccagg tcctcccatg gcagtccccc aactctaagc actctcactc      180
tcctgctgct cctctgtgga catg                                             204
```

<210> SEQ ID NO 3
<211> LENGTH: 37
<212> TYPE: DNA
<213> ORGANISM: Homo sapiens

<400> SEQUENCE: 3

```
ctcattctca atgcaagatc ctccgctgca atgctga                                37
```

<210> SEQ ID NO 4
<211> LENGTH: 560
<212> TYPE: DNA
<213> ORGANISM: Homo sapiens

<400> SEQUENCE: 4

```
ctcattctca atgcaagatc ctccgctgca atgctgagta cgtatcgtcc actctgagcc       60
ttagaggtgg gggttcatca ggagcacttc gaggaggagg aggaggaggc cggggtggag      120
gggtgggctc tggcggcctc tgtcgagccc tccgctccta tgcgctctgc actcggcgca     180
ccgcccgcac ctgccgcggg gacctcgcct tccattcggc ggtacatggc atcgaagacc     240
tgatgatcca gcacaactgc tcccgccagg gccctacagc ccctcccccg ccccggggcc     300
ccgcccttcc aggcgcgggc tccggcctcc ctgccccgga cccttgtgac tatgaaggcc     360
ggttttcccg gctgcatggt cgtccccgg ggttcttgca ttgcgcttcc ttcggggacc      420
cccatgtgcg cagcttccac catcactttc acacatgccg tgtccaagga gcttggcctc     480
tactggataa tgacttcctc tttgtccaag ccaccagctc ccccatggcg ttgggggcca     540
acgctaccgc cacccggaag                                                 560
```

<210> SEQ ID NO 5
<211> LENGTH: 1230
<212> TYPE: DNA
<213> ORGANISM: Homo sapiens

<400> SEQUENCE: 5

```
ctcaccatca tatttaagaa catgcaggaa tgcattgatc agaaggtgta tcaggctgag       60
gtggataatc ttcctgtagc ctttgaagat ggttctatca atggaggtga ccgacctggg      120
ggatccagtt tgtcgattca aactgctaac cctgggaacc atgtggagat ccaagctgcc     180
tacattggca caactataat cattcggcag acagctgggc agctctcctt ctccatcaag     240
gtagcagagg atgtggccat ggccttctca gctgaacagg acctgcagct ctgtgttggg     300
gggtgccctc caagtcagcg actctctcga tcagagcgca atcgtcgggg agctataacc     360
attgatactg ccagacggct gtgcaaggaa gggcttccag tggaagatgc ttacttccat     420
```

-continued

```
tcctgtgtct ttgatgtttt aatttctggt gatcccaact ttaccgtggc agctcaggca      480
gcactggagg atgcccgagc cttcctgcca gacttagaga agctgcatct cttccctca       540 gatgctgggg ttcctctttc ctcagcaacc ctcttagctc cactcctttc tgggctcttt     600
gttctgtggc tttgcattca gtaagggac catcagtccc attactagtt tggaaatgat      660
ttggagatac agattggcat agaagaatgt aaagaatcat aaaggaagc agggcctagg      720 agacacgtga acaatgaca ttatccagag tcagatgagg ctgcagtcca gggttgaaat     780
tatcacagaa taaggattct gggcaaggtt actgcattcc ggatctctgt ggggctcttc    840
accaattttt ccagcctcat ttatagtaaa caaattgttc taatccattt actgcagatt    900
tcacccttat aagtttagag gtcatgaagg ttttaatgat cagtaaagat ttaagggttg     960 agattttta  gaggcaagag ctgaaagcag aagacatgat cattagccat aagaaactca    1020
aaggaggaag acataattag ggaaagaagt ctatttgatg aatatgtgtg tgtaaggtat    1080
gttctgcttt cttgattcaa aaatgaagca ggcattgtct agctcttagg tgaagggagt   1140
ctctgctttt gaagaatggc acaggtagga cagaagtatc atccctaccc cctaactaat   1200
ctgttattaa agctacaaat tcttcacacc                                    1230
```

<210> SEQ ID NO 6
<211> LENGTH: 1379
<212> TYPE: DNA
<213> ORGANISM: Homo sapiens

<400> SEQUENCE: 6

```
cttctctggt tccctgacct cagtgagaca gcagccggcc tggggacctg ggggagacac     60
ggaggacccc ctggctggag ctgacccaca gagtagggaa tcatggctgg agaattggat   120
agcagagtaa tgtttgacct ctggaaacac tcaccatcat atttaagaac atgcaggaat   180
gcattgatca gaaggtgtat caggctgagg tggataatct tcctgtagcc tttgaagatg   240
gttctatcaa tggaggtgac cgacctgggg gatccagttt gtcgattcaa actgctaacc   300
ctgggaacca tgtggagatc caagctgcct acattggcac aactataatc attcggcaga  360
cagctgggca gctctccttc tccatcaagg tagcagagga tgtggccatg gccttctcag  420
ctgaacagga cctgcagctc tgtgttgggg ggtgccctcc aagtcagcga ctctctcgat    480
cagagcgcaa tcgtcgggga gctataacca ttgatactgc cagacggctg tgcaaggaag  540
ggcttccagt ggaagatgct tacttccatt cctgtgtctt tgatgtttta atttctggtg    600
atcccaactt taccgtggca gctcaggcag cactggagga tgcccgagcc ttcctgccag   660
acttagagaa gctgcatctc ttcccctcag atgctggggt tcctctttcc tcagcaaccc   720
tcttagctcc actcctttct gggctctttg ttctgtggct ttgcattcag taagggacc    780 atcagtccca ttactagttt ggaaatgatt tggagataca gattggcata agaagaatgta  840 aagaatcatt aaaggaagca gggcctagga gacacgtgaa acaatgacat tatccagagt   900
cagatgaggc tgcagtccag ggttgaaatt atcacagaat aaggattctg ggcaaggtta  960
ctgcattccg gatctctgtg ggctcttca ccaattttc cagcctcatt tatagtaaac    1020
aaattgttct aatccattta ctgcagattt caccttata agtttagagg tcatgaaggt  1080 ttaatgatc agtaaagatt taagggttga gatttttaag aggcaagagc tgaaagcaga  1140
agacatgatc attagccata agaaactcaa aggaggaaga cataattagg gaaagaagtc 1200
tatttgatga atatgtgtgt gtaaggtatg ttctgctttc ttgattcaaa aatgaagcag  1260
gcattgtcta gctcttaggt gaagggagtc tctgcttttg aagaatggca caggtaggac  1320
```

-continued

| agaagtatca tccctacccc ctaactaatc tgttattaaa gctacaaatt cttcacacc | 1379 |

<210> SEQ ID NO 7
<211> LENGTH: 1416
<212> TYPE: DNA
<213> ORGANISM: Homo sapiens

<400> SEQUENCE: 7

| cttctctggt tccctgacct cagtgagaca gcagccggcc tggggacctg ggggagacac | 60 |
| ggaggacccc ctggctggag ctgacccaca gagtagggaa tcatggctgg agaattggat | 120 |
| agcagagtaa tgtttgacct ctggaaacac tcattctcaa tgcaagatcc tccgctgcaa | 180 |
| tgctgactca ccatcatatt taagaacatg caggaatgca ttgatcagaa ggtgtatcag | 240 |
| gctgaggtgg ataatcttcc tgtagccttt gaagatggtt ctatcaatgg aggtgaccga | 300 |
| cctggggggat ccagtttgtc gattcaaact gctaaccctg gaaccatgt ggagatccaa | 360 |
| gctgcctaca ttggcacaac tataatcatt cggcagacag ctgggcagct ctccttctcc | 420 |
| atcaaggtag cagaggatgt ggccatggcc ttctcagctg aacaggacct gcagctctgt | 480 |
| gttggggggt gccctccaag tcagcgactc tctcgatcag agcgcaatcg tcggggagct | 540 |
| ataaccattg atactgccag acggctgtgc aaggaagggc ttccagtgga agatgcttac | 600 |
| ttccattcct gtgtctttga tgttttaatt tctggtgatc ccaactttac cgtggcagct | 660 |
| caggcagcac tggaggatgc cgagccttc ctgccagact tagagaagct gcatctcttc | 720 |
| ccctcagatg ctggggttcc tcttccctca gcaaccctct tagctccact cctttctggg | 780 |
| ctctttgttc tgtggctttg cattcagtaa ggggaccatc agtcccatta ctagtttgga | 840 |
| aatgatttgg agatacagat tggcatagaa gaatgtaaag aatcattaaa ggaagcaggg | 900 |
| cctaggagac acgtgaaaca atgacattat ccagagtcag atgaggctgc agtccagggt | 960 |
| tgaaattatc acagaataag gattctgggc aaggttactg cattccggat ctctgtgggg | 1020 |
| ctcttcacca atttttccag cctcatttat agtaaacaaa ttgttctaat ccatttactg | 1080 |
| cagatttcac ccttataagt ttagaggtca tgaaggtttt aatgatcagt aaagatttaa | 1140 |
| gggttgagat tttaagagg caagagctga agcagaaga catgatcatt agccataaga | 1200 |
| aactcaaagg aggaagacat aattagggaa agaagtctat ttgatgaata tgtgtgtgta | 1260 |
| aggtatgttc tgctttcttg attcaaaaat gaagcaggca ttgtctagct cttaggtgaa | 1320 |
| gggagtctct gcttttgaag aatggcacag gtaggacaga agtatcatcc ctaccccta | 1380 |
| actaatctgt tattaaagct acaaattctt cacacc | 1416 |

<210> SEQ ID NO 8
<211> LENGTH: 1939
<212> TYPE: DNA
<213> ORGANISM: Homo sapiens

<400> SEQUENCE: 8

| cttctctggt tccctgacct cagtgagaca gcagccggcc tggggacctg ggggagacac | 60 |
| ggaggacccc ctggctggag ctgacccaca gagtagggaa tcatggctgg agaattggat | 120 |
| agcagagtaa tgtttgacct ctggaaacac tcattctcaa tgcaagatcc tccgctgcaa | 180 |
| tgctgagtac gtatcgtcca ctctgagcct tagaggtggg ggttcatcag gagcacttcg | 240 |
| aggaggagga ggaggaggcc ggggtggagg ggtgggctct ggcggcctct gtcgagccct | 300 |
| ccgctcctat gcgctctgca ctcggcgcac cgcccgcacc tgccgcgggg acctcgcctt | 360 |
| ccattcggcg gtacatggca tcgaagacct gatgatccag cacaactgct cccgccaggg | 420 |

-continued

| | |
|---|---|
| ccctacagcc cctcccccgc cccggggccc cgcccttcca ggcgcgggct ccggcctccc | 480 |
| tgccccggac ccttgtgact atgaaggccg gttttcccgg ctgcatggtc gtccccgggg | 540 |
| gttcttgcat tgcgcttcct tcggggaccc ccatgtgcgc agcttccacc atcactttca | 600 |
| cacatgccgt gtccaaggag cttggcctct actggataat gacttcctct ttgtccaagc | 660 |
| caccagctcc cccatggcgt tgggggccaa cgctaccgcc acccggaagc tcaccatcat | 720 |
| atttaagaac atgcaggaat gcattgatca gaaggtgtat caggctgagg tggataatct | 780 |
| tcctgtagcc tttgaagatg gttctatcaa tggaggtgac cgacctgggg gatccagttt | 840 |
| gtcgattcaa actgctaacc ctgggaacca tgtggagatc caagctgcct acattggcac | 900 |
| aactataatc attcggcaga cagctgggca gctctccttc tccatcaagg tagcagagga | 960 |
| tgtggccatg gccttctcag ctgaacagga cctgcagctc tgtgttgggg ggtgccctcc | 1020 |
| aagtcagcga ctctctcgat cagagcgcaa tcgtcgggga gctataacca ttgatactgc | 1080 |
| cagacggctg tgcaaggaag ggcttccagt ggaagatgct tacttccatt cctgtgtctt | 1140 |
| tgatgtttta atttctggtg atcccaactt taccgtggca gctcaggcag cactggagga | 1200 |
| tgcccgagcc ttcctgccag acttagagaa gctgcatctc ttcccctcag atgctggggt | 1260 |
| tcctctttcc tcagcaaccc tcttagctcc actcctttct gggctctttg ttctgtggct | 1320 |
| ttgcattcag taaggggacc atcagtccca ttactagttt ggaaatgatt tggagataca | 1380 |
| gattggcata gaagaatgta aagaatcatt aaaggaagca gggcctagga gacacgtgaa | 1440 |
| acaatgacat tatccagagt cagatgaggc tgcagtccag ggttgaaatt atcacagaat | 1500 |
| aaggattctg ggcaaggtta ctgcattccg gatctctgtg gggctcttca ccaattttc | 1560 |
| cagcctcatt tatagtaaac aaattgttct aatccattta ctgcagattt caccttata | 1620 |
| agtttagagg tcatgaaggt tttaatgatc agtaaagatt taagggttga gatttttaag | 1680 |
| aggcaagagc tgaaagcaga agacatgatc attagccata agaaactcaa aggaggaaga | 1740 |
| cataattagg gaaagaagtc tatttgatga atatgtgtgt gtaaggtatg ttctgctttc | 1800 |
| ttgattcaaa aatgaagcag gcattgtcta gctcttaggt gaagggagtc tctgcttttg | 1860 |
| aagaatggca caggtaggac agaagtatca tccctacccc ctaactaatc tgttattaaa | 1920 |
| gctacaaatt cttcacacc | 1939 |

<210> SEQ ID NO 9
<211> LENGTH: 2143
<212> TYPE: DNA
<213> ORGANISM: Homo sapiens

<400> SEQUENCE: 9

| | |
|---|---|
| cttctctggt tccctgacct cagtgagaca gcagccggcc tggggacctg ggggagacac | 60 |
| ggaggacccc ctggctggag ctgacccaca gagtagggaa tcatggctgg agaattggat | 120 |
| agcagagtaa tgtttgacct ctggaaacac caaatttctt ttttcagtca cttacagggc | 180 |
| ttccggtcaa aattcactag gtaggagggt catcagctgg aagaaccgg cgcctgggaa | 240 |
| acctggctgg ataggtatgg gggagccagg ccagtcccct agtcccaggt cctcccatgg | 300 |
| cagtccccca actctaagca ctctcactct cctgctgctc ctctgtggac atgctcattc | 360 |
| tcaatgcaag atcctccgct gcaatgctga gtacgtatcg tccactctga gccttagagg | 420 |
| tgggggttca tcaggagcac ttcgaggagg aggaggagga ggccggggtg gagggtggg | 480 |
| ctctggcggc ctctgtcgag ccctccgctc ctatgcgctc tgcactcggc gcaccgcccg | 540 |
| cacctgccgc ggggacctcg ccttccattc ggcggtacat ggcatcgaag acctgatgat | 600 |

-continued

```
ccagcacaac tgctcccgcc agggccctac agccctcccc cgccccgggg gccccgccct   660
tccaggcgcg ggctccggcc tccctgcccc ggacccttgt gactatgaag gccggttttc   720
ccggctgcat ggtcgtcccc cggggttctt gcattgcgct tccttcgggg accccccatgt  780
gcgcagcttc caccatcact ttcacacatg ccgtgtccaa ggagcttggc ctctactgga   840
taatgacttc ctctttgtcc aagccaccag ctcccccatg gcgttggggg ccaacgctac   900
cgccacccgg aagctcacca tcatatttaa gaacatgcag gaatgcattg atcagaaggt   960
gtatcaggct gaggtggata atcttcctgt agcctttgaa gatggttcta tcaatggagg  1020
tgaccgacct gggggatcca gtttgtcgat tcaaactgct aaccctggga accatgtgga  1080
gatccaagct gcctacattg cacaactat aatcattcgg cagacagctg gcagctctc   1140
cttctccatc aaggtagcag aggatgtggc catggccttc tcagctgaac aggacctgca  1200
gctctgtgtt gggggggtgcc ctccaagtca gcgactctct cgatcagagc gcaatcgtcg  1260
gggagctata accattgata ctgccagacg gctgtgcaag gaagggcttc cagtggaaga  1320
tgcttacttc cattcctgtg tctttgatgt tttaatttct ggtgatccca actttaccgt  1380
ggcagctcag gcagcactgg aggatgcccg agccttcctg ccagacttag agaagctgca  1440
tctcttcccc tcagatgctg gggttcctct ttcctcagca accctcttag ctccactcct  1500
ttctgggctc tttgttctgt ggctttgcat tcagtaaggg gaccatcagt cccattacta  1560
gtttggaaat gatttggaga tacagattgg catagaagaa tgtaaagaat cattaaagga  1620
agcagggcct aggagacacg tgaaacaatg acattatcca gagtcagatg aggctgcagt  1680
ccagggttga aattatcaca gaataaggat tctgggcaag gttactgcat tccggatctc  1740
tgtggggctc ttcaccaatt tttccagcct catttatagt aaacaaattg ttctaatcca  1800
tttactgcag atttcaccct tataagttta gaggtcatga aggttttaat gatcagtaaa  1860
gatttaaggg ttgagatttt taagaggcaa gagctgaaag cagaagacat gatcattagc  1920
cataagaaac tcaaaggagg aagacataat tagggaaaga agtctatttg atgaatatgt  1980
gtgtgtaagg tatgttctgc tttcttgatt caaaaatgaa gcaggcattg tctagctctt  2040
aggtgaaggg agtctctgct tttgaagaat ggcacaggta ggacagaagt atcatcccta  2100
cccccctaact aatctgttat taaagctaca aattcttcac acc                    2143
```

<210> SEQ ID NO 10
<211> LENGTH: 200
<212> TYPE: PRT
<213> ORGANISM: Homo sapiens

<400> SEQUENCE: 10

```
Met Gln Glu Cys Ile Asp Gln Lys Val Tyr Gln Ala Glu Val Asp Asn
1               5                   10                  15

Leu Pro Val Ala Phe Glu Asp Gly Ser Ile Asn Gly Gly Asp Arg Pro
            20                  25                  30

Gly Gly Ser Ser Leu Ser Ile Gln Thr Ala Asn Pro Gly Asn His Val
        35                  40                  45

Glu Ile Gln Ala Ala Tyr Ile Gly Thr Thr Ile Ile Arg Gln Thr
    50                  55                  60

Ala Gly Gln Leu Ser Phe Ser Ile Lys Val Ala Glu Asp Val Ala Met
65                  70                  75                  80

Ala Phe Ser Ala Glu Gln Asp Leu Gln Leu Cys Val Gly Gly Cys Pro
                85                  90                  95

Pro Ser Gln Arg Leu Ser Arg Ser Glu Arg Asn Arg Arg Gly Ala Ile
            100                 105                 110
```

Thr Ile Asp Thr Ala Arg Arg Leu Cys Lys Glu Gly Leu Pro Val Glu
            115                 120                 125

Asp Ala Tyr Phe His Ser Cys Val Phe Asp Val Leu Ile Ser Gly Asp
        130                 135                 140

Pro Asn Phe Thr Val Ala Ala Gln Ala Ala Leu Glu Asp Ala Arg Ala
145                 150                 155                 160

Phe Leu Pro Asp Leu Glu Lys Leu His Leu Phe Pro Ser Asp Ala Gly
                165                 170                 175

Val Pro Leu Ser Ser Ala Thr Leu Leu Ala Pro Leu Leu Ser Gly Leu
            180                 185                 190

Phe Val Leu Trp Leu Cys Ile Gln
            195                 200

<210> SEQ ID NO 11
<211> LENGTH: 313
<212> TYPE: PRT
<213> ORGANISM: Homo sapiens

<400> SEQUENCE: 11

Met Ile Gln His Asn Cys Ser Arg Gln Gly Pro Thr Ala Pro Pro Pro
1               5                   10                  15

Pro Arg Gly Pro Ala Leu Pro Gly Ala Gly Ser Gly Leu Pro Ala Pro
            20                  25                  30

Asp Pro Cys Asp Tyr Glu Gly Arg Phe Ser Arg Leu His Gly Arg Pro
        35                  40                  45

Pro Gly Phe Leu His Cys Ala Ser Phe Gly Asp Pro His Val Arg Ser
    50                  55                  60

Phe His His His Phe His Thr Cys Arg Val Gln Gly Ala Trp Pro Leu
65                  70                  75                  80

Leu Asp Asn Asp Phe Leu Phe Val Gln Ala Thr Ser Ser Pro Met Ala
                85                  90                  95

Leu Gly Ala Asn Ala Thr Ala Thr Arg Lys Leu Thr Ile Ile Phe Lys
            100                 105                 110

Asn Met Gln Glu Cys Ile Asp Gln Lys Val Tyr Gln Ala Glu Val Asp
        115                 120                 125

Asn Leu Pro Val Ala Phe Glu Asp Gly Ser Ile Asn Gly Gly Asp Arg
    130                 135                 140

Pro Gly Gly Ser Ser Leu Ser Ile Gln Thr Ala Asn Pro Gly Asn His
145                 150                 155                 160

Val Glu Ile Gln Ala Ala Tyr Ile Gly Thr Thr Ile Ile Ile Arg Gln
                165                 170                 175

Thr Ala Gly Gln Leu Ser Phe Ser Ile Lys Val Ala Glu Asp Val Ala
            180                 185                 190

Met Ala Phe Ser Ala Glu Gln Asp Leu Gln Leu Cys Val Gly Gly Cys
        195                 200                 205

Pro Pro Ser Gln Arg Leu Ser Arg Ser Glu Arg Asn Arg Arg Gly Ala
    210                 215                 220

Ile Thr Ile Asp Thr Ala Arg Arg Leu Cys Lys Glu Gly Leu Pro Val
225                 230                 235                 240

Glu Asp Ala Tyr Phe His Ser Cys Val Phe Asp Val Leu Ile Ser Gly
                245                 250                 255

Asp Pro Asn Phe Thr Val Ala Ala Gln Ala Ala Leu Glu Asp Ala Arg
            260                 265                 270

Ala Phe Leu Pro Asp Leu Glu Lys Leu His Leu Phe Pro Ser Asp Ala
        275                 280                 285

Gly Val Pro Leu Ser Ser Ala Thr Leu Leu Ala Pro Leu Leu Ser Gly
        290                 295                 300

Leu Phe Val Leu Trp Leu Cys Ile Gln
305                 310

<210> SEQ ID NO 12
<211> LENGTH: 426
<212> TYPE: PRT
<213> ORGANISM: Homo sapiens

<400> SEQUENCE: 12

Met Gly Glu Pro Gly Gln Ser Pro Ser Pro Arg Ser Ser His Gly Ser
1               5                   10                  15

Pro Pro Thr Leu Ser Thr Leu Thr Leu Leu Leu Leu Leu Cys Gly His
            20                  25                  30

Ala His Ser Gln Cys Lys Ile Leu Arg Cys Asn Ala Glu Tyr Val Ser
        35                  40                  45

Ser Thr Leu Ser Leu Arg Gly Gly Ser Gly Ala Leu Arg Gly
    50                  55                  60

Gly Gly Gly Gly Arg Gly Gly Val Gly Ser Gly Gly Leu Cys
65                  70                  75                  80

Arg Ala Leu Arg Ser Tyr Ala Leu Cys Thr Arg Arg Thr Ala Arg Thr
                85                  90                  95

Cys Arg Gly Asp Leu Ala Phe His Ser Ala Val His Gly Ile Glu Asp
            100                 105                 110

Leu Met Ile Gln His Asn Cys Ser Arg Gln Gly Pro Thr Ala Pro Pro
        115                 120                 125

Pro Pro Arg Gly Pro Ala Leu Pro Gly Ala Gly Ser Gly Leu Pro Ala
    130                 135                 140

Pro Asp Pro Cys Asp Tyr Glu Gly Arg Phe Ser Arg Leu His Gly Arg
145                 150                 155                 160

Pro Pro Gly Phe Leu His Cys Ala Ser Phe Gly Asp Pro His Val Arg
                165                 170                 175

Ser Phe His His His Phe His Thr Cys Arg Val Gln Gly Ala Trp Pro
            180                 185                 190

Leu Leu Asp Asn Asp Phe Leu Phe Val Gln Ala Thr Ser Ser Pro Met
        195                 200                 205

Ala Leu Gly Ala Asn Ala Thr Ala Thr Arg Lys Leu Thr Ile Ile Phe
    210                 215                 220

Lys Asn Met Gln Glu Cys Ile Asp Gln Lys Val Tyr Gln Ala Glu Val
225                 230                 235                 240

Asp Asn Leu Pro Val Ala Phe Glu Asp Gly Ser Ile Asn Gly Gly Asp
                245                 250                 255

Arg Pro Gly Gly Ser Ser Leu Ser Ile Gln Thr Ala Asn Pro Gly Asn
            260                 265                 270

His Val Glu Ile Gln Ala Ala Tyr Ile Gly Thr Thr Ile Ile Ile Arg
        275                 280                 285

Gln Thr Ala Gly Gln Leu Ser Phe Ser Ile Lys Val Ala Glu Asp Val
    290                 295                 300

Ala Met Ala Phe Ser Ala Glu Gln Asp Leu Gln Leu Cys Val Gly Gly
305                 310                 315                 320

Cys Pro Pro Ser Gln Arg Leu Ser Arg Ser Glu Arg Asn Arg Arg Gly
                325                 330                 335

Ala Ile Thr Ile Asp Thr Ala Arg Arg Leu Cys Lys Glu Gly Leu Pro
            340                 345                 350

```
Val Glu Asp Ala Tyr Phe His Ser Cys Val Phe Asp Val Leu Ile Ser
        355                 360                 365

Gly Asp Pro Asn Phe Thr Val Ala Ala Gln Ala Ala Leu Glu Asp Ala
    370                 375                 380

Arg Ala Phe Leu Pro Asp Leu Glu Lys Leu His Leu Phe Pro Ser Asp
385                 390                 395                 400

Ala Gly Val Pro Leu Ser Ser Ala Thr Leu Leu Ala Pro Leu Leu Ser
                405                 410                 415

Gly Leu Phe Val Leu Trp Leu Cys Ile Gln
            420                 425

<210> SEQ ID NO 13
<211> LENGTH: 21
<212> TYPE: DNA
<213> ORGANISM: Artificial
<220> FEATURE:
<223> OTHER INFORMATION: Polynucleotide replication primer

<400> SEQUENCE: 13
gctgcctaca ttggcacaac t                                           21

<210> SEQ ID NO 14
<211> LENGTH: 21
<212> TYPE: DNA
<213> ORGANISM: Artificial
<220> FEATURE:
<223> OTHER INFORMATION: Polynucleotide replication primer

<400> SEQUENCE: 14
gctgcctaca ctggcacaac t                                           21

<210> SEQ ID NO 15
<211> LENGTH: 21
<212> TYPE: DNA
<213> ORGANISM: Artificial
<220> FEATURE:
<223> OTHER INFORMATION: Polynucleotide replication primer

<400> SEQUENCE: 15
tgtgttgggg ggtgccctcc a                                           21

<210> SEQ ID NO 16
<211> LENGTH: 21
<212> TYPE: DNA
<213> ORGANISM: Artificial
<220> FEATURE:
<223> OTHER INFORMATION: Polynucleotide replication primer

<400> SEQUENCE: 16
tgtgttgggg tgtgccctcc a                                           21

<210> SEQ ID NO 17
<211> LENGTH: 21
<212> TYPE: DNA
<213> ORGANISM: Artificial
<220> FEATURE:
<223> OTHER INFORMATION: Polynucleotide replication primer

<400> SEQUENCE: 17
tacttccatt cctgtgtctt t                                           21

<210> SEQ ID NO 18
<211> LENGTH: 20
<212> TYPE: DNA
```

<213> ORGANISM: Artificial
<220> FEATURE:
<223> OTHER INFORMATION: Polynucleotide replication primer

<400> SEQUENCE: 18
tacttccatt ctgtgtcttt                                                      20

<210> SEQ ID NO 19
<211> LENGTH: 1919
<212> TYPE: DNA
<213> ORGANISM: Homo sapiens

<400> SEQUENCE: 19

| tctatataga | tattaataaa | tctagagaga | cagaaagcag | actggtgatg | ccagtctag  | 60   |
| atggctagat | agatagacat | ggatatagat | atagatctct | atatagatag | aggtagatac | 120  |
| agatatagat | atatgcccta | ttagttctgt | tcctctagag | aaccctaata | cagtgaccgt | 180  |
| atttggaatc | ggtccttctg | ttaatttcac | ttggcaagta | ctaaaagatg | atgatctcag | 240  |
| atatacctat | ggctgcaaaa | acatgacatg | ctaaatccc | ttggttgcag | tatctctttt | 300  |
| cttttttaag | gggggtgggg | gggcgggtct | cactgttgcc | caggctggag | tgcaatggcg | 360  |
| ttatcatagc | tcactgcagc | ctcaaactcc | tgcgctcaag | tgaccctcct | gcctcagctc | 420  |
| ccaaagtgct | gagattttgc | aatatttatg | gtcacaagat | tatgttattc | cataaaagta | 480  |
| tctttctgag | gctaggcatg | ttggttcaca | cttgtaatcc | cagcactctg | agaggctgag | 540  |
| atggaaggat | tcattgaggc | aaggagttca | agaccagcct | ggtcaacata | gtgagacctc | 600  |
| atctcggaag | gaaggaagga | aggagggagg | gaggaaggga | gggagtgaag | gaaggaagga | 660  |
| aggaaggaag | gaaggaagga | aggaaggaag | gaaggaagga | aaagtatatt | tttgaatctt | 720  |
| tttctatttc | tccaactctt | tctttagaag | aattctattt | ccattctttc | ttcacctctt | 780  |
| tgcctttgtt | agccttctct | ccaagcaaat | cgggagcctt | tatttttgt  | gtattcatga | 840  |
| gggagaggaa | gatgaattgc | tgtacaaact | aaagtaatga | aaatggagta | ggtaggagga | 900  |
| tagacagctg | caaggatctg | agctggatag | actgaacaaa | ccctcatcct | aagcaactca | 960  |
| cagctcagat | ttcttctctg | gacagctggc | tttttttcgtc | cttctgaaat | actctgcaaa | 1020 |
| gataggagag | gggctatgaa | ctacctctgc | tatggatctt | attcaaagtc | agctacctcc | 1080 |
| tagatactat | ctgtagaacc | taaatgtaat | attcagcata | gcagggatga | acatggtaaa | 1140 |
| tgaaaggtat | ccaattgccc | actgtaattt | ttaaaggcca | ggagctcaac | attattgaaa | 1200 |
| atgctggagg | gctgcctgga | gtaggcagtg | accacagagt | cacacaagct | ggaattggat | 1260 |
| atccaacttg | tctgtcatat | ttctctcctc | cctccctgac | ttggcactca | atactccata | 1320 |
| ttctttctaa | tcctctaacc | ctccccactc | ccccaactcc | cacaccctac | ccccaccaac | 1380 |
| gttcctggaa | ttttggactt | agctattttt | aaaaccgtca | actcagtagc | cacctccctc | 1440 |
| cctgctcagc | tgtccagtac | tctggccagc | catatactcc | cccttccccc | cataccaaac | 1500 |
| cttctctggt | tccctgacct | cagtgagaca | gcagccggcc | tggggacctg | ggggagacac | 1560 |
| ggaggaccccc | ctggctggag | ctgacccaca | gagtagggaa | tcatggctgg | agaattggat | 1620 |
| agcagagtaa | tgtttgacct | ctggaaacag | taagtcaaaa | tgaaattgca | attcctttaa | 1680 |
| taagctttta | tattgaagtt | agactttttat | aaaattacaa | acacctactt | ggatgtctct | 1740 |
| cgtccaaatg | ctgggatctc | tccctaccaa | ggtgccccaa | tctccatttc | tctttctgtc | 1800 |
| ttatttcttt | ctggcctctg | gcctctagct | ttttgaagtt | taattctctg | tctctcctct | 1860 |
| ggcagtctta | gccctctctt | taccttatta | cctcaagact | cctgatgaag | ttttagaag  | 1919 |

<210> SEQ ID NO 20
<211> LENGTH: 1020
<212> TYPE: DNA
<213> ORGANISM: Mus musculus

<400> SEQUENCE: 20

```
tgtattgacg aggaggaggg attgttgcac acactagcgt aatggaaaag gtggagatag     60
aatagacagc tgcagagatc tgatccggac agacagaata aaccctcctc cgaaacaatt    120
ctgctctcgg gtttcttctc cagacagctg gcctttcggc ttctgaaata gttggcggag    180
atggggagg gtctctgaac tacgcctgcc atccatcttc aaagccagct acctctacgt    240
accatgtgtg gaaactcagt ggcatcctca gtaaagagag gatgagaacg gtgagtgaca    300
ggcgtcacac aaatcaccac cagccgtctt acaggccggg agctcattac tgagaacgct    360
aaaggacctg agtggcaggt catacaagct gcagttggac atgggacttg ccatcgttc     420
tctctttagg cagtccctca cttggtaccc agcattccca tattccctct ttattttgct    480
catcattcct gctgccttag ctcccacacc ctactgccac caacgttcct ggaattttgg    540
acctagctat ttttaaaact gtcaactcag gaggcacctc cctcctcctc tcagctgtcc    600
agtgcttggg ccaaccatat actctccctg cccctcccc ccacaccaaa gctcctctgg    660
ctctctgacc tcggtgagat tgcagccagt ccggggatc ggggacagac atggagaagg    720
agatggagga cccctggct ggagcagacc aacagaatag gcaactatgg ctggagaacc     780
gggtatcaga gtaatgcttg acctcgggaa acagtaagtc tagatgaaat ggcggttgct    840
ttgataagct tttgggtcga ggctagaatt tcataaagtt acagacatct gttctgaaaa    900
ctaagatctc tccttaccag ataccccaat cttcactttt ggaccgcctg ctcatacact    960
tattccaaag aagggttttg acaggagaaa gggagacaga cccctcccaa tatctgttcc   1020
```

<210> SEQ ID NO 21
<211> LENGTH: 1120
<212> TYPE: DNA
<213> ORGANISM: Rattus rattus

<400> SEQUENCE: 21

```
tctggcccca cttctctgtg gatcggtcat cttcaaaacc agttcagctt cccactgccc     60
ccaccacccc cgaaacccgg aagcttctgt tttttgtgtt tgtattgacg aggaggaggg    120
attgttgcac acactagcgt aatggaaaag gtggagatag aatagacagc tgcagagatc    180
tgatccggac agacagaata aaccctcctc cgaaacaatt ctgctctcgg gtttcttctc    240
cagacagctg gcctttcggc ttctgaaata gttggcggag atggggagg gtctctgaac     300
tacgcctgcc atccatcttc aaagccagct acctctacgt accatgtgtg gaaactcagt    360
ggcatcctca gtaaagagag gatgagaacg gtgagtgaca ggcgtcacac aaatcaccac    420
cagccgtctt acaggccggg agctcattac tgagaacgct aaaggacctg agtggcaggt    480
catacaagct gcagttggac atgggacttg ccatcgttc tctctttagg cagtccctca     540
cttggtaccc agcattccca tattccctct ttattttgct catcattcct gctgccttag    600
ctcccacacc ctactgccac caacgttcct ggaattttgg acctagctat ttttaaaact    660
gtcaactcag gaggcacctc cctcctcctc tcagctgtcc agtgcttggg ccaaccatat    720
actctccctg cccctcccc ccacaccaaa gctcctctgg ctctctgacc tcggtgagat     780
tgcagccagt ccggggatc ggggacagac atggagaagg agatggagga cccctggct     840
ggagcagacc aacagaatag gcaactatgg ctggagaacc gggtatcaga gtaatgcttg    900
```

| | |
|---|---|
| acctcgggaa acagtaagtc tagatgaaat ggcggttgct ttgataagct tttgggtcga | 960 |
| ggctagaatt tcataaagtt acagacatct gttctgaaaa ctaagatctc tccttaccag | 1020 |
| atacccaat cttcactttt ggaccgcctg ctcatacact tattccaaag aagggttttg | 1080 |
| acaggagaaa gggagacaga cccctcccaa tatctgttcc | 1120 |

<210> SEQ ID NO 22
<211> LENGTH: 7265
<212> TYPE: DNA
<213> ORGANISM: Homo sapiens

<400> SEQUENCE: 22

| | |
|---|---|
| tctatataga tattaataaa tctagagaga cagaaagcag actggtgatg ccagtctag | 60 |
| atggctagat agatagacat ggatatagat atagatctct atatagatag aggtagatac | 120 |
| agatatagat atatgcccta ttagttctgt tcctctagag aaccctaata cagtgaccgt | 180 |
| atttggaatc ggtccttctg ttaatttcac ttggcaagta ctaaaagatg atgatctcag | 240 |
| atatacctat ggctgcaaaa acatgacatg ctaaatccc ttggttgcag tatctctttt | 300 |
| cttttttaag gggggtgggg gggcgggtct cactgttgcc caggctggag tgcaatggcg | 360 |
| ttatcatagc tcactgcagc ctcaaactcc tgcgctcaag tgaccctcct gcctcagctc | 420 |
| ccaaagtgct gagattttgc aatatttatg gtcacaagat tatgttattc cataaaagta | 480 |
| tctttctgag gctaggcatg ttggttcaca cttgtaatcc cagcactctg agaggctgag | 540 |
| atggaaggat tcattgaggc aaggagttca agaccagcct ggtcaacata gtgagacctc | 600 |
| atctcggaag gaaggaagga aggagggagg gaggaaggga gggagtgaag gaaggaagga | 660 |
| aggaaggaag gaaggaagga aggaaggaag gaaggaagga aaagtatatt tttgaatctt | 720 |
| tttctatttc tccaactctt tctttagaag aattctattt ccattctttc ttcacctctt | 780 |
| tgcctttgtt agccttctct ccaagcaaat cgggagcctt tattttttgt gtattcatga | 840 |
| gggagaggaa gatgaattgc tgtacaaact aaagtaatga aaatggagta ggtaggagga | 900 |
| tagacagctg caaggatctg agctggatag actgaacaaa ccctcatcct aagcaactca | 960 |
| cagctcagat ttcttctctg gacagctggc ttttttcgtc cttctgaaat actctgcaaa | 1020 |
| gataggagag gggctatgaa ctacctctgc tatggatctt attcaaagtc agctacctcc | 1080 |
| tagatactat ctgtagaacc taaatgtaat attcagcata gcaggatga acatggtaaa | 1140 |
| tgaaaggtat ccaattgccc actgtaattt ttaaaggcca ggagctcaac attattgaaa | 1200 |
| atgctggagg gctgcctgga gtaggcagtg accacagagt cacacaagct ggaattggat | 1260 |
| atccaacttg tctgtcatat ttctctcctc cctccctgac ttggcactca atactccata | 1320 |
| ttctttctaa tcctctaacc ctccccactc ccccaactcc cacaccctac ccccaccaac | 1380 |
| gttcctggaa ttttggactt agctattttt aaaaccgtca actcagtagc cacctccctc | 1440 |
| cctgctcagc tgtccagtac tctggccagc catatactcc cccttccccc cataccaaac | 1500 |
| cttctctggt tccctgacct cagtgagaca gcagccggcc tggggacctg ggggagacac | 1560 |
| ggaggacccc ctggctggag ctgacccaca gagtagggaa tcatggctgg agaattggat | 1620 |
| agcagagtaa tgtttgacct ctggaaacag taagtcaaaa tgaaattgca attcctttaa | 1680 |
| taagcttta tattgaagtt agactttat aaaattacaa acacctactt ggatgtctct | 1740 |
| cgtccaaatg ctgggatctc tccctaccaa ggtgccccaa tctccatttc tctttctgtc | 1800 |
| ttatttcttt ctggcctctg gcctctagct ttttgaagtt taattctctg tctctcctct | 1860 |
| ggcagtctta gccctctctt taccttatta cctcaagact cctgatgaag ttttagaagg | 1920 |

```
agttccctac gtcctctatt ctgtagtttt cttaccaagg ccaaatatga cctcagatga   1980
tgagtcactg ataccttct atcctgcccc cacttagcaa tgcccttcac attgagattc    2040
caagcatggg ggctgctccc tgtaaatgat ttctccccac aactctagtc cctccattct   2100
attctccctc ttgcaggact cttcccccaa tcatatcctt acccataaga taggggagtt   2160
aggcaggagg gatttagccc ctctccaact cctgtcatca taaaagactg agaacttcag   2220
aatttgaaaa gaagagatta atggaaggag tgatatttgg gaaaatacaa gaactgttga   2280
cttagaaaaa acaaatattg atttgcatgt ttggtttgca tcccattatt ccatgagaga   2340
gggagattaa aattgcagct ctctagagct gatgaaaaga gattggtttc cttttcattt   2400
gaatactgat attctagacg ggatgggtat gccacccta atccttcttg tgttctgaca    2460
caaaggagga aaagaaatgt atgactccta gagggcatct cctcctaatg gagagggaca   2520
aataagaagt atgtttctga aatattttca ggtcctaatt ttactagggt acccactagg   2580
attactggta tctgatctag ccccatgatt cctccatctt tgacatacct gctgtttggt   2640
agctcagaat ggagcaatac agtggactct gccccttga gttcactcaa ccttccctcc    2700 accccacct agggqtattg cacaagqgcc ctaaaagtgg ccacaggaac agggcaaaga    2760
ggcttaactg ccacacttat agtttgagga actccaatct ccccaaattc cagtctgttc   2820 atcctttct tgatctcccc agattcactc cacattatcc ttaccaatct tcaattcttc    2880
tctctctcca tgtccagcca aatttctttt ttcagtcact tacagggctt ccggtcaaaa   2940
ttcactaggt aggagggtca tcagctggga agaaccggcg cctgggaaac ctggctggat   3000
aggtatgggg gagccaggcc agtcccctag tcccaggtcc tcccatggca gtcccccaac   3060
tctaagcact ctcactctcc tgctgctcct ctgtggacat ggtaaggaag ggccagggaa   3120
gggtttgggg aaatctagag ggtaggctgc tatgtagggg tgggcatgtg agcctgaatg   3180
agtgaggaga gataggcgct gagagtcccg atcactcgcc ctgctctcaa atactaatat   3240
tttatttccc gttcagtctg gggaaggcca ctggggaagc ccttggtcga caggcagaag   3300
agatgtggca ggcttacaca cttttagtaa gacagccgag agaactaggg actaggggt    3360 tgggggctgg ggaaggccct tagttaggtt ttaggaaggc tggaaacccc tgatgagatt   3420
tggaagagtt atgagcaaac tacactccga tagagcagag gtctgaggac cgtctcacaa   3480
tcctctccct tctgtcttta gctcattctc aatgcaagat cctccgctgc aatgctgagt   3540
acgtatcgtc cactctgagc cttagaggtg ggggttcatc aggagcactt cgaggaggag   3600
gaggaggagg ccgggqtgga ggggtgggct ctggcggcct ctgtcgagcc ctccgctcct   3660
atgcgctctg cactcggcgc accgcccgca cctgccgcgg ggacctcgcc ttccattcgg   3720
cggtacatgg catcgaagac ctgatgatcc agcacaactg ctcccgccag ggccctacag   3780
cccctccccc gccccggggc cccgccctttc caggcgcggg ctccggcctc cctgccccgg   3840
acccttgtga ctatgaaggc cggttttccc ggctgcatgg tcgtcccccg ggttcttgc    3900 attgcgcttc cttcggggac ccccatgtgc gcagcttcca ccatcacttt cacacatgcc   3960
gtgtccaagg agcttggcct ctactggata atgacttcct ctttgtccaa gccaccagct   4020
cccccatggc gttggqgqcc aacgctaccg ccacccggaa ggtcaggcac tcaatcttcc   4080
ttccgatcca cctcatgaga ttcttccacg ggcaccattc ctcccatcc ccactattca    4140 acagcaatgc tccctaattc ccttttcttc ctcaacctct cccccatctc gaatcactcc   4200
cttctaccaa acacctggag ctgtaaatca cttcccttg atgggaattt gactcaaatg    4260
cagaaaacct tgaagagaca gtcggagagg gcggacctga ggagtttcag aagggaaact   4320
```

-continued

```
tttccctctc ctaggaagtt gccacgatta agtagagagg gggttaagta gggatgaggt    4380
aatactggaa cataaatagg agaagggatc aaggattgag ggccatagta gtcctgcatc    4440
tctacttgga tcagatctct aactatgtat gaggtctgat tggggggaag atgcactgaa    4500
cccaaaatga actgttttcc ctcttgtcct cacagctcac catcatattt aagaacatgc    4560
aggaatgcat tgatcagaag gtgtatcagg ctgaggtgga taatcttcct gtagcctttg    4620
aagatggttc tatcaatgga ggtgaccgac ctggggatc cagtttgtcg attcaaactg    4680
ctaaccctgg gaaccatgtg gagatccaag ctgcctacat tggcacaact ataatcattc    4740
ggcagacagc tgggcagctc tccttctcca tcaaggtagc agaggatgtg gccatggcct    4800
tctcagctga acaggacctg cagctctgtg ttgggggtg ccctccaagt cagcgactct    4860
ctcgatcaga gcgcaatcgt cggggagcta taaccattga tactgccaga cggctgtgca    4920
aggaagggct tccagtggaa gatgcttact tccattcctg tgtctttgat gttttaattt    4980
ctggtgatcc caactttacc gtggcagctc aggcagcact ggaggatgcc cgagccttcc    5040
tgccagactt agagaagctg catctcttcc cctcagatgc tggggttcct cttttcctcag   5100 caaccctctt agctccactc ctttctgggc tctttgttct gtggctttgc attcagtaag    5160
gggaccatca gtcccattac tagtttggaa atgatttgga gatacagatt ggcatagaag    5220
aatgtaaaga atcattaaag gaagcagggc ctaggagaca cgtgaaacaa tgacattatc    5280
cagagtcaga tgaggctgca gtccagggtt gaaattatca cagaataagg attctgggca    5340
aggttactgc attccggatc tctgtggggc tcttccaccaa tttttccagc ctcatttata    5400
gtaaacaaat tgttctaatc catttactgc agatttcacc cttataagtt tagaggtcat    5460
gaaggtttta atgatcagta aagatttaag ggttgagatt tttaagaggc aagagctgaa    5520
agcagaagac atgatcatta gccataagaa actcaaagga ggaagacata attagggaaa    5580
gaagtctatt tgatgaatat gtgtgtgtaa ggtatgttct gctttcttga ttcaaaaatg    5640
aagcaggcat tgtctagctc ttaggtgaag ggagtctctg cttttgaaga atggcacagg    5700
taggacagaa gtatcatccc tacccctaa ctaatctgtt attaaagcta caattcttc     5760 acaccatcct ctgttgccta tgttgaatct ctttacagat gcttgaaatg gagtaaatgc    5820
aatgtgttca ctccactgaa agagggctcg gaagtatcag atactgttgc tatctcaggg    5880
agtttacagg ctattggaga gacaaaacca attcacatga aagagtgatg agtgtgtaat    5940
tattcactaa atcctacagt atggtacatt cagatgggaa gatggtagat ttgaactaaa    6000
gtaataagaa taataaaagg taacagagaa gatgggattt gaagtgagct ttgaagactg    6060
ggtaagattc aaattgttaa cgatcttcca ggcaatgaaa accatctgga gttatgcatg    6120
gattcatgat tcagcaagga aatgagcaaa actcaaatgc agtagacaag gagtaatggg    6180
acagaaggtt agatgggcag aggccagatt atgaagcacc ttaaaagggg ggtaagggt    6240 ttaaatttga ttaatatcta acacttattg aaacttaaaa tctgccaggc aatgttttaa    6300
acacttttaa aacattgact taattctcat agctctctaa ggaaggtggt attcttatct    6360
ctatttttat ataaggaaac ttgcctccag tcacacagct aacaaattat ggaacttgcc    6420
tccagtcaca cagttaacaa atggcagagc cagaaactga acctatgccg tttggatccc    6480
gaaacttaat ttttaatcac tatactatat tgtcaaggaa gcagagagcc attaaagatt    6540
ctggttgtgg agctggtaaa gattctaaaa ggggagttgt ggtggtcaat gtcaccacaa    6600
aagctactct gaggctgggc gcggtggctg acacctgtaa tccagcactt tggtaggcca    6660
atgtgggtgg atcacttgag gccaggagtt cgagaccagc ctgggcaaca tggtaaaacc    6720
```

-continued

```
ccatctctac taaaaataca agaaatttgc caggcatgat agtccatgcc tgtaatcctg    6780
taatccaagc tactcaggag gcagaggcat gagaatcgag aattgcttga acccgggcca    6840
ggaggcagag gttgcagtga gctgagacca cgccactgca ctccagcctg ggcaacagag    6900
tgagactatc aaacaaaaaa caactactct cttctcatat tctcatataa agccaaaaag    6960
agagagttgg aaaaggaggg aaagcccaaa gttgaaggaa tctagtttgt agaagaaaga    7020
ctgagaagaa atgctgttct agatgagggt gctctaaagt aacaatgctg ctctgaacaa    7080
aattatgaag gaggtaactt ttacatttaa tatcttccct gtttctggtc tcatcctccc    7140
ctctcaggta ctccataacc gaggacctgt cctccctgcc ctaatcaagt actcaccatt    7200
atcttccacc tctcctctca gtccctgaca cccgacaata ctcccctgaa caaatattac    7260
agtag                                                                7265
```

<210> SEQ ID NO 23
<211> LENGTH: 450
<212> TYPE: PRT
<213> ORGANISM: Homo sapiens

<400> SEQUENCE: 23

```
Met Gln Pro Pro Arg Glu Arg Leu Val Val Thr Gly Arg Ala Gly Trp
1               5                   10                  15

Met Gly Met Gly Arg Gly Ala Gly Arg Ser Ala Leu Gly Phe Trp Pro
            20                  25                  30

Thr Leu Ala Phe Leu Leu Cys Ser Phe Pro Ala Ala Thr Ser Pro Cys
        35                  40                  45

Lys Ile Leu Lys Cys Asn Ser Glu Phe Trp Ser Ala Thr Ser Gly Ser
    50                  55                  60

His Ala Pro Ala Ser Asp Asp Thr Pro Glu Phe Cys Ala Ala Leu Arg
65                  70                  75                  80

Ser Tyr Ala Leu Cys Thr Arg Arg Thr Ala Arg Thr Cys Arg Gly Asp
                85                  90                  95

Leu Ala Tyr His Ser Ala Val His Gly Ile Glu Asp Leu Met Ser Gln
            100                 105                 110

His Asn Cys Ser Lys Asp Gly Pro Thr Ser Gln Pro Arg Leu Arg Thr
        115                 120                 125

Leu Pro Pro Ala Gly Asp Ser Gln Glu Arg Ser Asp Ser Pro Glu Ile
    130                 135                 140

Cys His Tyr Glu Lys Ser Phe His Lys His Ser Ala Thr Pro Asn Tyr
145                 150                 155                 160

Thr His Cys Gly Leu Phe Gly Asp Pro His Leu Arg Thr Phe Thr Asp
                165                 170                 175

Arg Phe Gln Thr Cys Lys Val Gln Gly Ala Trp Pro Leu Ile Asp Asn
            180                 185                 190

Asn Tyr Leu Asn Val Gln Ala Thr Asn Thr Pro Val Leu Pro Gly Ser
        195                 200                 205

Ala Ala Thr Ala Thr Ser Lys Leu Thr Ile Ile Phe Lys Asn Phe Gln
    210                 215                 220

Glu Cys Val Asp Gln Lys Val Tyr Gln Ala Glu Met Asp Glu Leu Pro
225                 230                 235                 240

Ala Ala Phe Val Asp Gly Ser Lys Asn Gly Gly Asp Lys His Gly Ala
                245                 250                 255

Asn Ser Leu Lys Ile Thr Glu Lys Val Ser Gly Gln His Val Glu Ile
            260                 265                 270

Gln Ala Lys Tyr Ile Gly Thr Thr Ile Val Val Arg Gln Val Gly Arg
```

```
                   275                 280                 285
Tyr Leu Thr Phe Ala Val Arg Met Pro Glu Val Val Asn Ala Val
290                 295                 300
Glu Asp Trp Asp Ser Gln Gly Leu Tyr Leu Cys Leu Arg Gly Cys Pro
305                 310                 315                 320
Leu Asn Gln Gln Ile Asp Phe Gln Ala Phe His Thr Asn Ala Glu Gly
                325                 330                 335
Thr Gly Ala Arg Arg Leu Ala Ala Ser Pro Ala Pro Thr Ala Pro
            340                 345                 350
Glu Thr Phe Pro Tyr Glu Thr Ala Val Ala Lys Cys Lys Glu Lys Leu
                355                 360                 365
Pro Val Glu Asp Leu Tyr Tyr Gln Ala Cys Val Phe Asp Leu Leu Thr
370                 375                 380
Thr Gly Asp Val Asn Phe Thr Leu Ala Ala Tyr Tyr Ala Leu Glu Asp
385                 390                 395                 400
Val Lys Met Leu His Ser Asn Lys Asp Lys Leu His Leu Tyr Glu Arg
                405                 410                 415
Thr Arg Asp Leu Pro Gly Arg Ala Ala Ala Gly Leu Pro Leu Ala Pro
            420                 425                 430
Arg Pro Leu Leu Gly Ala Leu Val Pro Leu Leu Ala Leu Leu Pro Val
            435                 440                 445
Phe Cys
    450

<210> SEQ ID NO 24
<211> LENGTH: 478
<212> TYPE: PRT
<213> ORGANISM: Homo sapiens

<400> SEQUENCE: 24

Met Ile Arg Lys Lys Arg Lys Arg Ser Ala Pro Pro Gly Pro Cys Arg
1               5                   10                  15
Ser His Gly Pro Arg Pro Ala Thr Ala Pro Ala Pro Pro Ser Pro
            20                  25                  30
Glu Pro Thr Arg Pro Ala Trp Thr Gly Met Gly Leu Arg Ala Ala Pro
            35                  40                  45
Ser Ser Ala Ala Ala Ala Ala Glu Val Glu Gln Arg Arg Ser Pro
50                  55                  60
Gly Leu Cys Pro Pro Leu Glu Leu Leu Leu Leu Leu Phe Ser
65                  70                  75                  80
Leu Gly Leu Leu His Ala Gly Asp Cys Gln Gln Pro Ala Gln Cys Arg
                85                  90                  95
Ile Gln Lys Cys Thr Thr Asp Phe Val Ser Leu Thr Ser His Leu Asn
                100                 105                 110
Ser Ala Val Asp Gly Phe Asp Ser Glu Phe Cys Lys Ala Leu Arg Ala
            115                 120                 125
Tyr Ala Gly Cys Thr Gln Arg Thr Ser Lys Ala Cys Arg Gly Asn Leu
130                 135                 140
Val Tyr His Ser Ala Val Leu Gly Ile Ser Asp Leu Met Ser Gln Arg
145                 150                 155                 160
Asn Cys Ser Lys Asp Gly Pro Thr Ser Ser Thr Asn Pro Glu Val Thr
                165                 170                 175
His Asp Pro Cys Asn Tyr His Ser His Ala Gly Ala Arg Glu His Arg
            180                 185                 190
Arg Gly Asp Gln Asn Pro Pro Ser Tyr Leu Phe Cys Gly Leu Phe Gly
```

```
                195                 200                 205
Asp Pro His Leu Arg Thr Phe Lys Asp Asn Phe Gln Thr Cys Lys Val
210                 215                 220

Glu Gly Ala Trp Pro Leu Ile Asp Asn Asn Tyr Leu Ser Val Gln Val
225                 230                 235                 240

Thr Asn Val Pro Val Val Pro Gly Ser Ser Ala Thr Ala Thr Asn Lys
                245                 250                 255

Ile Thr Ile Ile Phe Lys Ala His His Glu Cys Thr Asp Gln Lys Val
            260                 265                 270

Tyr Gln Ala Val Thr Asp Asp Leu Pro Ala Ala Phe Val Asp Gly Thr
        275                 280                 285

Thr Ser Gly Gly Asp Ser Asp Ala Lys Ser Leu Arg Ile Val Glu Arg
    290                 295                 300

Glu Ser Gly His Tyr Val Glu Met His Ala Arg Tyr Ile Gly Thr Thr
305                 310                 315                 320

Val Phe Val Arg Gln Val Gly Arg Tyr Leu Thr Leu Ala Ile Arg Met
                325                 330                 335

Pro Glu Asp Leu Ala Met Ser Tyr Glu Glu Ser Gln Asp Leu Gln Leu
            340                 345                 350

Cys Val Asn Gly Cys Pro Leu Ser Glu Arg Ile Asp Asp Gly Gln Gly
        355                 360                 365

Gln Val Ser Ala Ile Leu Gly His Ser Leu Pro Arg Thr Ser Leu Val
    370                 375                 380

Gln Ala Trp Pro Gly Tyr Thr Leu Glu Thr Ala Asn Thr Gln Cys His
385                 390                 395                 400

Glu Lys Met Pro Val Lys Asp Ile Tyr Phe Gln Ser Cys Val Phe Asp
                405                 410                 415

Leu Leu Thr Thr Gly Asp Ala Asn Phe Thr Ala Ala His Ser Ala
            420                 425                 430

Leu Glu Asp Val Glu Ala Leu His Pro Arg Lys Glu Arg Trp His Ile
        435                 440                 445

Phe Pro Ser Ser Gly Asn Gly Thr Pro Arg Gly Gly Ser Asp Leu Ser
    450                 455                 460

Val Ser Leu Gly Leu Thr Cys Leu Ile Leu Ile Val Phe Leu
465                 470                 475

<210> SEQ ID NO 25
<211> LENGTH: 420
<212> TYPE: PRT
<213> ORGANISM: Mus musculus

<400> SEQUENCE: 25

Met Gly Gln Ser Pro Ser Pro Arg Ser Pro His Gly Ser Pro Pro Thr
1               5                   10                  15

Leu Ser Thr Leu Thr Leu Leu Leu Leu Cys Gly Gln Ala His Ser
            20                  25                  30

Gln Cys Lys Ile Leu Arg Cys Asn Ala Glu Tyr Val Ser Ser Thr Leu
        35                  40                  45

Ser Leu Arg Gly Gly Gly Ser Pro Asp Thr Pro Arg Gly Gly Gly Arg
    50                  55                  60

Gly Gly Leu Ala Ser Gly Gly Leu Cys Arg Ala Leu Arg Ser Tyr Ala
65                  70                  75                  80

Leu Cys Thr Arg Arg Thr Ala Arg Thr Cys Arg Gly Asp Leu Ala Phe
                85                  90                  95

His Ser Ala Val His Gly Ile Glu Asp Leu Met Ile Gln His Asn Cys
```

```
            100                 105                 110
Ser Arg Gln Gly Pro Thr Ala Pro Pro Ala Arg Gly Pro Ala Leu
        115                 120                 125

Pro Gly Ala Gly Pro Ala Pro Leu Thr Pro Asp Pro Cys Asp Tyr Glu
    130                 135                 140

Ala Arg Phe Ser Arg Leu His Gly Arg Ala Pro Gly Phe Leu His Cys
145                 150                 155                 160

Ala Ser Phe Gly Asp Pro His Val Arg Ser Phe His Asn Gln Phe His
                165                 170                 175

Thr Cys Arg Val Gln Gly Ala Trp Pro Leu Leu Asp Asn Asp Phe Leu
            180                 185                 190

Phe Val Gln Ala Thr Ser Ser Pro Val Ser Ser Gly Ala Asn Ala Thr
        195                 200                 205

Thr Ile Arg Lys Ile Thr Ile Ile Phe Lys Asn Met Gln Glu Cys Ile
    210                 215                 220

Asp Gln Lys Val Tyr Gln Ala Glu Val Asp Asn Leu Pro Ala Ala Phe
225                 230                 235                 240

Glu Asp Gly Ser Ile Asn Gly Gly Asp Arg Pro Gly Gly Ser Ser Leu
                245                 250                 255

Ser Ile Gln Thr Ala Asn Leu Gly Ser His Val Glu Ile Arg Ala Ala
            260                 265                 270

Tyr Ile Gly Thr Thr Ile Ile Ile Arg Gln Thr Ala Gly Gln Leu Ser
        275                 280                 285

Phe Ser Ile Arg Val Ala Glu Asp Val Ala Arg Ala Phe Ser Ala Glu
    290                 295                 300

Gln Asp Leu Gln Leu Cys Val Gly Gly Cys Pro Pro Ser Gln Arg Leu
305                 310                 315                 320

Ser Arg Ser Glu Arg Asn Arg Gly Ala Ile Ala Ile Asp Thr Ala
                325                 330                 335

Arg Arg Leu Cys Lys Glu Gly Leu Pro Val Glu Asp Ala Tyr Phe Gln
            340                 345                 350

Ser Cys Val Phe Asp Val Ser Val Ser Gly Asp Pro Asn Phe Thr Val
        355                 360                 365

Ala Ala Gln Thr Ala Leu Asp Asp Ala Arg Ile Phe Leu Thr Asp Leu
    370                 375                 380

Glu Asn Leu His Leu Phe Pro Ser Asp Ala Gly Pro Pro Leu Ser Pro
385                 390                 395                 400

Ala Ile Cys Leu Val Pro Leu Leu Ser Ala Leu Phe Val Leu Trp Leu
                405                 410                 415

Cys Phe Ser Lys
            420

<210> SEQ ID NO 26
<211> LENGTH: 422
<212> TYPE: PRT
<213> ORGANISM: Rattus rattus

<400> SEQUENCE: 26

Met Gly Asp Arg Gly Arg Ser Pro Ser Leu Arg Ser Pro His Gly Ser
1               5                   10                  15

Pro Pro Thr Leu Ser Thr Leu Thr Leu Leu Leu Leu Cys Gly Gln
            20                  25                  30

Ala His Ser Gln Cys Lys Ile Leu Arg Cys Asn Ala Glu Tyr Val Ser
        35                  40                  45

Phe Thr Leu Ser Leu Arg Gly Gly Gly Ser Pro Asp Thr Pro Arg Gly
```

```
                50                  55                  60
Gly Gly Arg Gly Gly Pro Ala Ser Gly Gly Leu Cys Arg Ala Leu Arg
65                  70                  75                  80

Ser Tyr Ala Leu Cys Thr Arg Arg Thr Ala Arg Thr Cys Arg Gly Asp
                85                  90                  95

Leu Ala Phe His Ser Ala Val His Gly Ile Glu Asp Leu Met Ile Gln
            100                 105                 110

His Asn Cys Ser Arg Gln Gly Pro Thr Ala Ser Pro Pro Ala Arg Gly
        115                 120                 125

Pro Ala Leu Pro Gly Ala Gly Pro Ala Pro Leu Thr Pro Asp Pro Cys
    130                 135                 140

Asp Tyr Glu Ala Arg Phe Ser Arg Leu His Gly Arg Thr Pro Gly Phe
145                 150                 155                 160

Leu His Cys Ala Ser Phe Gly Asp Pro His Val Arg Ser Phe His Asn
                165                 170                 175

His Phe His Thr Cys Arg Val Gln Gly Ala Trp Pro Leu Leu Asp Asn
            180                 185                 190

Asp Phe Leu Phe Val Gln Ala Thr Ser Ser Pro Val Ala Ser Gly Ala
        195                 200                 205

Asn Ala Thr Thr Ile Arg Lys Ile Thr Ile Ile Phe Lys Asn Met Gln
    210                 215                 220

Glu Cys Ile Asp Gln Lys Val Tyr Gln Ala Glu Val Asp Asn Leu Pro
225                 230                 235                 240

Ala Ala Phe Glu Asp Gly Ser Val Asn Gly Gly Asp Arg Pro Gly Gly
                245                 250                 255

Ser Ser Leu Ser Ile Gln Thr Ala Asn Leu Gly Ser His Val Glu Ile
            260                 265                 270

Arg Ala Ala Tyr Ile Gly Thr Thr Ile Ile Val Arg Gln Thr Ala Gly
        275                 280                 285

Gln Leu Ser Phe Ser Ile Arg Val Ala Glu Asp Val Ala Arg Ala Phe
    290                 295                 300

Ser Ala Glu Gln Asp Leu Gln Leu Cys Val Gly Gly Cys Pro Pro Ser
305                 310                 315                 320

Gln Arg Leu Ser Arg Ser Glu Arg Asn Arg Arg Gly Ala Ile Ala Ile
                325                 330                 335

Asp Thr Ala Arg Arg Leu Cys Lys Glu Gly Leu Pro Val Glu Asp Ala
            340                 345                 350

Tyr Phe Gln Ser Cys Val Phe Asp Val Ser Val Ser Gly Asp Pro Asn
        355                 360                 365

Phe Thr Val Ala Ala Gln Ser Ala Leu Asp Asp Ala Arg Val Phe Leu
    370                 375                 380

Thr Asp Leu Glu Asn Leu His Leu Phe Pro Val Asp Ala Gly Pro Pro
385                 390                 395                 400

Leu Ser Pro Ala Thr Cys Leu Val Arg Leu Ser Val Leu Phe Val
                405                 410                 415

Leu Trp Phe Cys Ile Gln
            420

<210> SEQ ID NO 27
<211> LENGTH: 366
<212> TYPE: PRT
<213> ORGANISM: Fugu

<400> SEQUENCE: 27

Ala Ser Cys Arg Ile Leu Arg Cys Asn Ser Asp Phe Val Ala Ala Thr
```

```
              1               5              10              15
Leu Asp Leu Gly Ser Ser Ala Gly Ala Gly Gly Ala Pro Leu Ser
                20              25              30

Arg Glu Ala Ala Asn Ala Glu Tyr Cys Arg Ala Leu His Ser Tyr Ser
            35              40              45

Thr Cys Thr Lys Arg Met Ala Arg Pro Cys Arg Gly Asp Leu Ala Tyr
        50              55              60

His Ser Ala Val Gln Gly Ile Glu Asp Leu Leu Ile Gln Tyr Arg Cys
65              70              75              80

Pro Leu Ala Gly Pro Thr Ala Gln Pro Arg Pro Leu Pro Pro Leu Leu
                85              90              95

Ser Gly Asp Val Cys Leu Tyr Asp Arg Arg Leu Ala Ala Glu Ala
                100             105             110

Pro Gln Pro Asp Tyr Leu His Cys Gly Val Phe Gly Asp Pro His Ile
            115             120             125

Arg Thr Phe Asn Asn Asp Phe His Thr Cys Ala Val Gln Gly Ala Trp
        130             135             140

Pro Leu Ile Asp Asn Asp Phe Leu Tyr Val Gln Ala Thr Ser Ser Pro
145             150             155             160

Thr Arg Arg Gly Thr Gln Ala Thr Met Leu Thr Lys Ile Thr Val Ile
                165             170             175

Val Lys Ser Trp Arg His Cys Val Asp Gln Gln Leu Tyr Gln Ala Glu
            180             185             190

Leu Asp Asp Val Pro Met Ala Phe Ala Asp Gly Ser Val Val Ser Gly
        195             200             205

Glu Arg Arg Gly Gln His Thr Leu Ala Ile Thr Gln Ser Pro Gly Arg
    210             215             220

His Ala Glu Ile Arg Ala Ala His Ile Ala Thr Val Ala Ser Gly Gln
225             230             235             240

Ser Gly Arg Ser Leu Ser Leu Ser Val Tyr Ser Pro Arg Ser Val Val
                245             250             255

Glu Ala Phe Gly Pro Glu Gln Asp Leu Gln Leu Cys Met Trp Gly Cys
            260             265             270

Pro Ala Ser Gln Lys Leu Ser Thr Pro Pro Thr Ser Ser Thr Phe
        275             280             285

Ser Ala Ala Val Leu Ala His Cys Asp Ala Leu Leu Pro Val Arg Asp
    290             295             300

Val Tyr His Gln Ala Cys Ile Phe Asp Leu Ile Thr Ser Gly Asp Leu
305             310             315             320

Asn Ser Ser Gly Ala Ala Ile Ser Ala Leu Gln Asp Ala Gln Lys Leu
                325             330             335

Ile Ser Asp Pro Lys Arg Val His Leu Leu Ser Pro Thr Ser Ala Ala
            340             345             350

Gln Arg Glu Asp His Leu Cys Leu Leu Leu Leu Leu Ser
        355             360             365

<210> SEQ ID NO 28
<211> LENGTH: 432
<212> TYPE: PRT
<213> ORGANISM: Chicken

<400> SEQUENCE: 28

Met Gly Arg Gly Ala Gly Ser Thr Ala Leu Gly Leu Phe Gln Ile Leu
1               5              10              15

Pro Val Phe Leu Cys Ile Phe Pro Pro Val Thr Ser Pro Cys Lys Ile
```

```
                    20                  25                  30
Leu Lys Cys Asn Ser Glu Phe Trp Ala Ala Thr Ser Gly Ser His His
                35                  40                  45

Leu Gly Ala Glu Glu Thr Pro Glu Phe Cys Thr Ala Leu Arg Ala Tyr
 50                  55                  60

Ala His Cys Thr Arg Arg Thr Ala Arg Thr Cys Arg Gly Asp Leu Ala
 65                  70                  75                  80

Tyr His Ser Ala Val His Gly Ile Asp Asp Leu Met Val Gln His Asn
                85                  90                  95

Cys Ser Lys Asp Gly Pro Thr Ser Gln Pro Arg Leu Arg Thr Leu Pro
                100                 105                 110

Pro Gly Asp Ser Gln Glu Arg Ser Asp Ser Pro Glu Ile Cys His Tyr
                115                 120                 125

Glu Lys Ser Phe His Lys His Ser Ala Ala Pro Asn Tyr Thr His Cys
                130                 135                 140

Gly Leu Phe Gly Asp Pro His Leu Arg Thr Phe Thr Asp Thr Phe Gln
145                 150                 155                 160

Thr Cys Lys Val Gln Gly Ala Trp Pro Leu Ile Asp Asn Asn Tyr Leu
                165                 170                 175

Asn Val Gln Val Thr Asn Thr Pro Val Leu Pro Gly Ser Ser Ala Thr
                180                 185                 190

Ala Thr Ser Lys Leu Thr Ile Ile Phe Lys Ser Phe Gln Glu Cys Val
                195                 200                 205

Glu Gln Lys Val Tyr Gln Ala Glu Met Asp Glu Leu Pro Ala Ala Phe
210                 215                 220

Ala Asp Gly Ser Lys Asn Gly Asp Lys His Gly Ala Asn Ser Leu
225                 230                 235                 240

Lys Ile Thr Glu Lys Val Ser Gly Gln His Ile Glu Ile Gln Ala Lys
                245                 250                 255

Tyr Ile Gly Thr Thr Ile Val Val Arg Gln Val Gly Arg Tyr Leu Thr
                260                 265                 270

Phe Ala Val Arg Met Pro Glu Glu Val Val Asn Ala Val Glu Asp Arg
                275                 280                 285

Asp Ser Gln Gly Leu Tyr Leu Cys Leu Arg Gly Cys Pro Leu Asn Gln
290                 295                 300

Gln Ile Asp Phe Gln Thr Phe Arg Leu Ala Gln Ala Ala Glu Gly Arg
305                 310                 315                 320

Ala Arg Arg Lys Gly Pro Ser Leu Pro Ala Pro Pro Glu Ala Phe Thr
                325                 330                 335

Tyr Glu Ser Ala Thr Ala Lys Cys Arg Glu Lys Leu Pro Val Glu Asp
                340                 345                 350

Leu Tyr Phe Gln Ser Cys Val Phe Asp Leu Leu Thr Thr Gly Asp Val
                355                 360                 365

Asn Phe Met Leu Ala Ala Tyr Tyr Ala Phe Glu Asp Val Lys Met Leu
                370                 375                 380

His Ser Asn Lys Asp Lys Leu His Leu Tyr Glu Arg Thr Arg Ala Leu
385                 390                 395                 400

Ala Pro Gly Asn Ala Ala Pro Ser Glu His Pro Trp Ala Leu Pro Ala
                405                 410                 415

Leu Trp Val Ala Leu Leu Ser Leu Ser Gln Cys Trp Leu Gly Leu Leu
                420                 425                 430

<210> SEQ ID NO 29
<211> LENGTH: 21
```

```
<212> TYPE: DNA
<213> ORGANISM: Artificial
<220> FEATURE:
<223> OTHER INFORMATION: Polynucleotide replication primer

<400> SEQUENCE: 29
tccaagtcag cgactctctc g                                          21

<210> SEQ ID NO 30
<211> LENGTH: 21
<212> TYPE: DNA
<213> ORGANISM: Artificial
<220> FEATURE:
<223> OTHER INFORMATION: Polynucleotide replication primer

<400> SEQUENCE: 30
tccaagtcag tgactctctc g                                          21

<210> SEQ ID NO 31
<211> LENGTH: 21
<212> TYPE: DNA
<213> ORGANISM: Artificial
<220> FEATURE:
<223> OTHER INFORMATION: Fragment of human HFE2A gene

<400> SEQUENCE: 31
acctgccgcg gggacctcgc c                                          21

<210> SEQ ID NO 32
<211> LENGTH: 21
<212> TYPE: DNA
<213> ORGANISM: Artificial
<220> FEATURE:
<223> OTHER INFORMATION: Fragment of human HFE2A gene containing
      polymorphism

<400> SEQUENCE: 32
acctgccgcg tggacctcgc c                                          21

<210> SEQ ID NO 33
<211> LENGTH: 21
<212> TYPE: DNA
<213> ORGANISM: Artificial
<220> FEATURE:
<223> OTHER INFORMATION: Fragment of human HFE2A gene

<400> SEQUENCE: 33
gcctgggaaa cctggctgga t                                          21

<210> SEQ ID NO 34
<211> LENGTH: 21
<212> TYPE: DNA
<213> ORGANISM: Artificial
<220> FEATURE:
<223> OTHER INFORMATION: Fragment of human HFE2A gene containing
      polymorphism

<400> SEQUENCE: 34
gcctgggaaa gctggctgga t                                          21

<210> SEQ ID NO 35
<211> LENGTH: 21
<212> TYPE: DNA
<213> ORGANISM: Artificial
<220> FEATURE:
<223> OTHER INFORMATION: Fragment of human HFE2A gene

<400> SEQUENCE: 35
```
tcccttctgt ctttagctca t                                          21

<210> SEQ ID NO 36
<211> LENGTH: 21
<212> TYPE: DNA
<213> ORGANISM: Artificial
<220> FEATURE:
<223> OTHER INFORMATION: Fragment of human HFE2A gene containing
      polymorphism

<400> SEQUENCE: 36
tcccttctgt gtttagctca t                                          21

<210> SEQ ID NO 37
<211> LENGTH: 20
<212> TYPE: DNA
<213> ORGANISM: Artificial
<220> FEATURE:
<223> OTHER INFORMATION: Fragment of human HFE2A gene

<400> SEQUENCE: 37
gaggaggagg ccggggtgga                                            20

<210> SEQ ID NO 38
<211> LENGTH: 23
<212> TYPE: DNA
<213> ORGANISM: Artificial
<220> FEATURE:
<223> OTHER INFORMATION: Fragment of human HFE2A gene containing
      polymorphism

<400> SEQUENCE: 38
gaggaggagg aggccggggt gga                                        23

<210> SEQ ID NO 39
<211> LENGTH: 21
<212> TYPE: DNA
<213> ORGANISM: Artificial
<220> FEATURE:
<223> OTHER INFORMATION: Fragment of human HFE2A gene

<400> SEQUENCE: 39
gcctccctgc cccggaccct t                                          21

<210> SEQ ID NO 40
<211> LENGTH: 21
<212> TYPE: DNA
<213> ORGANISM: Artificial
<220> FEATURE:
<223> OTHER INFORMATION: Fragment of human HFE2A gene containing
      polymorphism

<400> SEQUENCE: 40
gcctccctgc gccggaccct t                                          21

<210> SEQ ID NO 41
<211> LENGTH: 21
<212> TYPE: DNA
<213> ORGANISM: Artificial
<220> FEATURE:
<223> OTHER INFORMATION: Fragment of human HFE2A gene

<400> SEQUENCE: 41
atggtcgtcc cccgggggttc t                                         21

<210> SEQ ID NO 42

```
<211> LENGTH: 21
<212> TYPE: DNA
<213> ORGANISM: Artificial
<220> FEATURE:
<223> OTHER INFORMATION: Fragment of human HFE2A gene containing
      polymorphism

<400> SEQUENCE: 42
atggtcgtcc accggggttc t                                              21

<210> SEQ ID NO 43
<211> LENGTH: 21
<212> TYPE: DNA
<213> ORGANISM: Artificial
<220> FEATURE:
<223> OTHER INFORMATION: Fragment of human HFE2A gene

<400> SEQUENCE: 43
cgtcccccgg ggttcttgca t                                              21

<210> SEQ ID NO 44
<211> LENGTH: 21
<212> TYPE: DNA
<213> ORGANISM: Artificial
<220> FEATURE:
<223> OTHER INFORMATION: Fragment of human HFE2A gene containing
      polymorphism

<400> SEQUENCE: 44
cgtcccccgg cgttcttgca t                                              21

<210> SEQ ID NO 45
<211> LENGTH: 21
<212> TYPE: DNA
<213> ORGANISM: Artificial
<220> FEATURE:
<223> OTHER INFORMATION: Fragment of human HFE2A gene

<400> SEQUENCE: 45
gtccaaggag cttggcctct a                                              21

<210> SEQ ID NO 46
<211> LENGTH: 21
<212> TYPE: DNA
<213> ORGANISM: Artificial
<220> FEATURE:
<223> OTHER INFORMATION: Fragment of human HFE2A gene containing
      polymorphism

<400> SEQUENCE: 46
gtccaaggag attggcctct a                                              21

<210> SEQ ID NO 47
<211> LENGTH: 21
<212> TYPE: DNA
<213> ORGANISM: Artificial
<220> FEATURE:
<223> OTHER INFORMATION: Fragment of human HFE2A gene

<400> SEQUENCE: 47
cccccatggc gttgggggcc a                                              21

<210> SEQ ID NO 48
<211> LENGTH: 21
<212> TYPE: DNA
<213> ORGANISM: Artificial
<220> FEATURE:
<223> OTHER INFORMATION: Fragment of human HFE2A gene containing
```

-continued polymorphism

<400> SEQUENCE: 48
cccccatggc tttgggggcc a					21

<210> SEQ ID NO 49
<211> LENGTH: 21
<212> TYPE: DNA
<213> ORGANISM: Artificial
<220> FEATURE:
<223> OTHER INFORMATION: Fragment of human HFE2A gene

<400> SEQUENCE: 49
taagaacatg caggaatgca t					21

<210> SEQ ID NO 50
<211> LENGTH: 21
<212> TYPE: DNA
<213> ORGANISM: Artificial
<220> FEATURE:
<223> OTHER INFORMATION: Fragment of human HFE2A gene containing
      polymorphism

<400> SEQUENCE: 50
taagaacatg aaggaatgca t					21

<210> SEQ ID NO 51
<211> LENGTH: 21
<212> TYPE: DNA
<213> ORGANISM: Artificial
<220> FEATURE:
<223> OTHER INFORMATION: Fragment of human HFE2A gene

<400> SEQUENCE: 51
gccttctcag ctgaacagga c					21

<210> SEQ ID NO 52
<211> LENGTH: 21
<212> TYPE: DNA
<213> ORGANISM: Artificial
<220> FEATURE:
<223> OTHER INFORMATION: Fragment of human HFE2A gene containing
      polymorphism

<400> SEQUENCE: 52
gccttctcag gtgaacagga c					21

<210> SEQ ID NO 53
<211> LENGTH: 21
<212> TYPE: DNA
<213> ORGANISM: Artificial
<220> FEATURE:
<223> OTHER INFORMATION: Fragment of human HFE2A gene

<400> SEQUENCE: 53
agatgctggg gttcctctttt c					21

<210> SEQ ID NO 54
<211> LENGTH: 21
<212> TYPE: DNA
<213> ORGANISM: Artificial
<220> FEATURE:
<223> OTHER INFORMATION: Fragment of human HFE2A gene containing
      polymorphism

<400> SEQUENCE: 54
agatgctggg attcctcttt c					21

-continued

<210> SEQ ID NO 55
<211> LENGTH: 20
<212> TYPE: DNA
<213> ORGANISM: Artificial
<220> FEATURE:
<223> OTHER INFORMATION: Forward replication primer

<400> SEQUENCE: 55
cacttgagcc caggaatttg                                               20

<210> SEQ ID NO 56
<211> LENGTH: 20
<212> TYPE: DNA
<213> ORGANISM: Artificial
<220> FEATURE:
<223> OTHER INFORMATION: Reverse replication primer

<400> SEQUENCE: 56
gactcactgc agccttgacc                                               20

<210> SEQ ID NO 57
<211> LENGTH: 22
<212> TYPE: DNA
<213> ORGANISM: Artificial
<220> FEATURE:
<223> OTHER INFORMATION: Forward replication primer

<400> SEQUENCE: 57
gtgtgctaca agtttgccga at                                            22

<210> SEQ ID NO 58
<211> LENGTH: 20
<212> TYPE: DNA
<213> ORGANISM: Artificial
<220> FEATURE:
<223> OTHER INFORMATION: Reverse replication primer

<400> SEQUENCE: 58
gcttgaaact gggagttgga                                               20

<210> SEQ ID NO 59
<211> LENGTH: 22
<212> TYPE: DNA
<213> ORGANISM: Artificial
<220> FEATURE:
<223> OTHER INFORMATION: Forward replication primer

<400> SEQUENCE: 59
gggaaatggt cccataattc ct                                            22

<210> SEQ ID NO 60
<211> LENGTH: 19
<212> TYPE: DNA
<213> ORGANISM: Artificial
<220> FEATURE:
<223> OTHER INFORMATION: Reverse replication primer

<400> SEQUENCE: 60
cgccctgcca atatgttct                                                19

<210> SEQ ID NO 61
<211> LENGTH: 22
<212> TYPE: DNA
<213> ORGANISM: Artificial
<220> FEATURE:
<223> OTHER INFORMATION: Forward replication primer -continued

<400> SEQUENCE: 61
ggtacttagc ctcgaaatga ga                                                    22

<210> SEQ ID NO 62
<211> LENGTH: 20
<212> TYPE: DNA
<213> ORGANISM: Artificial
<220> FEATURE:
<223> OTHER INFORMATION: Reverse replication primer

<400> SEQUENCE: 62
gtgtcacaca actggttggt                                                       20

<210> SEQ ID NO 63
<211> LENGTH: 1077
<212> TYPE: DNA
<213> ORGANISM: Artificial
<220> FEATURE:
<223> OTHER INFORMATION: Consensus Sequence

<400> SEQUENCE: 63
tctccctctt tgataccatc ttcccctgcc cccccgaacg agcttttttt ttgtgttgta          60
ttgacgagga ggagggattg ttgcacacac tagcgtaatg aaaaggtgg agatagaata          120 gacagctgca gagatctgat ccggacagac agaataaacc ctcctccgaa acaattctgc         180
tctcgggttt cttctccaga cagctggcct ttcggcttct gaaatagttg gcggcgctgg         240
gggcgggtct ctgaactacg cctgccatcc ctcttcaaag ccagctacct ctacgtacca         300
tgtgtggaaa ctcagtggca tcctcagtaa agagaggatg agaacggtga gtgacaggcg         360
tcacacaaat caccaccagc cgtcttacag gccgggagct cattactgag aacgctaaag         420
gacctgagtg gcaggtcata caagctgcag ttggacatgg gacttggcca tcgttctctc         480
tttaggcagt ccctcacttg gtacccagca ttcccatatt ccctctttat tttgctcatc         540
attcctgctg ccttagctcc cacaccctac tgccaccaac gttcctggaa ttttggacct         600
agctattttt aaaactgtca actcaggagg cacctccctc ctcctctcag ctgtccagtg         660
cttgggccaa ccatatactc tccctgcccc ctcccccac accaaagctt cctctggctc          720
tctgacctcg gtgagattgc agccagtccg ggggatcggg gacagacatg agaaggaga         780 tggaggaccc cctggctgga gcagaccaac agaataggca actatggctg gagaaccggg         840
tatcagagta atgcttgacc tcgggaaaca gtaagtctag atgaaatggc ggttgctttg         900
ataagctttt gggtcgaggc tagaatttca taaagttaca gacatctgtt ctgaaaacta        960
agatctctcc ttaccagata ccccaatctt cactttggga ccgcctgctc atacacttat        1020
tccaaagaag ggttttgaca ggagaaaggg agacagaccc ctcccaatat ctgttcc          1077

<210> SEQ ID NO 64
<211> LENGTH: 407
<212> TYPE: PRT
<213> ORGANISM: brare

<400> SEQUENCE: 64

Met Ala Ala Ser Ala Gly Gly Gly Asn His Ser His Thr Thr Trp Arg
1               5                   10                  15

His Ile Val Ile Ile Val Leu Met Val Leu Leu Phe Ser Ala Pro Ser
            20                  25                  30

Val Cys Ala Gln Cys Arg Ile Leu Arg Cys Lys Ser Asp Phe Val Ala
        35                  40                  45

Ala Thr Leu Glu Ser Gly Val Ile Gly Gly Asn Lys Glu Gly Val
 50                  55                  60

Asn Thr Gly Tyr Cys Ser Ala Leu Arg Ser Tyr Ala Leu Cys Thr Gln
 65                  70                  75                  80

Arg Thr Ala Arg Ala Cys Arg Gly Asp Leu Ala Tyr His Ser Ala Val
                 85                  90                  95

Gln Gly Ile Glu Asp Leu Leu Ile Gln Tyr Arg Cys Pro Lys Ala Gly
            100                 105                 110

Pro Thr Ala Gln Pro Gln Pro Arg Pro Leu Pro Gln Ala Pro Leu Ser
        115                 120                 125

Gly Asp Gly Cys Arg Tyr Glu Lys Gly Phe Ile Gln Arg Glu Gly Arg
    130                 135                 140

Ala Pro Glu Tyr Leu His Cys Gly Val Phe Gly Asp Pro His Ile Arg
145                 150                 155                 160

Thr Phe Asn Glu Glu Phe Gln Thr Cys Ala Val Gln Gly Ala Trp Pro
                165                 170                 175

Leu Ile Asp Asn Gln Tyr Leu Tyr Ile Gln Ala Thr Ser Ser Pro Thr
            180                 185                 190

Arg Glu Ser Ser Asp Thr Thr Ile Leu Thr Glu Val Thr Val Ile Phe
        195                 200                 205

Gln Asn Trp Arg Glu Cys Ala Gln Gln Val Tyr Gln Ala Lys Leu Gly
    210                 215                 220

Asn Val Pro Pro Ala Phe Ala Asp Gly Ser Val Thr Gly Gly Asp Arg
225                 230                 235                 240

Arg Gly His Gln Ser Leu Arg Ile His Ser Gln Asp Pro Gly Arg His
                245                 250                 255

Ala Glu Ile Trp Ala Thr His Ile Gly Thr Met Ile Ile Val Arg Gln
            260                 265                 270

Val Gly Gln Ser Leu Ser Leu Ser Val Arg Ser Pro Arg Ala Ile Val
        275                 280                 285

Glu Ser Tyr Thr Pro Glu Gln Asp Leu Gln Leu Cys Val Trp Gly Cys
    290                 295                 300

Pro Ile Ser Gln Arg Leu Glu Met Leu His Ala His Pro Phe Asp Pro
305                 310                 315                 320

Ala Tyr Thr His Cys Ser Ser Leu Phe Pro Gly Arg Asp Val Tyr Phe
                325                 330                 335

Gln Ala Cys Leu Phe Asp Val Gln Val Thr Gly Asp Val Asn Ser Ser
            340                 345                 350

Ala Ser Ala Val Ala Ala Leu Glu Asp Ala Arg Ala Met Ile Ser Asp
        355                 360                 365

Pro Ala Ser Val His Leu Val Thr Gly Thr Gly Asn Asn Ser Pro
370                 375                 380

Ser Leu Leu Val Val Leu Gly Phe Ser Phe Leu Thr Glu Thr Leu Arg
385                 390                 395                 400

His Ser Phe Leu Gly Ser Ala
                405

<210> SEQ ID NO 65
<211> LENGTH: 432
<212> TYPE: PRT
<213> ORGANISM: Homo sapiens

<400> SEQUENCE: 65

Met Gly Arg Gly Ala Gly Arg Ser Ala Leu Gly Phe Trp Pro Thr Leu
 1               5                  10                  15

Ala Phe Leu Leu Cys Ser Phe Pro Ala Ala Thr Ser Pro Cys Lys Ile
            20                  25                  30

Leu Lys Cys Asn Ser Glu Phe Trp Ser Ala Thr Ser Gly Ser His Ala
        35                  40                  45

Pro Ala Ser Asp Asp Thr Pro Glu Phe Cys Ala Ala Leu Arg Ser Tyr
    50                  55                  60

Ala Leu Cys Thr Arg Arg Thr Ala Arg Thr Cys Arg Gly Asp Leu Ala
65                  70                  75                  80

Tyr His Ser Ala Val His Gly Ile Glu Asp Leu Met Ser Gln His Asn
                85                  90                  95

Cys Ser Lys Asp Gly Pro Thr Ser Gln Pro Arg Leu Arg Thr Leu Pro
            100                 105                 110

Pro Ala Gly Asp Ser Gln Glu Arg Ser Asp Ser Pro Glu Ile Cys His
        115                 120                 125

Tyr Glu Lys Ser Phe His Lys His Ser Ala Thr Pro Asn Tyr Thr His
    130                 135                 140

Cys Gly Leu Phe Gly Asp Pro His Leu Arg Thr Phe Thr Asp Arg Phe
145                 150                 155                 160

Gln Thr Cys Lys Val Gln Gly Ala Trp Pro Leu Ile Asp Asn Asn Tyr
                165                 170                 175

Leu Asn Val Gln Ala Thr Asn Thr Pro Val Leu Pro Gly Ser Ala Ala
            180                 185                 190

Thr Ala Thr Ser Lys Leu Thr Ile Ile Phe Lys Asn Phe Gln Glu Cys
        195                 200                 205

Val Asp Gln Lys Val Tyr Gln Ala Glu Met Asp Glu Leu Pro Ala Ala
    210                 215                 220

Phe Val Asp Gly Ser Lys Asn Gly Gly Asp Lys His Gly Ala Asn Ser
225                 230                 235                 240

Leu Lys Ile Thr Glu Lys Val Ser Gly Gln His Val Glu Ile Gln Ala
                245                 250                 255

Lys Tyr Ile Gly Thr Thr Ile Val Val Arg Gln Val Gly Arg Tyr Leu
            260                 265                 270

Thr Phe Ala Val Arg Met Pro Glu Glu Val Val Asn Ala Val Glu Asp
        275                 280                 285

Trp Asp Ser Gln Gly Leu Tyr Leu Cys Leu Arg Gly Cys Pro Ile Asn
    290                 295                 300

Gln Gln Ile Asp Phe Gln Ala Phe His Thr Asn Ala Glu Gly Thr Gly
305                 310                 315                 320

Ala Arg Arg Leu Ala Ala Ala Ser Pro Ala Pro Thr Ala Pro Glu Thr
                325                 330                 335

Phe Pro Tyr Glu Thr Ala Val Ala Lys Cys Lys Glu Lys Leu Pro Val
            340                 345                 350

Glu Asp Leu Tyr Tyr Gln Ala Cys Val Phe Asp Leu Leu Thr Thr Gly
        355                 360                 365

Asp Val Asn Phe Thr Leu Ala Ala Tyr Tyr Ala Leu Glu Asp Val Lys
    370                 375                 380

Met Leu His Ser Asn Lys Asp Lys Leu His Leu Tyr Glu Arg Thr Arg
385                 390                 395                 400

Asp Leu Pro Gly Arg Ala Ala Ala Gly Leu Pro Leu Ala Pro Arg Pro
                405                 410                 415

Leu Leu Gly Ala Leu Val Pro Leu Leu Ala Leu Leu Pro Val Phe Cys
            420                 425                 430

<210> SEQ ID NO 66

<211> LENGTH: 437
<212> TYPE: PRT
<213> ORGANISM: Homo sapiens

<400> SEQUENCE: 66

```
Met Gly Leu Arg Ala Ala Pro Ser Ser Ala Ala Ala Ala Ala Ala Glu
1               5                   10                  15

Val Glu Gln Arg Arg Ser Pro Gly Leu Cys Pro Pro Leu Glu Leu
            20                  25                  30

Leu Leu Leu Leu Leu Phe Ser Leu Gly Leu Leu His Ala Gly Asp Cys
            35                  40                  45

Gln Gln Pro Ala Gln Cys Arg Ile Gln Lys Cys Thr Thr Asp Phe Val
50                  55                  60

Ser Leu Thr Ser His Leu Asn Ser Ala Val Asp Gly Phe Asp Ser Glu
65                  70                  75                  80

Phe Cys Lys Ala Leu Arg Ala Tyr Ala Gly Cys Thr Gln Arg Thr Ser
                85                  90                  95

Lys Ala Cys Arg Gly Asn Leu Val Tyr His Ser Ala Val Leu Gly Ile
            100                 105                 110

Ser Asp Leu Met Ser Gln Arg Asn Cys Ser Lys Asp Gly Pro Thr Ser
        115                 120                 125

Ser Thr Asn Pro Glu Val Thr His Asp Pro Cys Asn Tyr His Ser His
130                 135                 140

Ala Gly Ala Arg Glu His Arg Arg Gly Asp Gln Asn Pro Pro Ser Tyr
145                 150                 155                 160

Leu Phe Cys Gly Leu Phe Gly Asp Pro His Leu Arg Thr Phe Lys Asp
                165                 170                 175

Asn Phe Gln Thr Cys Lys Val Glu Gly Ala Trp Pro Leu Ile Asp Asn
            180                 185                 190

Asn Tyr Leu Ser Val Gln Val Thr Asn Val Pro Val Val Pro Gly Ser
        195                 200                 205

Ser Ala Thr Ala Thr Asn Lys Ile Thr Ile Ile Phe Lys Ala His His
210                 215                 220

Glu Cys Thr Asp Gln Lys Val Tyr Gln Ala Val Thr Asp Asp Leu Pro
225                 230                 235                 240

Ala Ala Phe Val Asp Gly Thr Thr Ser Gly Gly Asp Ser Asp Ala Lys
                245                 250                 255

Ser Leu Arg Ile Val Glu Arg Glu Ser Gly His Tyr Val Glu Met His
            260                 265                 270

Ala Arg Tyr Ile Gly Thr Thr Val Phe Val Arg Gln Val Gly Arg Tyr
        275                 280                 285

Leu Thr Leu Ala Ile Arg Met Pro Glu Asp Leu Ala Met Ser Tyr Glu
290                 295                 300

Glu Ser Gln Asp Leu Gln Leu Cys Val Asn Gly Cys Pro Leu Ser Glu
305                 310                 315                 320

Arg Ile Asp Asp Gly Gln Gly Gln Val Ser Ala Ile Leu Gly His Ser
                325                 330                 335

Leu Pro Arg Thr Ser Leu Val Gln Ala Trp Pro Gly Tyr Thr Leu Glu
            340                 345                 350

Thr Ala Asn Thr Gln Cys His Glu Lys Met Pro Val Lys Asp Ile Tyr
        355                 360                 365

Phe Gln Ser Cys Val Phe Asp Leu Leu Thr Thr Gly Asp Ala Asn Phe
370                 375                 380

Thr Ala Ala Ala His Ser Ala Leu Glu Asp Val Glu Ala Leu His Pro
385                 390                 395                 400
```

```
Arg Lys Glu Arg Trp His Ile Phe Pro Ser Ser Gly Asn Gly Thr Pro
                405                 410                 415
Arg Gly Gly Ser Asp Leu Ser Val Ser Leu Gly Leu Thr Cys Leu Leu
            420                 425                 430
Leu Ile Val Phe Leu
        435

<210> SEQ ID NO 67
<211> LENGTH: 93
<212> TYPE: PRT
<213> ORGANISM: Homo sapiens

<400> SEQUENCE: 67

Cys Ser Val Ser Gly Asp Gly His Tyr Thr Thr Phe Asp Gly Arg Lys
1               5                   10                  15
Tyr Thr Phe Pro Gly Asn Cys Thr Tyr Val Leu Ala Gln Asp Cys Thr
            20                  25                  30
Ser Glu Pro Ser Phe Ser Val Leu Leu Lys Asn Val Asn Cys Gly Gly
        35                  40                  45
Asp Ala Thr Cys Leu Lys Ser Val Lys Val Glu Leu Asn Asp Ile Glu
    50                  55                  60
Ile Glu Leu Lys Asp Asp Gly Gly Lys Val Thr Val Asn Gly Gln Lys
65                  70                  75                  80
Val Ser Leu Pro Tyr Lys Thr Ser Asp Gly Ser Ile Arg
                85                  90

<210> SEQ ID NO 68
<211> LENGTH: 9
<212> TYPE: PRT
<213> ORGANISM: Chicken

<400> SEQUENCE: 68

Phe Gly Asp Pro His Leu Arg Thr Phe
1               5

<210> SEQ ID NO 69
<211> LENGTH: 1320
<212> TYPE: DNA
<213> ORGANISM: Homo sapiens

<400> SEQUENCE: 69
atgggggagc caggccagtc ccctagtccc aggtcctccc atggcagtcc cccaactcta     60
agcactctca ctctcctgct gctcctctgt ggacatgctc attctcaatg caagatcctc    120
cgctgcaatg ctgagtacgt atcgtccact ctgagcctta aggtgggggg ttcatcagga    180
gcacttcgag gaggaggagg aggaggccgg ggtggagggg tgggctctgg cggcctctgt    240
cgagccctcc gctcctatgc gctctgcact cggcgcaccg cccgcacctg ccgcggggac    300
ctcgccttcc attcggcggt acatggcatc gaagacctga tgatccagca caactgctcc    360
cgccagggcc ctacagcccc tcccccgccc cggggcccg ccccttccagg cgcgggctcc    420
ggcctccctg ccccggaccc ttgtgactat gaaggccggt tttcccggct gcatggtcgt    480
cccccggggt tcttgcattg cgcttccttc ggggaccccc atgtgcgcag cttccaccat    540
cactttcaca catgccgtgt ccaaggagct tggcctctac tggataatga cttcctcttt    600
gtccaagcca ccagctcccc catggcgttg ggggccaacg ctaccgccac ccggaagctc    660
accatcatat ttaagaacat gcaggaatgc attgatcaga aggtgtatca ggctgaggtg    720
gataatcttc ctgtagcctt tgaagatggt tctatcaatg gaggtgaccg acctggggga    780
```

```
tccagtttgt cgattcaaac tgctaaccct gggaaccatg tggagatcca agctgcctac    840
attggcacaa ctataatcat tcggcagaca gctgggcagc tctccttctc catcaaggta    900
gcagaggatg tggccatggc cttctcagct gaacaggacc tgcagctctg tgttgggggg    960
tgccctccaa gtcagcgact ctctcgatca gagcgcaatc gtcggggagc tataaccatt   1020
gatactgcca gacggctgtg caaggaaggg cttccagtgg aagatgctta cttccattcc   1080
tgtgtctttg atgttttaat ttctggtgat cccaacttta ccgtggcagc tcaggcagca   1140
ctggaggatg cccgagcctt cctgccagac ttagagaagc tgcatctctt cccctcagat   1200
gctggggttc ctctttcctc agcaaccctc ttagctccac tcctttctgg gctctttgtt   1260
ctgtggcttt gcattcagta aggggaccat cagtcccatt actagtttgg aaatgatttg   1320
```

<210> SEQ ID NO 70
<211> LENGTH: 4
<212> TYPE: PRT
<213> ORGANISM: Homo sapiens

<400> SEQUENCE: 70

Arg Asn Arg Arg
1

<210> SEQ ID NO 71
<211> LENGTH: 4
<212> TYPE: PRT
<213> ORGANISM: Artificial
<220> FEATURE:
<223> OTHER INFORMATION: Consensus sequence
<220> FEATURE:
<221> NAME/KEY: misc_feature
<222> LOCATION: (2)
<223> OTHER INFORMATION: Xaa can be any naturally occurring amino acid
<220> FEATURE:
<221> NAME/KEY: misc_feature
<222> LOCATION: (3)
<223> OTHER INFORMATION: Xaa can be Lys or Arg

<400> SEQUENCE: 71

Arg Xaa Xaa Arg
1

JUVENILE HEMOCHROMATOSIS GENE (HFE2A), EXPRESSION PRODUCTS AND USES THEREOF This patent application is a continuation of U.S. application Ser. No. 10/552,158, now abandoned a 371 National Phase filing of International Application PCT/CA2004/000522, filed 8 Apr. 2004, which claims priority of U.S. provisional applications Ser. No. 60/462,867, filed 15 Apr. 2003, Ser. No. U.S. 60/488,607, filed 18 Jul. 2003, and Ser. No. 60/498,458, filed 28 Aug. 2003, the disclosures of all of which are hereby incorporated by reference in their entirety.

FIELD OF THE INVENTION

The present invention relates generally to the field of iron metabolism diseases, especially juvenile hemochromatosis, to a gene associated therewith, and to methods of using this gene, including expression products thereof, for the screening and identification of agents useful in the treatment of diseases of iron metabolism, including methods of such treatment.

BACKGROUND OF THE INVENTION

At least 4 iron-overload disorders labeled hemochromatosis have been identified on the basis of clinical, biochemical, and genetic characteristics. Hemochromatosis type 1 is classic hemochromatosis (sometimes designated "HFE") (see OMIM Number: 235200; Online Mendelian Inheritance in Man, OMIM™. Johns Hopkins University, Baltimore, Md., at www.ncbi.nlm.nih.gov/omim/), an autosomal recessive disorder, which is caused by mutation in a gene designated HFE on chromosome 6p21.3. The medical disorder called juvenile hemochromatosis (sometimes called "JH" or "juvenile haemochromatosis"), is also known as hemochromatosis type 2 ("HFE2"). Hemochromatosis type 3 (HFE3; OMIM 604250), an autosomal recessive disorder, is caused by mutation in the gene encoding transferrin receptor-2 (TFR2; OMIM 604720), which maps to 7q22. Hemochromatosis type 4 (HFE4; OMIM 606069), an autosomal dominant disorder, is caused by mutation in the SLC11A3 gene (OMIM 604653), which encodes ferroportin and maps to 2q32.

In some families juvenile hemochromatosis shows linkage to chromosome 1q21, whereas in others it is caused by mutation in the gene encoding hepcidin antimicrobial peptide, which maps to chromosome 19q13.

The two forms of juvenile hemochromatosis (HFE2) are tentatively designated HFE2A and HFE2B, respectively. The present invention relates to the genetic basis of HFE2A, the form of JH linked to chromosome 1q21.

Juvenile hemochromatosis (JH) differs from typical hereditary hemochromatosis. While HFE has a prevalent male expression, JH affects both sexes equally. JH involves iron accumulation, which begins early in life and typically causes clinical symptoms before the age of 30 years. JH is a more severe disease than typical hereditary hemochomotosis, with JH showing hypogonadotropic hypogonadism, heart failure, arrhythmias and/or cardiomyopathy as frequent features. If untreated, the disease is lethal because of cardiac and other complications.

Identification of 1q21 as the chromosomal location of HFE2A was first reported in Roetto et al., *Am. J. Hum. Genet.* 64:1388-1393 (1999) but this locus did not correspond to the chromosomal location of any known gene involved in iron metabolism.

The present invention provides identification of the hereditary basis for HFE2A, thereby facilitating development of more potent agents for treating diseases of iron metabolism. Administration of the HFE2A gene or protein itself may be therapeutic. Alternatively, the underlying genetic mutation identifies a novel therapeutic target for treating diseases of iron metabolism. This therapeutic target can be used to identify and discover more effective therapeutic agents. Diagnostic compounds, kits and methods using HFE2A are also included which may be used to diagnose JH as well as to diagnose and predict onset and severity of adult hemochromatosis and to distinguish between types of iron metabolism disorders.

BRIEF SUMMARY OF THE INVENTION

The invention relates to the discovery that juvenile hemochromatosis (hemochromatosis type 2A, or HFE2A), is caused by a mutation in a human gene found at 1q22 having the nucleotide sequence as set out in SEQ ID Nos. 1-9, and/or the corresponding amino acid sequences as set out in SEQ ID Nos. 10-12. The gene and the protein are referred to herein as HFE2A and also as hemojuvelin, these words referring the gene, the gene product and the protein expressed therefrom, unless the context specifies otherwise. The gene has also been named HFE2, by which is meant the form JH caused by the gene at 1q21. This naming protocol is not essential to the invention claimed herein.

In one aspect, the present invention relates to a method for identifying an agent that modulates hemojuvelin, comprising contacting a test compound with hemojuvelin and determining a change in hemojuvelin activity due to the compound, thereby identifying a modulator of the type being sought. The modulator may be a drug-like small molecule, an antibody, an antisense nucleic acid, a ribozyme or any other compound which changes the activity of the gene or protein.

In one aspect, the present invention relates to method for identifying an agent that modulates HFE2A gene expression, comprising contacting a test compound with a polynucleotide comprising a HFE2A gene and under conditions promoting expression of said gene (i.e., conditions wherein the polynucleotide is being expressed) and determining a change in expression due to the presence of the test compound. This identifies the test compound as such a modulator. In a preferred embodiment, this change in expression is detected as a change in transcription of the gene, preferably where the gene is a mammalian gene and most preferably where the gene is expressed by a cell.

In another aspect, the present invention relates to a method for identifying an agent that modulates HFE2A gene expression, comprising contacting a test compound with a reporter gene operably linked to a promoter sequence and determining a change in expression of the reporter gene due to the test compound, thus identifying a modulator of the construct. Preferably, this is modulation of transcription of said reporter gene operably linked to an HFE2A promoter, most preferably a mammalian HFE2A, such as a mouse, rat or human HFE2A promoter.

In a further aspect, the present invention relates to a method for treating and/or preventing a disorder in an animal comprising administering to an animal afflicted therewith, or at risk of developing said disorder, a therapeutically effective amount of an HFE2A modulator. In a preferred embodiment, the HFE2A modulator exhibits modulating activity in a method of the invention, most preferably wherein said agent was first identified as an HFE2A modulator using said method and was not otherwise known to have such activity.

In a yet further aspect, the present invention relates to a method to diagnose individuals afflicted with or at risk of developing HFE2A or a related disorder comprising determining the nucleic acid sequence of the HFE2A gene in said individual wherein a mutation or polymorphism of said gene identifies said individual as an individual afflicted with or at risk of developing HFE2A or a related disorder.

The present invention also contemplates a method for identifying a compound capable of modulating a HFE2A activity, comprising: (a) contacting a cell which expresses HFE2A with a test compound; and (b) assaying the ability of the test compound to modulate the transcription of a HFE2A nucleic acid or the activity of HFE2A polypeptide, thereby identifying a compound capable of modulating a HFE2A activity. In a preferred embodiment of such method, the compound is an anti-HFE2A polypeptide antibody, a ribozyme or is an antisense HFE2A nucleic acid molecule. In one preferred embodiment thereof, the compound is a HFE2A ribozyme.

The present invention also encompasses an isolated polynucleotide or isolated polypeptide of the genes disclosed herein.

BRIEF DESCRIPTION OF THE DRAWINGS

FIG. 7(d) shows the identification of partial von Willebrand Type D domain (SEQ ID NO: 67-57%) using NCBI Conserved Domain Search. (LOC148738=HFE2A—amino acids 167 to 253 of SEQ ID NO: 12); FIG. 7(e) shows Possible proteolytic cleavage site (arrow) between residues 172D and 173P (of SEQ ID NO: 12) identified by sequence comparison with Chicken Repulsive Guidance Molecule (RGM—SEQ ID NO: 68).

FIG. 8 shows nucleic acid (SEQ ID NO: 69) and amino-acid (SEQ ID NO: 12) sequence of 426 aa open-reading frame translated from Transcript4 of LOC148738 (Protein3). This protein is identical to the Ensembl protein ENSP00000304614 from the predicted Ensembl transcript ENST00000306561. Box, initiating codon; triangle, potential signal peptide cleavage site; dots, RGD site; cross, predicted O-glycosylation sites (NetOGlyc2.0 predicted); diamonds, predicted N-glycosylation sites (NetNGlyc 1.0 predicted); arrow, putative cleavage site from comparison with chicken RGM; double arrow, furin cleavage site; square, predicted GPI anchor modification site; asterix, stop codon.

DETAILED DESCRIPTION OF THE INVENTION

Figure 1:
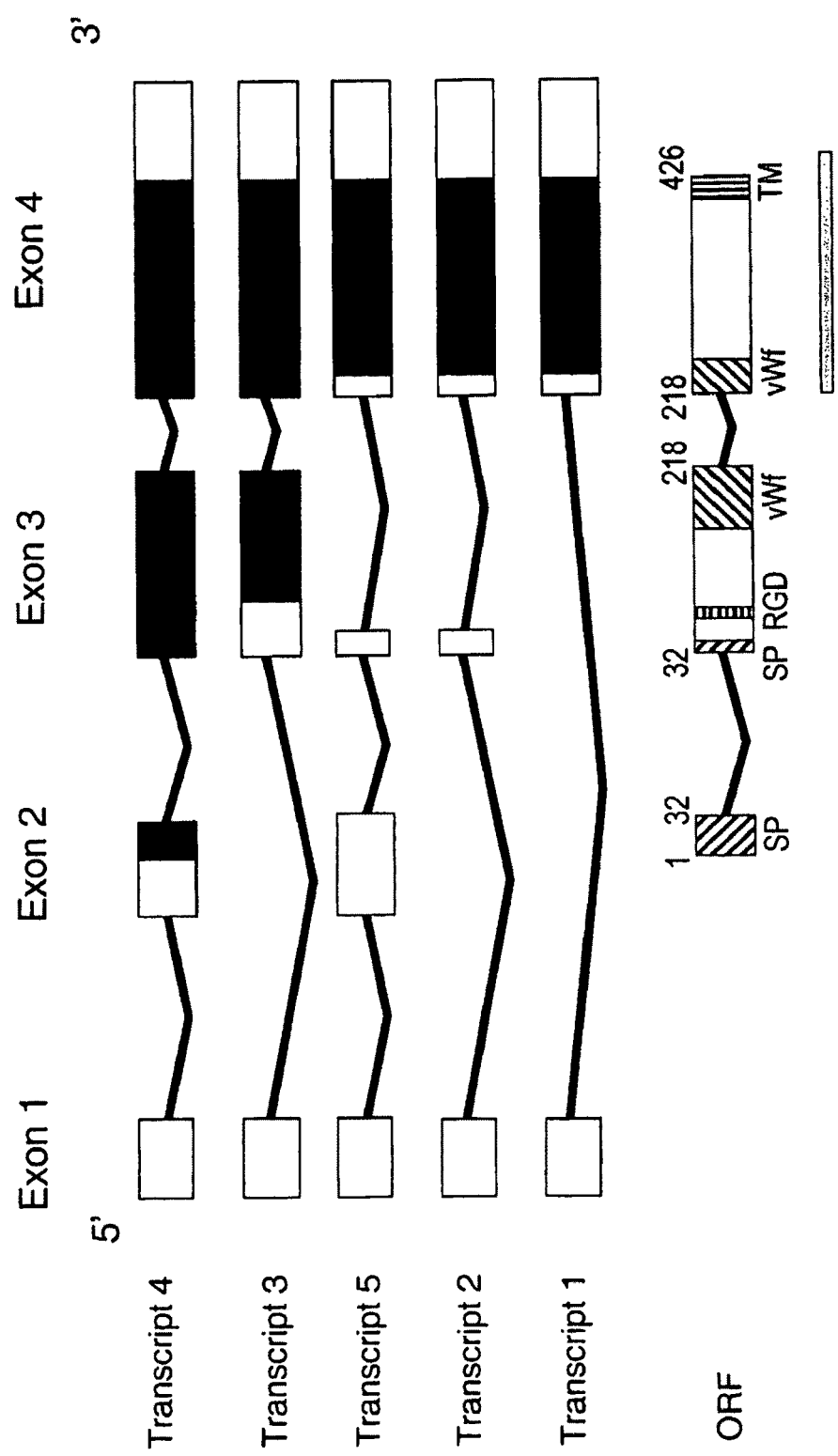
FIG. 1 is a schematic of LOC148738 Gene structure. The LOC148738 Gene has four exons and five transcripts. The five transcripts code for 3 proteins of 200 AA, 313 AA and 426 AA. Exon 2 was predicted by Ensembl from cDNA sequence AK098165.1. The acceptor site for Exon 2 is inferred from the genomic sequence. Exons 3a and 3b have the same acceptor site but different donor sites. Untranslated sequence is white, translated sequence is black. The transcripts are listed from longest to shortest.

The present invention provides a gene and its corresponding protein related to diseases of iron metabolism, referred to as hemojuvelin or HFE2A. Hemojuvelin and HFE2A refers to both the gene, the gene product and the protein expressed therefrom, unless the context specifies otherwise.

In accordance with the present invention, the human HFE2A gene is disclosed. This gene, when mutated, results in juvenile hemochromatosis (hemochromatosis type 2A). The gene has also been named HFE2, by which is meant the form JH caused by the gene at 1q21. The gene product/protein is also sometimes called "hemojuvelin". This naming protocol is not essential to the invention claimed herein.

In one aspect, the invention relates to the nucleic acid sequence for HFE2A, including the genomic sequence, mRNA or cDNA, polymorphic, allelic, isoforms (adult, neonatal, etc.) and mutant forms thereof, and nucleic acid constructs of the gene, including vectors, plasmids and recombinant cells and transgenic organisms containing or corresponding to HFE2A (or knock-outs thereof). Such nucleic acid sequences are set forth in SEQ. ID NOS. 1-9, and 13-22.

In another aspect, the invention relates to the gene product of HFE2A, sometimes called herein hemojuvelin or HFE2A polypeptide, including the polypeptide, protein, and amino acid sequence, and the polymorphic, allelic, isoforms (adult, neo-natal, etc.) and mutant forms thereof, mRNA or other transcripts of HFE2A, and recombinant cells and transgenic organisms wherein this polypeptide or a polypeptide corresponding thereto is expressed. Such amino acid sequences are set forth in SEQ. ID NOs: 10-12 and 23-28.

In one aspect of the present invention, HFE2A is incorporated into a screening assay whereby compounds (potential therapeutic agents) are tested to determine if they modulate HFE2A gene expression activity, thereby identifying potential therapeutic agents.

In accordance with the foregoing, the present invention relates to method for identifying an agent that modulates HFE2A gene expression, comprising:
a) contacting a test compound with a cell expressing an HFE2A gene;
b) determining a change in expression of said HFE2A gene as a result of said contacting,
wherein a change in expression identifies said test compound as an agent that modulates HFE2A gene expression.

In a preferred embodiment, this change in expression is detected by detecting a change in transcription of said gene, such as where there is a decrease or increase in transcription. In another preferred embodiment, the HFE2A gene is a mammalian HFE2A gene, most preferably where the mammal is a mouse, rat or human.

In another preferred embodiment, the gene whose modulation is to be determined is present in a mammalian cell, preferably a recombinant cell, including where the cell is a macrophage, inflammatory cell, liver cell, hepatocyte, intestinal cell, hematopoietic cell, pancreatic cell, skeletal muscle cell or a cell of the nervous system.

In another aspect, the present invention relates to a method for identifying an agent that modulates the activity of an HFE2A polypeptide, comprising:
a) contacting a test compound with an HFE2A polypeptide and under conditions supporting an activity of said polypeptide; and
b) determining a change in said activity of said polypeptide as a result of said contacting,
wherein a change in the activity identifies said test compound as an agent that modulates the activity of an HFE2A polypeptide.

In preferred embodiments of such methods, the HFE2A-encoded polypeptide is a mammalian HFE2A polypeptide, most preferably from mouse, rat or human.

In other preferred embodiments, the modulation is a decrease or increase in said biological activity. In a highly useful embodiment, the polypeptide is in, or is part of, a cell, preferably a mammalian cell, most preferably a recombinant cell, including where the cell is a macrophage, inflammatory cell, liver cell, hepatocyte, intestinal cell, hematopoietic cell, pancreatic cell, skeletal muscle cell or a cell of the nervous system. In other preferred embodiments, the cell has been engineered to contain said polypeptide, such as by genetic engineering, especially where said cell does not express said polypeptide absent said engineering.

In an additional preferred embodiment, the polypeptide is encoded by a polynucleotide having the sequence selected from the group consisting of SEQ ID NO: 1, 2, 3, 4, 5, 6, 7, 8 and 9, most preferably wherein said polypeptide comprises an amino acid sequence selected from the sequence of SEQ ID NO: 10, 11 and 12.

The present invention also relates to a cell line comprising a one or more of said polynucleotides of SEQ ID NO: 1, 2, 3, 4, 5, 6, 7, 8 and 9, including recombinant forms of the polynucleotides, as well as a cell line comprising one or more of the polypeptides of SEQ ID NO: 10, 11 and 12, preferably a recombinant form of the polypeptide. In another embodiment, the present invention relates to use of such a cell line in a method for identifying compositions which modulate expression or activity of hemojuvelin.

In a further aspect, the present invention relates to a method for treating and/or preventing a disorder in an animal comprising administering to an animal afflicted therewith, or at risk of developing said disorder, a therapeutically effective amount of an HFE2A modulator. In a preferred embodiment, the HFE2A modulator exhibits modulating activity in a method of the invention, most preferably wherein said agent was first identified as an HFE2A modulator using said method and was not otherwise known to have such activity. In a preferred embodiment of such method, the HFE2A modulator is a selective HFE2A agonist, or a selective HFE2A antagonist, including pharmaceutically acceptable salts thereof, and/or any combinations of these, including where these are in a pharmaceutically acceptable carrier. In an embodiment, said disorder is a disease of iron metabolism, including an iron overload disorder and/or an iron deficiency disorder. Such disease of iron metabolism may also include one or more of Type I diabetes, Type II diabetes and insulin resistance.

In a yet further aspect, the present invention relates to a method to diagnose individuals afflicted with or at risk of developing HFE2A or a related disorder comprising determining all or part of the nucleic acid sequence of the HFE2A gene in said individual wherein a mutation or polymorphism of said gene identifies said individual as an individual afflicted with or at risk of developing HFE2A or a related disorder. In another such embodiment, the present invention relates to a method to diagnose individuals affected by or at risk of developing HFE2A or a related disorder comprising determining all or part of the amino acid sequence of HFE2A polypeptide in said individual wherein a mutation or polymorphism of said gene identifies said individual as an individual affected by or at risk of developing HFE2A or a related disorder.

The present invention also contemplates a method for identifying a compound capable of modulating a HFE2A activity, comprising: (a) contacting a cell which expresses HFE2A with a, test compound; and (b) assaying the ability of the test compound to modulate the transcription of a HFE2A nucleic acid or the activity of HFE2A Polypeptide, thereby identifying a compound capable of modulating a HFE2A activity. In a preferred embodiment of such method, the compound is an anti-HFE2A polypeptide antibody, a ribozyme or is an antisense HFE2A nucleic acid molecule. In one preferred embodiment thereof, the compound is a HFE2A ribozyme. In another embodiment, the compound is a small organic molecule.

The present invention also encompasses an isolated polynucleotide comprising a polynucleotide having a nucleotide sequence with at least 60 percent identity to a sequence selected from the group consisting of SEQ ID NO: 1, 2, 3, 4, 5, 6, 7, 8, 9, 19, 20, 21 and 22. In other embodiments thereof, said percent identity is at least 70 percent, more preferably at least 78 percent, even more preferably at least 90 percent, yet more preferably at least 95 percent, still more preferably at least 98 percent, and most preferably where the nucleotide sequence is a member selected from the group consisting of SEQ ID NO: 1, 2, 3, 4, 5, 6, 7, 8, 9, 19, 20, 21 and 22.

In another such embodiment, the present invention specifically encompasses an isolated polypeptide comprising a polypeptide having an amino acid sequence with at least 90 percent identity to an amino acid sequence selected from the group consisting of SEQ ID NO: 10, 11, 12, 23, 24, 25, 26, 27 and 28, preferably at least 95 percent, more preferably at least 98 percent and most preferably where the amino acid sequence is selected from the group consisting of SEQ ID NO: 10, 11, 12, 23, 24, 25, 26, 27 and 28.

The present invention also encompasses embodiments where the agents identified by the methods of the invention, or useful in the methods of the invention, may be present in the form of a composition for treating a disease of iron metabolism comprising a therapeutically effective amount of a polypeptide of the invention, or a pharmaceutically active fragment thereof, in a pharmaceutically acceptable carrier. In accordance therewith, the present invention specifically contemplates a method for treating a disease of iron metabolism comprising administering to a patient in need thereof a therapeutically effective amount of such a composition. In an embodiment thereof, the disease is juvenile hemochromatosis.

In a further aspect, the present invention relates to a method for identifying an agent for the treatment of a disease of iron metabolism, comprising:

a) administering to an animal an agent found to have activity using a method as disclosed herein, and b) detecting in said animal a change which is indicative of a change in iron metabolism due to said administering, thereby identifying an agent for the treatment a disease of iron metabolism.

Preferably, the animal is a mammal, such as a human being. In specific embodiments, the change in iron metabolism may be a change in storage tissue distribution of iron.

In a preferred embodiment of the invention, the compound identified which modulates HFE2A is selective for HFE2A ahead of related genes or proteins, and therefore does not significantly modulate the activity of such other related genes or proteins by direct interaction.

In a further aspect, the present invention relates to a method for treating a condition in an animal afflicted with a disease of iron metabolism comprising administering to said animal an effective amount of an agent first identified by an assay method of the invention. Preferably, said animal is a human patient, such as a patient afflicted with a chronic disease of iron metabolism.

In a further aspect, the compounds identified by the assays disclosed herein, and the methods of treating patients with such compounds, are applied to alternative or additional indications beyond diseases of iron metabolism, which are found to be treatable by modulating HFE2A activity.

In a further aspect, the present invention relates to compounds that modulate HFE2A that may now be identified by those skilled in the art. These compounds include antibodies, antisense compounds, gene therapy vectors and proteins, and small molecule organic compounds. The invention also comprises the use of these compounds for treatment of diseases associated with aberrant HFE2A activity. In one embodiment, the use of the compounds for treatment of disease of iron metabolism.

In another aspect, the present invention relates to a method for producing a product comprising identifying an agent according to the process of the invention wherein said product is the data collected with respect to said agent as a result of said process and wherein said data is sufficient to convey the chemical structure and/or properties of said agent.

In another aspect, the present invention relates to diagnostic and pharmacogenomic compositions, kits and methods which identify the presence or absence in a patient of one or more mutations in a polynucleotide or a polypeptide corresponding to SEQ ID NOs: 1-12, including those specific mutations identified at SEQ ID NOs 14, 16, and 18, and other mutations that may be subsequently discovered to be relevant. This embodiment is useful in diagnosing the presence or absence of juvenile hemochromatosis. It is also useful for diagnosis of adult onset hemochromatosis, and for the prediction of onset and severity thereof.

FIG. 1 illustrates alternative splice variants that are generated during transcription of the HFE2A gene. For convenience, the nucleotide sequences of the coding exons are set out as follows:

| SEQ ID NO. | Description |
| --- | --- |
| 1 | Sequence of Exon 1 |
| 2 | Sequence of Exon 2 |
| 3 | Sequence of Exon 3a |
| 4 | Sequence of Exon 3b |
| 5 | Sequence of Exon 4 |

The alternative splice variants generated from the gene produce at least 5 transcripts. The nucleotide sequence of each of transcripts 1 to 4, corresponding to a cDNA sequence (or a processed mRNA sequence if T is converted to U) is set out as follows:

| SEQ ID NO. | Description |
| --- | --- |
| 6 | Wild-Type Human HFE2A putative cDNA - Transcript 1 (exon 1, 4) |
| 7 | Wild-Type Human HFE2A putative cDNA - Transcript 2 (exon 1, 3a, 4) |
| 8 | Wild-Type Human HFE2A putative cDNA - Transcript 3 (exon 1, 3b, 4) |
| 9 | Wild-Type Human HFE2A putative cDNA - Transcript 4 (exon 1, 2, 3b, 4) |

Each of these four transcripts of the HFE2A gene may be translated into an HFE2A polypeptide. Transcripts 1 and 2 generate the same full length proteins, hence there are 3 full-length proteins of 200 amino acids (a.a.), 313 a.a. and 426 a.a., respectively. The amino acid sequence generated from each transcript is set out as follows:

| SEQ ID NO. | Description |
| --- | --- |
| 10 | Wild-Type Human HFE2A Polypeptide - Protein 1 (Transcripts 1 & 2) |
| 11 | Wild-Type Human HFE2A Polypeptide - Protein 2 (Transcript 3) |
| 12 | Wild-Type Human HFE2A Polypeptide - Protein 3 (Transcript 4) |

The longest cDNA sequence (Transcript 4, SEQ ID No. 9) and the longest protein sequence (Protein 3, SEQ ID No. 12) have been used as the basis for the sequencing numbering convention used in the instant specification.

Aspects of the sequence of HFE2A have been previously published in various sources, including the following: *Homo sapiens* Official Gene Symbol and Name: LOC148738; NCBI LocusID: 148738; Other Names: ENSG00000168509 (Ensembl v. 12.31.1), NM_145277 (RefSeq); Genomic Location: 142000393-142004657 bp on chromosome 1 (Assembly: NCBI 31 assembly of the human genome, Freeze Date: November 2002) (Ensembl Version for reference sequences: Ensembl v. 12.31.1.) An incomplete fragment of HFE2A is contained in PCT publication WO 02/051438 where it was listed as RGM3 and implicated as a Repulsive Guidance Molecule in neuronal development (3 amino acids, 9 nt missing from 5' coding end).

A positional cloning strategy, set out in Example 1 below, was used to confirm that chromosomal region 1q21 was highly associated with juvenile hemochromatosis. Candidate genes were investigated to determine if mutations were present. The HFE2A gene described herein was determined to contain a variety of deleterious mutations as follows:

TABLE 1

| Mutation | Type | Sequence |
|---|---|---|
| c.296G>T, p.G99V | WT | acctgccgcgGggacctcgcc (SEQ ID NO: 31) |
|  | MT | acctgccgcgTggacctcgcc (SEQ ID NO: 32) |
| c.842T>C, p.I281T | WT | gctgcctacaTtggcacaact (SEQ ID NO. 13) |
|  | MT | gctgcctacaCtggcacaact (SEQ ID NO. 14) |
| c.959G>T, p.G320V | WT | tgtgttggggGgtgccctcca (SEQ ID NO. 15) |
|  | MT | tgtgttggggTgtgccctcca (SEQ ID NO. 16) |
| c.1079delC, p.C361fsX366 | WT | tacttccattCctgtgtcttt (SEQ ID NO. 17) |
|  | MT | tacttccatt_ctgtgtcttt (SEQ ID NO. 18) |
| c.976C>T, p.R326X | WT | tccaagtcagCgactctctcg (SEQ ID NO. 29) |
|  | MT | tccaagtcagTgactctctcg (SEQ ID NO. 30) |

Table 1 shows genetic variations identified in HFE2A (ENSE00001277351). The cDNA position of the mutation is represented by the number in the first column (i.e.; c.665). The mutations are numbered starting from the initiating ATG codon in ENST00000306561 (transcript 4) (SEQ ID NO. 9). For each variation ten bases of sequence on either side is presented with the wildtype (WT) and mutant (MT) base capitalized.

Table 2 shows genetic variations identified in Juvenile Hemochromatosis families. The first column describes the variation, the other columns present the genotype of each chromosome at the site of mutation of a proband in each family. JH3, 4, 5, 6, 7, 8, 9, 10 and 12 are homozygous for the variation. JH11 is a compound heterozygote with two variations.

Segregation of the indicated mutations in HFE2A with affected HFE2A patients has now been confirmed in all affecteds in the families identified in Table 2. The variation is not found in 128 European and 37 Greek control (unaffected) individuals. Thus, the presence of 7 families having one coding change resulting in a G320V, one family having a unique coding change resulting in a I281T, and two other families having a premature truncation of this protein is convincing evidence that mutations in HFE2A (Gene 3 (LOC148738) ENSG00000168509 v.12.31.1) cause Juvenile Hemochromatosis.

Another variation occurred in control samples (i.e. unrelated persons not affected with JH). Two of 128 Dutch controls are heterozygous for c.1207G>A, p.V403I. Since it was heterozygous in these two samples, no JH phenotype would be expected to be apparent, nor is it found in these individuals. This variation could be a single nucleotide polymorphism (SNP) in the Dutch population which is not deleterious. Alternatively, it may be a potentially causal mutation of JH were it to appear in the homozygous form. At this point it is just a SNP, but it may be useful for diagnostic, or therapeutic purposes.

A significantly conserved genomic DNA promoter nucleic acid sequence for HFE2A has been identified in humans, mouse and rat as follows:

| SEQ ID NO. | Description |
|---|---|
| 19 | Promoter sequence - human |
| 20 | Promoter sequence - mouse |
| 21 | Promoter sequence - rat |

Figures 1, 2:
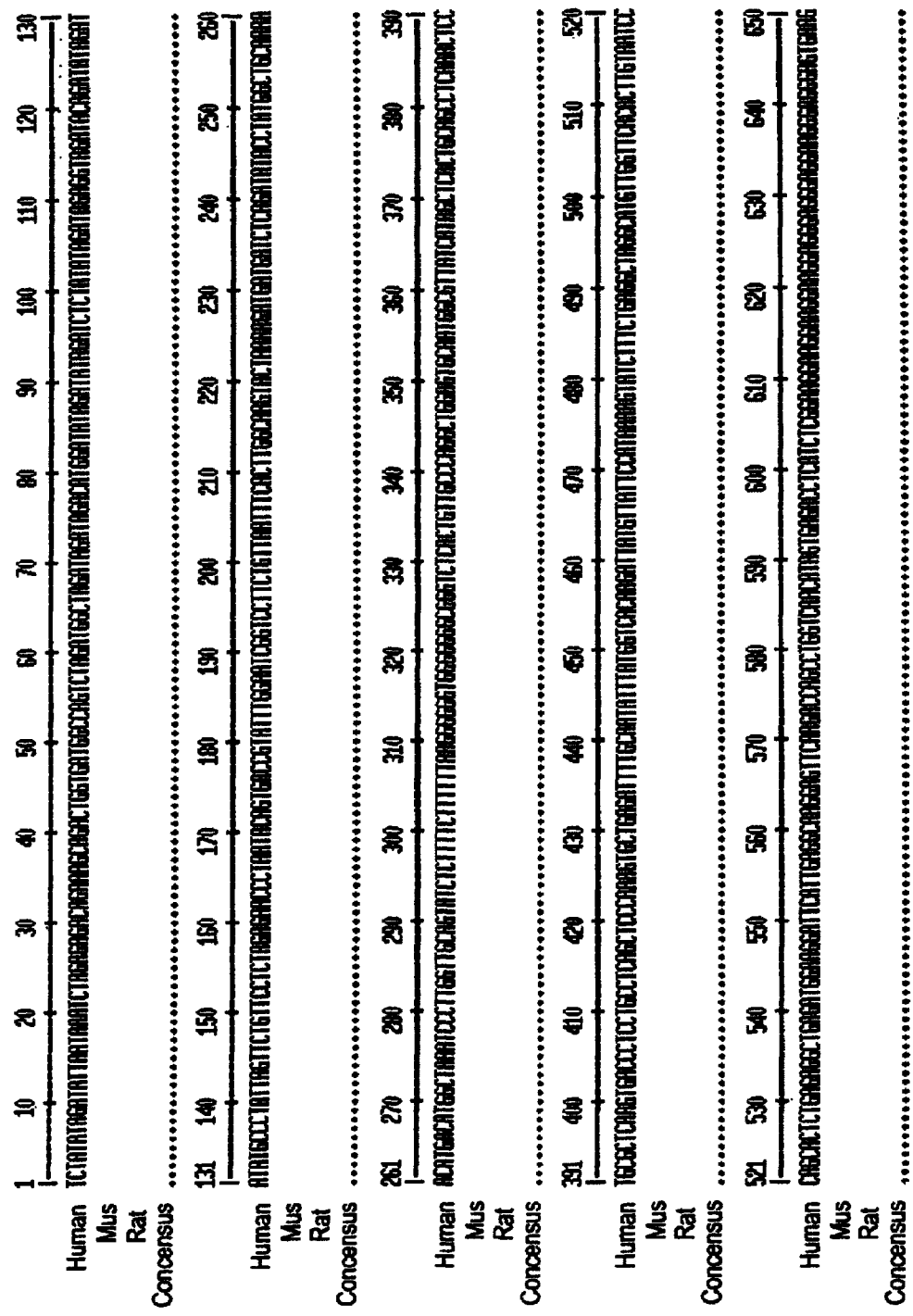
FIG. 2 is an alignment of the human (SEQ ID NO: 19), mouse (SEQ ID NO: 20) and rat (SEQ ID NO: 21) promoter sequences for HFE2A. The transcriptional start site of the human sequence begins at position 1514 of this alignment and exon 1 ends at position 1676. Three repetitive sequences are present within the human sequence, a (TAGA)n at position 58 to 129, an alu repetitive element at position 324 to 603 and a (GGAA)n at position 604 to 702. These sequences are not present in the rodent sequences and possibly define the promoter boundary for the gene. Sequence homology between species is lost 5' of position 844 of this alignment, about 670 bp 5' of the transcriptional start. A putative transcriptional initiation site (TATA) is conserved in all three species, at 27 to 24 bp 5' of the transcriptional start in the human. The figure also shows a consensus sequence (SEQ ID NO: 63) based on the alignment of the human, mouse and rat sequences.
Figure 2:
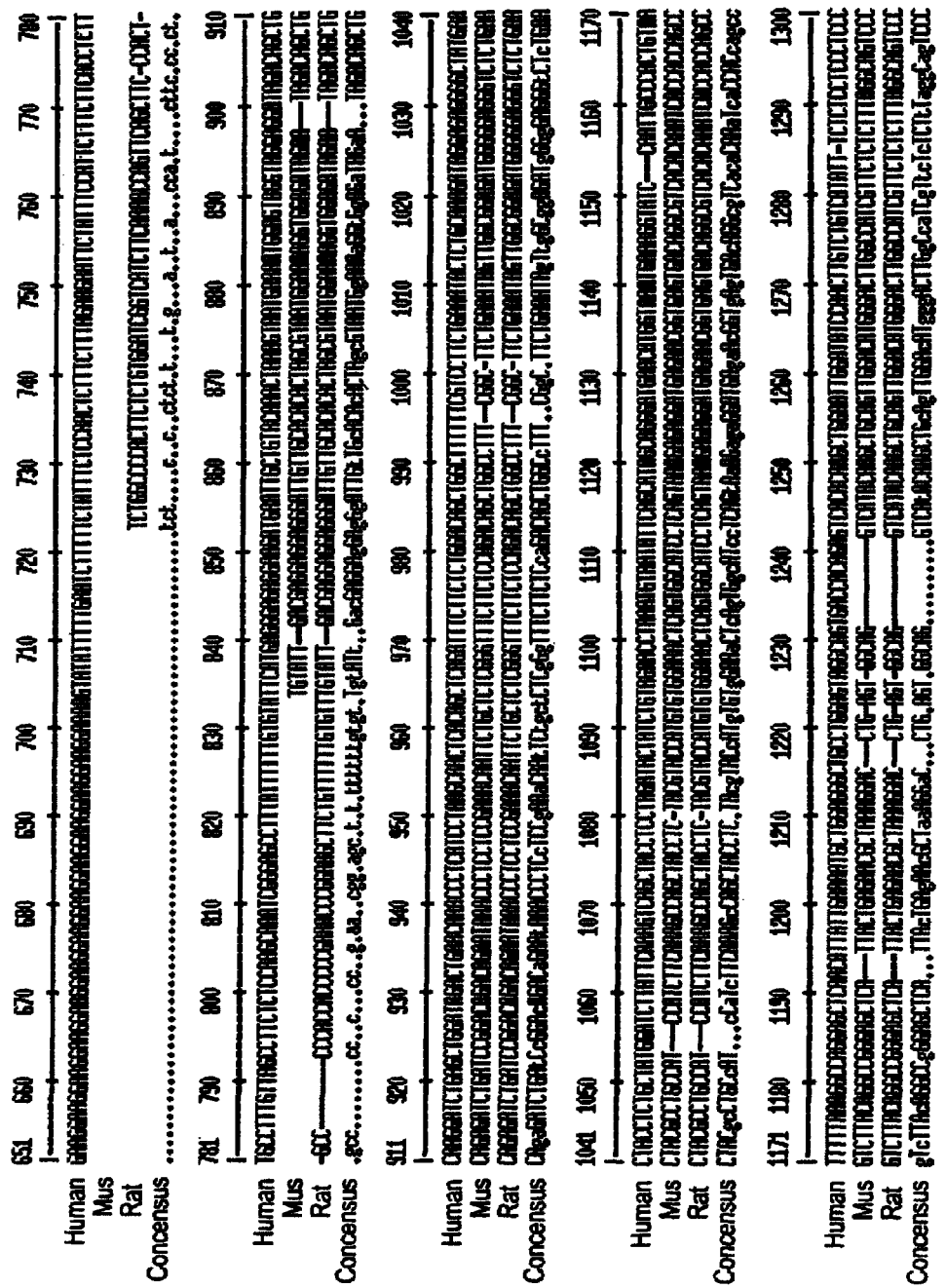

Alignment of the promoter sequences in FIG. 2 shows the high degree of conservation between species in the regulatory region. Sequence conservation is substantially lost about 670 nt 5' to the transcription initiation site in the human sequence.

Genomic sequence: the full human genomic sequence illustrating the nucleic acid-sequence around HFE2A is set forth at SEQ ID NO. 22. Exons are indicated in capital letters.

In accordance therewith, a gene useful in the methods of the invention comprises a polynucleotide corresponding to a polynucleotide having a nucleotide sequence selected from the group consisting of SEQ ID NO: 19, 20, 21 and 22.

In another aspect, the present invention relates to a method for identifying an agent that modulates HFE2A gene expression, comprising:

(a) contacting a test compound with a genetic construct comprising a reporter gene operably linked to an HFE2A promoter under conditions supporting expression of said reporter gene;

TABLE 2

| Variation | JH3 | JH4 | JH5 | JH6 | JH7 | JH8 | JH9 | JH10 | JH11 | JH12 |
|---|---|---|---|---|---|---|---|---|---|---|
| c.296G > T, p.G99V |  |  |  |  |  |  | TT |  |  |  |
| c.842T > C, p.I281T |  | CC |  |  |  |  |  |  |  |  |
| c.959G > T, p.G320V | TT |  | TT | TT | TT |  |  | TT | GT | TT |
| c.1079delC, p.C361fsX366 |  |  |  |  |  | del/del |  |  |  |  |
| c.976C > T, p. R326X |  |  |  |  |  |  |  |  | TC |  |

(b) determining a change in expression of said reporter gene as a result of said contacting, wherein a change expression identifies said test compound, or confirms said test compound, as an agent that modulates HFE2A gene expression.

In preferred embodiment thereof, the modulation is a decrease or increase in expression, especially transcription, of said reporter gene and includes embodiments where the HFE2A promoter is a mammalian HFE2A promoter, preferably a mouse, rat or human HFE2A promoter. In a highly preferred embodiment, the promoter has a nucleotide sequence of SEQ ID NO: 19.

In a preferred embodiment, the expression of said reporter gene is determined by measuring the activity of an enzyme, such as where the reporter gene encodes a protein having a readily measurable enzyme activity.

As used herein, the term "identifying" can include first identifying said test compound as an agent that modulates gene expression or a polypeptide activity (i.e., where the agent was not previously known or suspected of having this activity) or can include confirming such activity (where the agent was already suspected of having this activity but was not clearly shown to have such activity) by performing one or more of the assays of the invention. For example, where an agent has previously been implicated in modulation of HFE2A gene or polypeptide activity, or where such agent was suspected, or otherwise believed to be, an agent capable of altering, modulating, or affecting iron metabolism, such as where the agent has been implicated in regulating iron metabolism, and the activity of such agent is confirmed to have such activity utilizing a method of the invention, such agent is deemed to have been identified as having the indicated activity.

In another aspect, the present invention relates to a method for identifying an agent that modulates HFE2A polypeptide activity, comprising;
(a) contacting a chemical agent with said HFE2A polypeptide under conditions promoting protein:protein interactions, and/or
(b) contacting a chemical agent with said HFE2A polypeptide under conditions promoting HFE2A ligand HFE2A receptor interactions, and/or
(c) contacting a chemical agent with said HFE2A polypeptide under conditions promoting modifications in lipid composition, and/or
(d) contacting a chemical agent with said HFE2A polypeptide under conditions promoting alterations in associated second messenger signaling
wherein such interaction, alteration or modification indicates modulation and thereby identifying the chemical agent as an agent that modulates HFE2A polypeptide activity.

HFE2A activity may be mediated through alteration of an associated second messenger.

In one highly useful embodiment, the genetic construct is in a cell, preferably a mammalian cell, most preferably a recombinant cell, such as where the mammalian cell is a macrophage, liver cell, hepatocyte, intestinal cell, inflammatory cell, liver cell, hepatocyte, intestinal cell, hematopoietic cell, pancreatic cell, skeletal muscle cell or a nervous system cell.

Table 3 below sets forth other polymorphisms that have been identified in the HFE2A gene of control individuals (i.e. those with no clinical manifestation of Juvenile Hemochromatosis or other iron metabolism disorder). These polymorphisms, and others that may be discovered by those skilled in the art, may be useful for diagnostic or therapeutic or other purposes.

TABLE 3

| Mutation | Type | Sequence | |
|---|---|---|---|
| c.1-15C>G, na | WT | gcctgggaaaCctggctggat | (SEQ ID NO: 33) |
| | MT | gcctgggaaaGctggctggat | (SEQ ID NO: 34) |
| c.98-6C>G, intronic 2-3 | WT | tcccttctgtCtttagctcat | (SEQ ID NO: 35) |
| | MT | tcccttctgtGtttagctcat | (SEQ ID NO: 36) |
| c.205_206insAGG, p.G69_70insG | WT | gaggaggagg---ccggggtgga | (SEQ ID NO: 37) |
| | MT | gaggaggaggAGGccggggtgga | (SEQ ID NO: 38) |
| c.432C>G, p.A144A | WT | gcctccctgcCccggacccTT | (SEQ ID NO: 39) |
| | MT | gcctccctgcGccggacccTT | (SEQ ID NO: 40) |
| c.483C>A, p.P161P | WT | atggtcgtccCccggggttct | (SEQ ID NO: 41) |
| | MT | atggtcgtccAccggggttct | (SEQ ID NO: 42) |
| c.488G>C, p.G163A | WT | cgtcccccggGgttcttgcat | (SEQ ID NO: 43) |
| | MT | cgtcccccggCgttcttgcat | (SEQ ID NO: 44) |
| c.569C>A, p.A190D | WT | gtccaaggagCttggcctcta | (SEQ ID NO: 45) |
| | MT | gtccaaggagAttggcctcta | (SEQ ID NO: 46) |
| c.627G>T, p.A209A | WT | ccccatggcGttgggggcca | (SEQ ID NO: 47) |
| | MT | ccccatggcTttgggggcca | (SEQ ID NO: 48) |
| c.682C>A, p.Q228K | WT | taagaacatgCaggaatgcat | (SEQ ID NO: 49) |
| | MT | taagaacatgAaggaatgcat | (SEQ ID NO: 50) |

TABLE 3-continued

| Mutation | Type | Sequence | |
|---|---|---|---|
| c.929C>G, p.A310G | WT | gccttctcagCtgaacaggac | (SEQ ID NO: 51) |
| | MT | gccttctcagGtgaacaggac | (SEQ ID NO: 52) |
| c.1207G>A, p.V403I | WT | agatgctgggGttcctctttc | (SEQ ID NO: 53) |
| | MT | agatgctgggAttcctctttc | (SEQ ID NO: 54) |

Capital letter indicates site and nature of polymorphism. WT = wild-type; MT = mutation.

Similarity to Other Human Genes

Figures 2, 3:
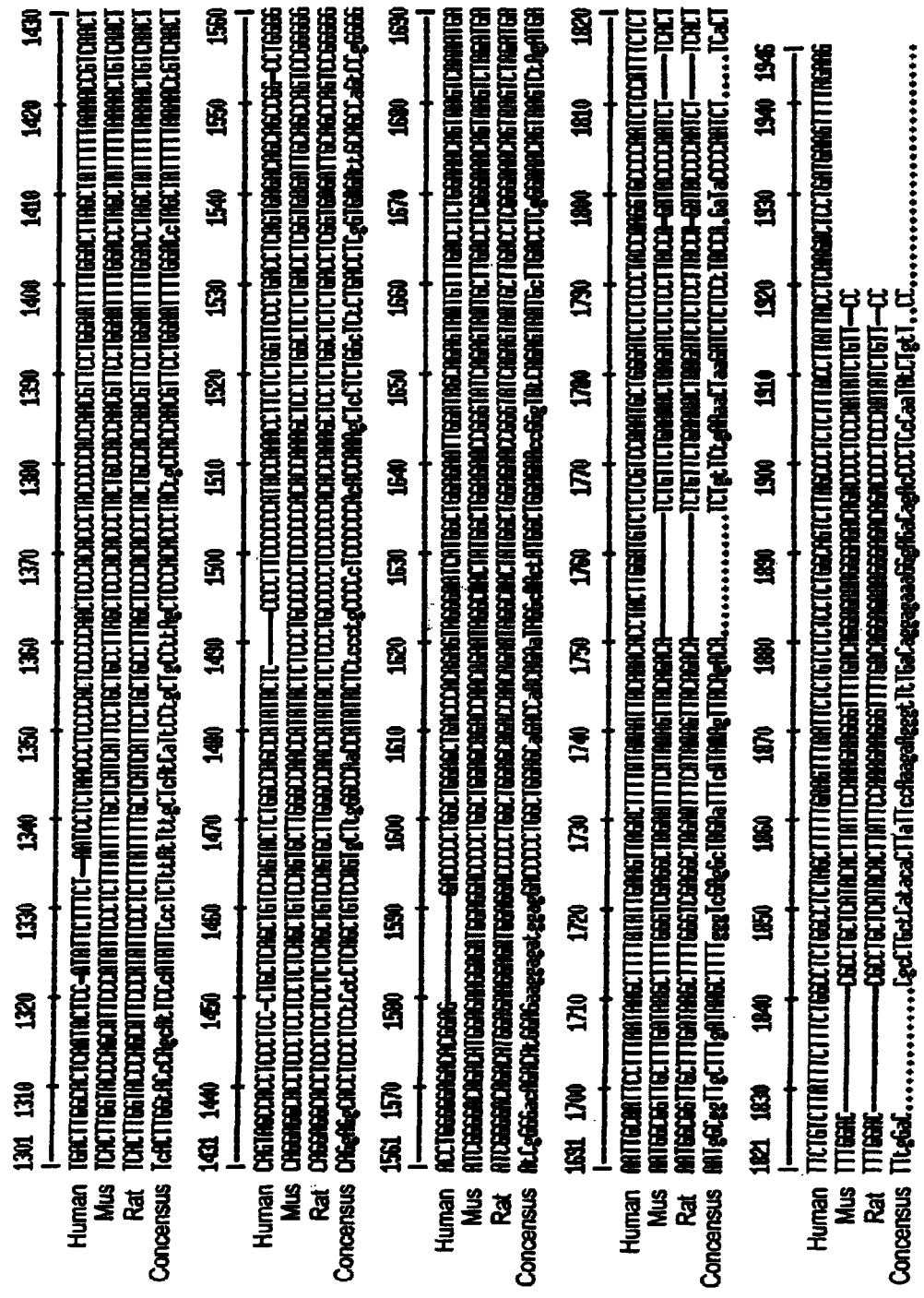
FIG. 3 shows a Protein Sequence Alignment of Human LOC148738 426 aa Gene Product (Protein3—SEQ ID NO: 12) and human paralogs; Human Repulsive Guidance Molecule (Human RGM SEQ ID NO: 23) (NCBI: NP_064596.1) on Chromosome 15 and ENSESTP00000023393 (SEQ ID NO: 24—Ensembl) identified on Chromosome 5.—Comparison of human paralogs
Figure 3:
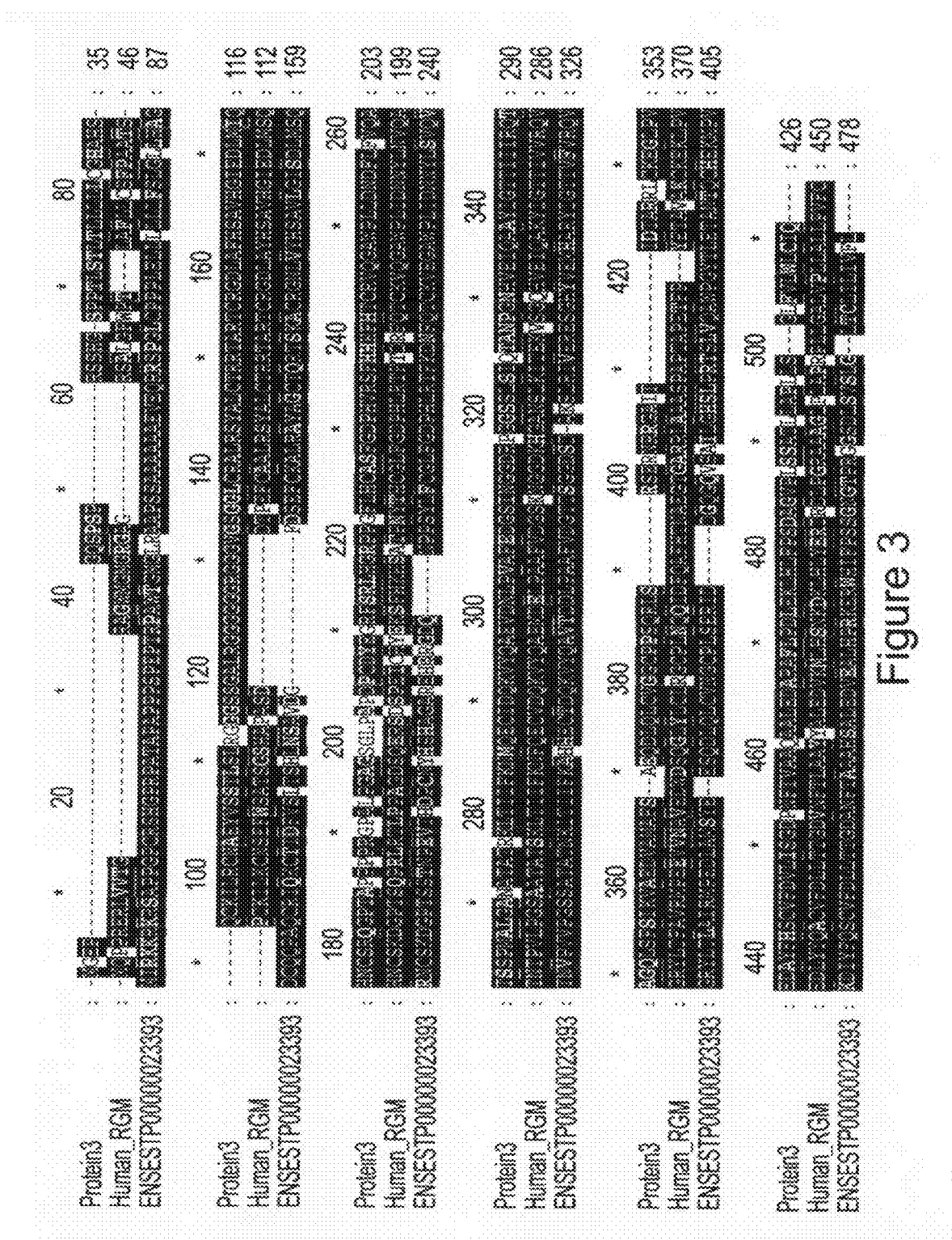

FIG. 3 illustrates an alignment between HFE2A and 2 related proteins found in the human genome. The similarity suggests that some functionality may be shared or similar between these proteins.

Table 4 shows a comparison of Human LOC148738 426 aa protein sequence (Protein3) to Human Paralogs* using BLAST**

TABLE 4

| Paralog | Score | Alignment (a.a.) | Identity % | Positive % | Gaps % |
|---|---|---|---|---|---|
| Human RGM (SEQ ID No. 23) | 370 bits (939) | 432 | 48% | 60% | 12% |
| ENSESTP00000023393 (SEQ ID No. 24) | 333 bits (844) | 444 | 42% | 55% | 13% |

*ENSESTP00000023393 (Ensembl) on Chromosome 5 and Human Repulsive Guidance Molecule (Human RGM) (NCBI: NP_064596.1) on chromosome 15
**Sequence comparison using "BLAST 2 Sequences" (Tatiana A. Tatusova, Thomas L. Madden (1999), FEMS Microbiol Lett. 174: 247-250) Parameters: blastp, BLOSUM62 matrix, open gap penalty of 11, extension gap penalty of 1, gap x_dropoff of 50, word size of 3, expect 10

Conservation of HFE2A in Other Organisms.

Figure 4:
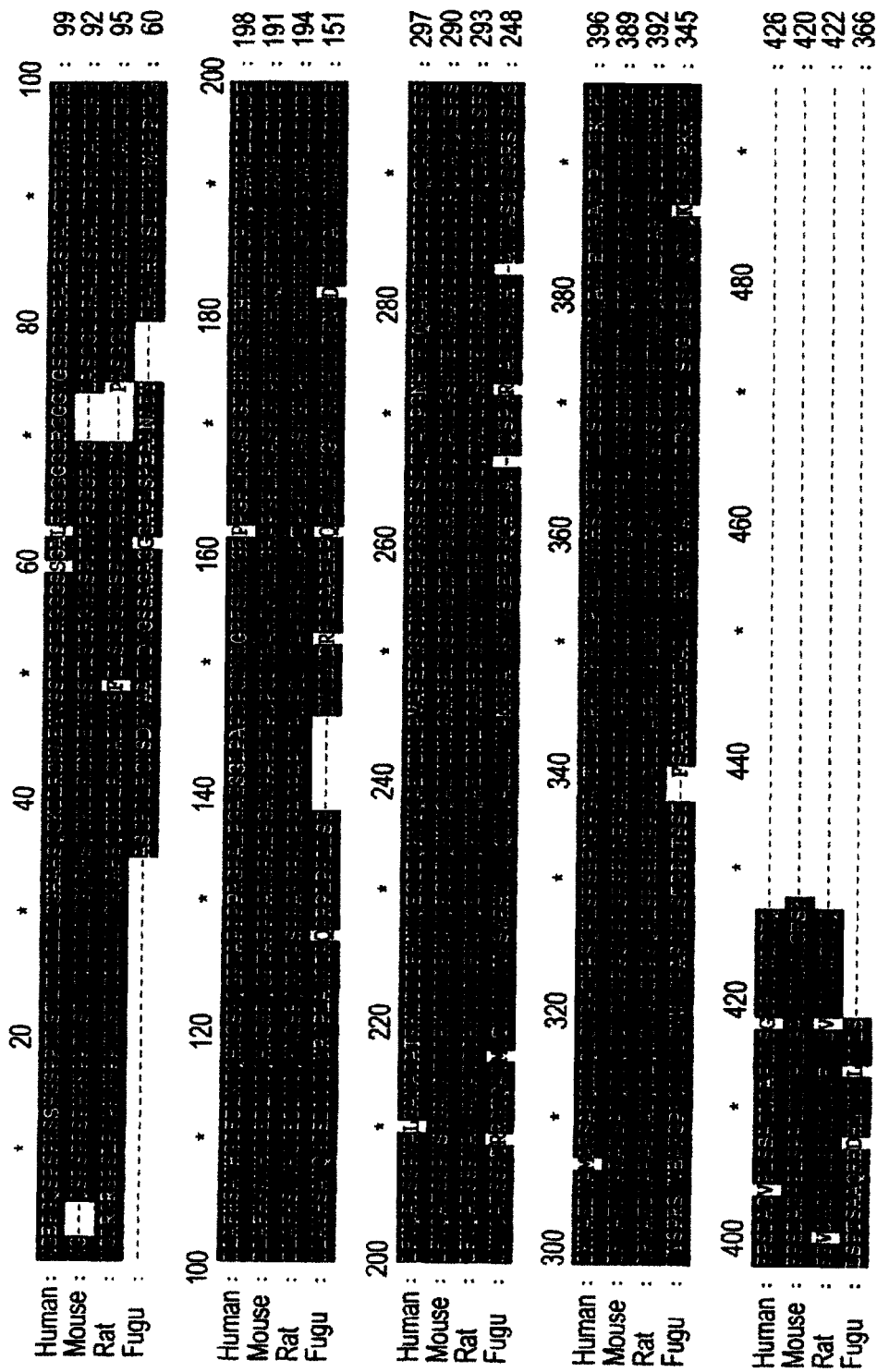
FIG. 4 shows a Sequence Alignment of LOC148738 sequences using clustalx. Human (Protein3—SEQ ID NO: 12), Mouse (Ensembl: ENSMUSESTP00000016634—SEQ ID NO: 25), Rat (Translated from NCBI: AK098165.1—SEQ ID NO: 26). Though annotated as human sequence it is 99.9% identical to Rat genomic sequence and only 86.6% identical to human genomic sequence) and Fugu (Ensembl: SINFRUP00000138308—SEQ ID NO: 27).

2. Homologs of human HFE2A gene were found in mouse (*Mus musculus*), rat (*Rattus norvegicus*) and fish (*Takifugu rubripes* ("Fugu")). FIG. 4 sets out a sequence comparison at the nucleotide level of these sequences. The high degree of conservation of these sequence is shown in Table 5, which shows a comparison of Human LOC148738 426 aa protein sequence (Protein3) to Orthologs* using BLAST**

TABLE 5

| SPECIES | Score | Alignment (a.a.) | Identity % | Positive % | Gaps % |
|---|---|---|---|---|---|
| Mouse SEQ ID No. 25 | 758 bits (1936) | 420 | 88% | 90% | 0% |
| Rat SEQ ID No. 26 | 752 bits (1920) | 426 | 86% | 89% | 0% |
| Fugu SEQ ID No. 27 | 336 bits (853) | 383 | 46% | 61% | 4% |

*Organism sequences: Mouse (Ensembl: ENSMUSESTP00000016634), Rat (Translated from NCBI: AK098165.1) and Fugu (Ensembl: SINFRUP00000138308).
**Sequence comparison using "BLAST 2 Sequences" (Tatiana A. Tatusova, Thomas L. Madden (1999), FEMS Microbiol Lett. 174: 247-250) Parameters: blastp, BLOSUM62 matrix, open gap penalty of 11, extension gap penalty of 1, gap x_dropoff of 50, word size of 3, expect 10

Figure 5:
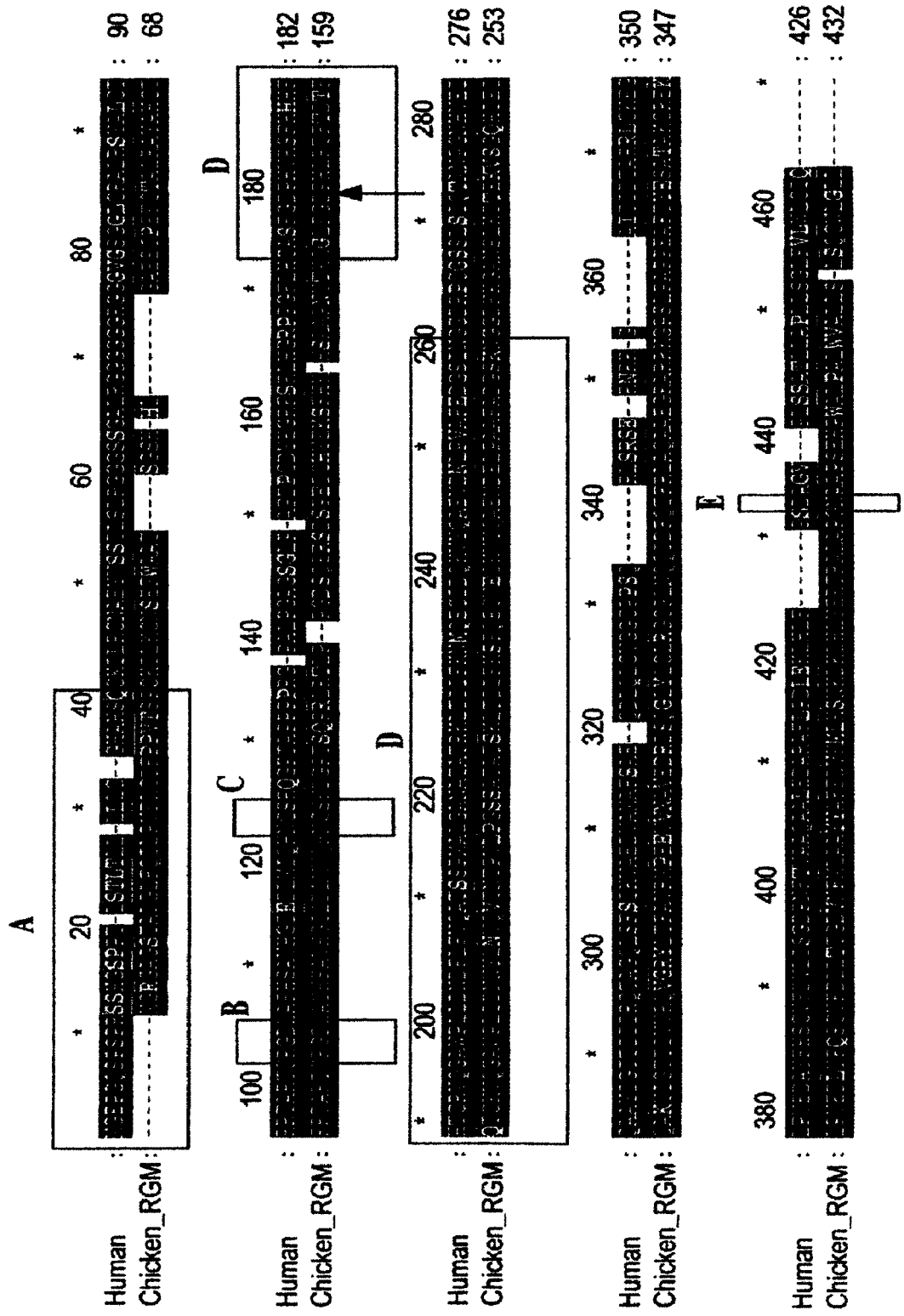
FIG. 5 shows a Protein Sequence Alignment of Human LOC148738 gene product and Chicken Repulsive Guidance Molecule (RGM—SEQ ID NO: 28). Human (Protein3—SEQ ID NO: 12), Chicken_RGM (Translation of NCBI: AY128507.1). A=Signal Peptide, B=RGD, C=N-Glycosylation site, D=Partial von Willebrand Type D Domain, E=GPI modification , Arrow=Possible cleavage site.

Comparison of human HFE2A with chicken RGM is shown in FIG. 5. The 426 aa sequence translation of Human LOC148738 (Protein3 identical to ENSP00000304614) shares significant sequence homology with Chicken_Repulsive Guidance Molecule (RGM) (Translation of NCBI: AY128507.1). Chicken RGM amino acid sequence is listed at SEQ ID No. 28. Using "BLAST 2 Sequences" (Tatiana A. Tatusova, Thomas L. Madden (1999), FEMS Microbiol Lett. 174:247-250) 395 of the residues align with 46% Identity, 61% Positives and 9% Gaps. The two proteins also share a N-terminal signal peptide, a RGD tri-amino acid motif that could be involved in cell attachment, a site identified as a possible cleavage site in Chicken RGM, a partial (~57%) von Willebrand Type D domain, and a predicted N-Glycosylation site. Both proteins are also predicted to have GPI modifications at the C-terminus.

Figure 6A:
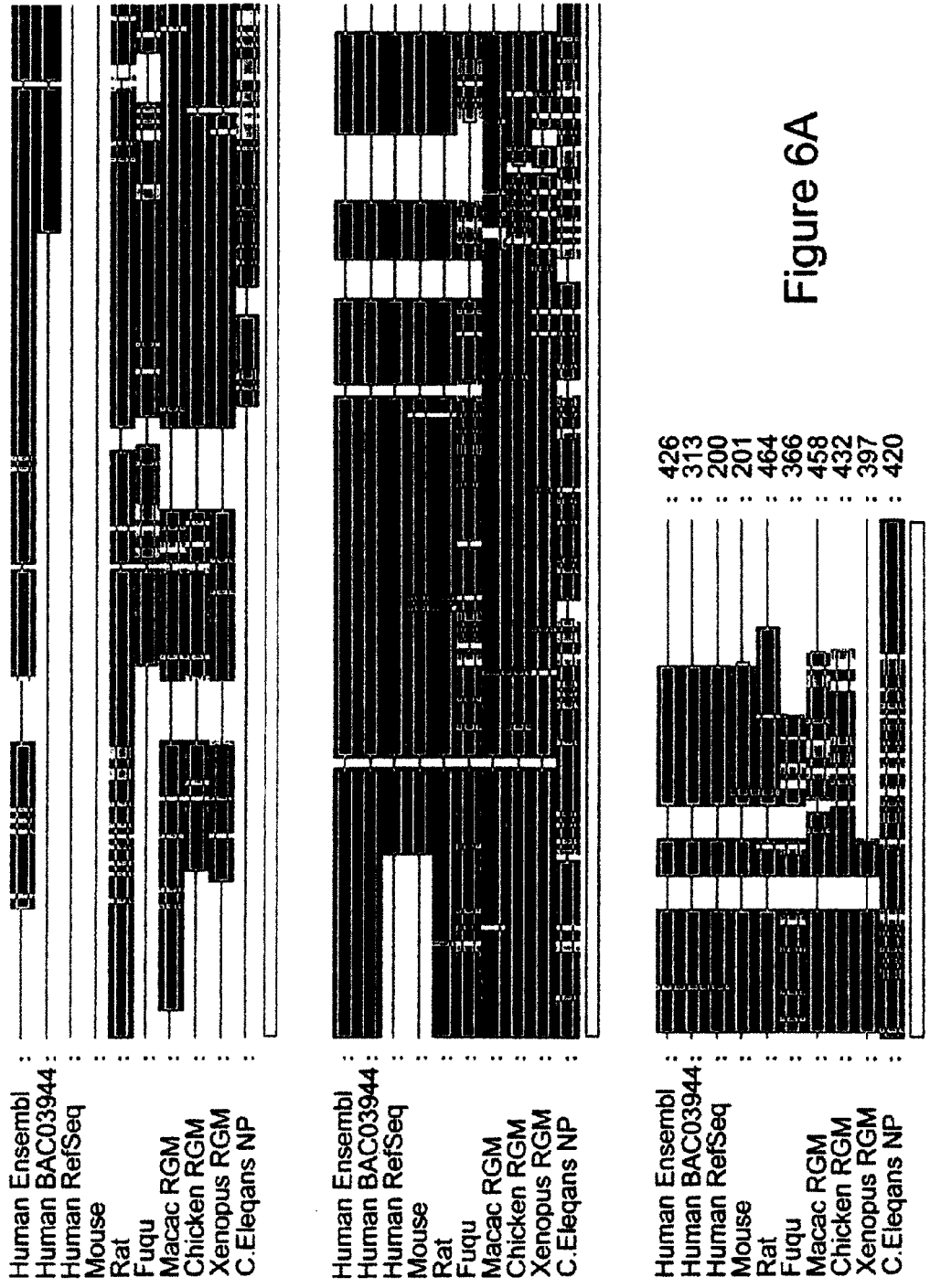
FIG. 6A shows a summary of high degree of similarity between homologs of several species.
Figures 1, 6B:
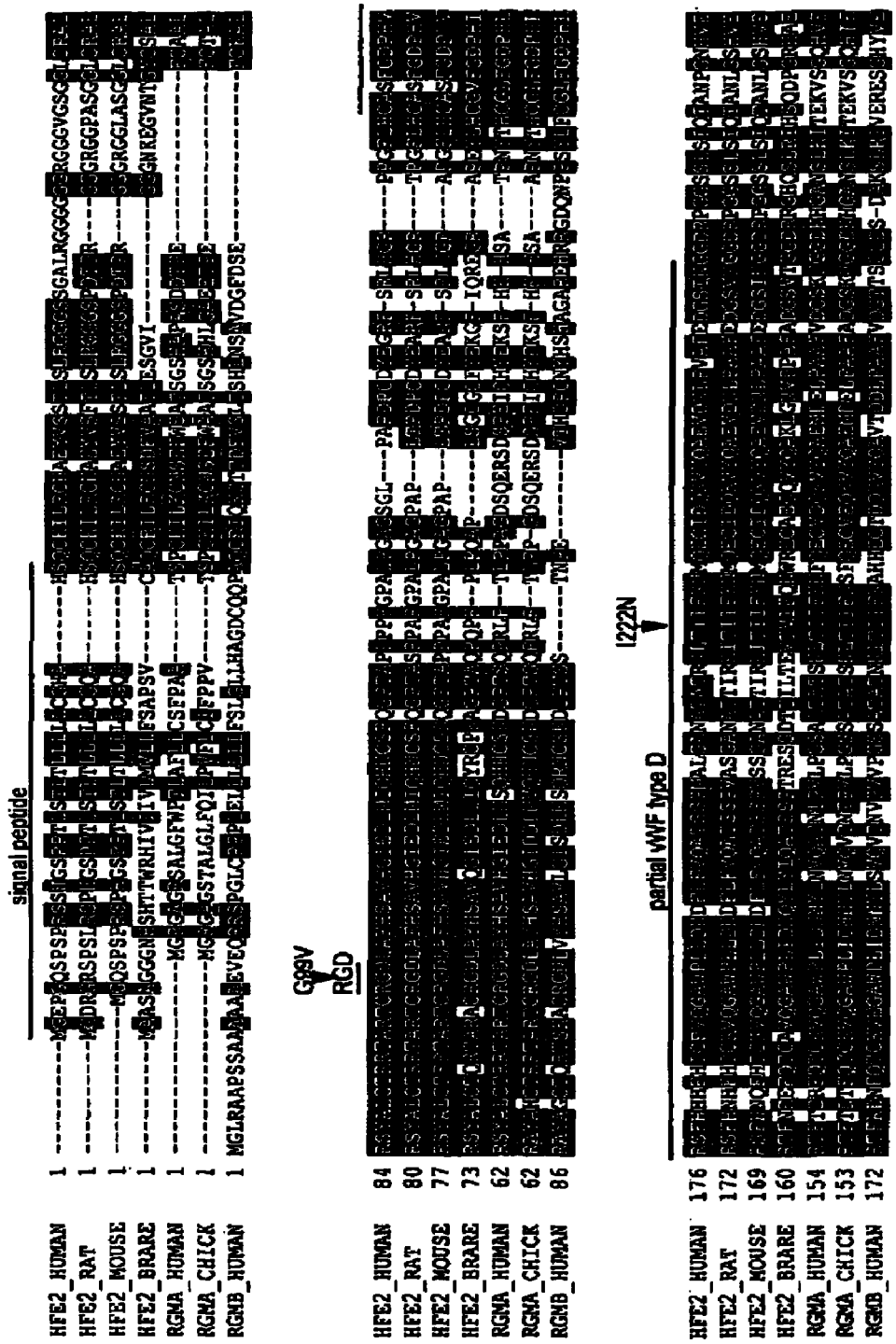
FIG. 6B shows the high degree of similarity between genes similar to HFE2A in different species. These include: human HFE2 (SEQ ID NO: 12), rat HDE2 (SEQ ID NO: 26), mouse HFE2 (SEQ ID NO: 25), brare HFE2 (SEQ ID NO: 64), human RGMA (SEQ ID NO: 65), chick RGMA (SEQ ID NO: 28), and human RGMB (SEQ ID NO: 66).
Figures 2, 6B:
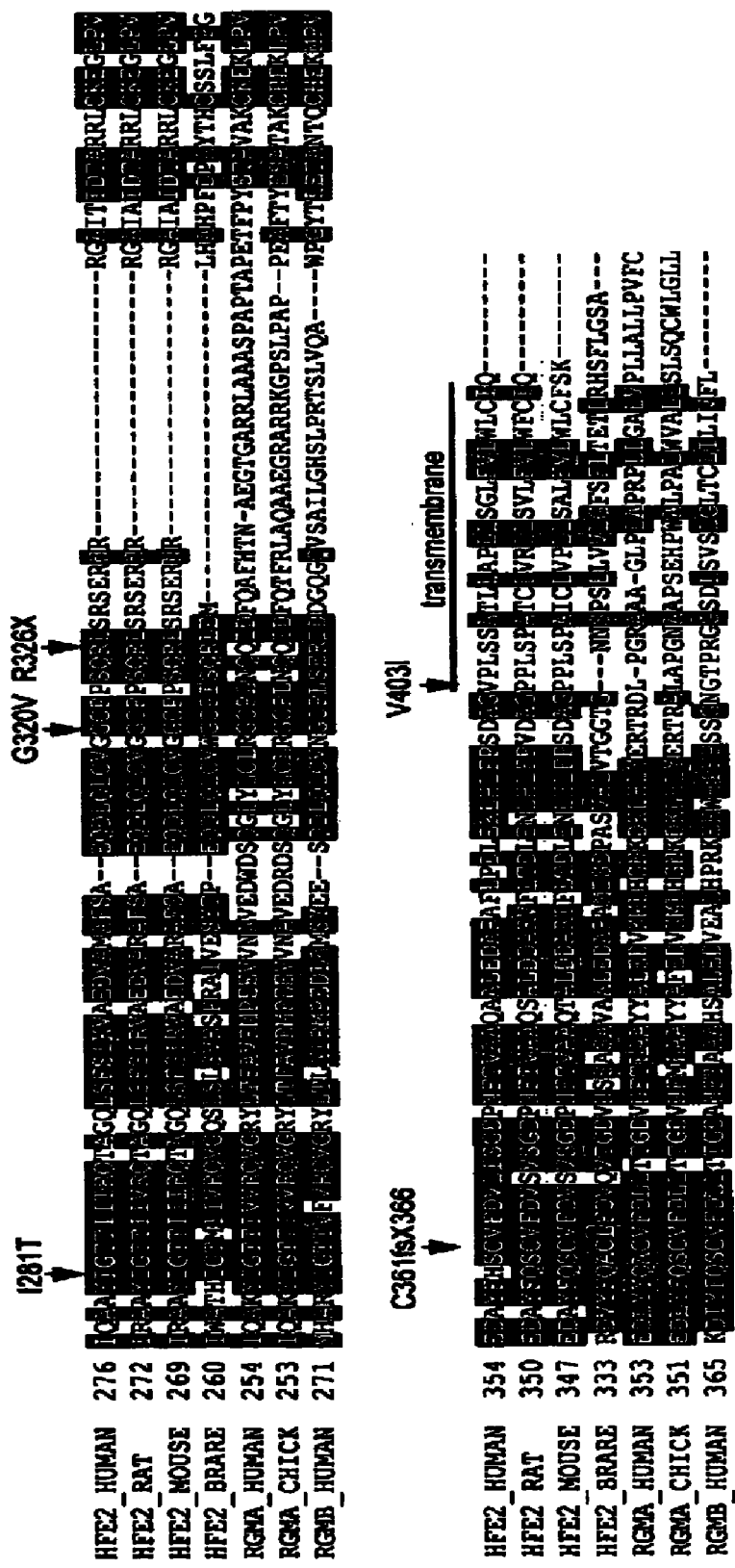

A visual overview of similarities shared between human HFE2A and homologs in mouse, rat and fugu, as well as sequences from Macac RGM, Chicken RGM, Xenopus RGM and C.Elegans NP are shown in FIG. 6. This degree of similarity illustrates that similar genes or proteins from other species may be useful for various embodiments of the invention. The protein also has the sequence Arg-Asn-Arg-Arg$^{335}$ (SEQ ID NO: 70) representing the consensus cleavage site (Arg-X-Lys/Arg-Arg (SEQ ID NO: 71)) for the proprotein convertase furin (Molloy, S. S. et al. J. Biol. Chem., 267, 16396-16402, (1992)) which would result in cleavage between positions 335 and 336.

A comparison of sequences between related genes from human, mouse, rat, chicken and zebrafish is shown at FIG. 6B. Orthologs of the human HFE2A protein are found in mouse, rat and zebrafish (FIG. 6B). Sequence comparison shows that human HFE2A is >85% identical with the mammalian orthologs, and ~45% identical to the fish ortholog. The 426 amino acid translation of HFE2A also shares significant sequence similarity with the Repulsive Guidance Molecule (RGM or RGMA) of human (48% identity) and chicken (46% identity) (FIG. 6B). In humans there is also a third RGM-like gene, RGMB, whose biological function is currently unknown.

HFE2A Polypeptide Function

This invention teaches the important discovery that HFE2A is a critical regulator of iron metabolism. Exactly how it is involved in this process remains to be fully clarified. Important information about the activity of this protein can be determined based on the analysis of protein domains.

Figure 7A:
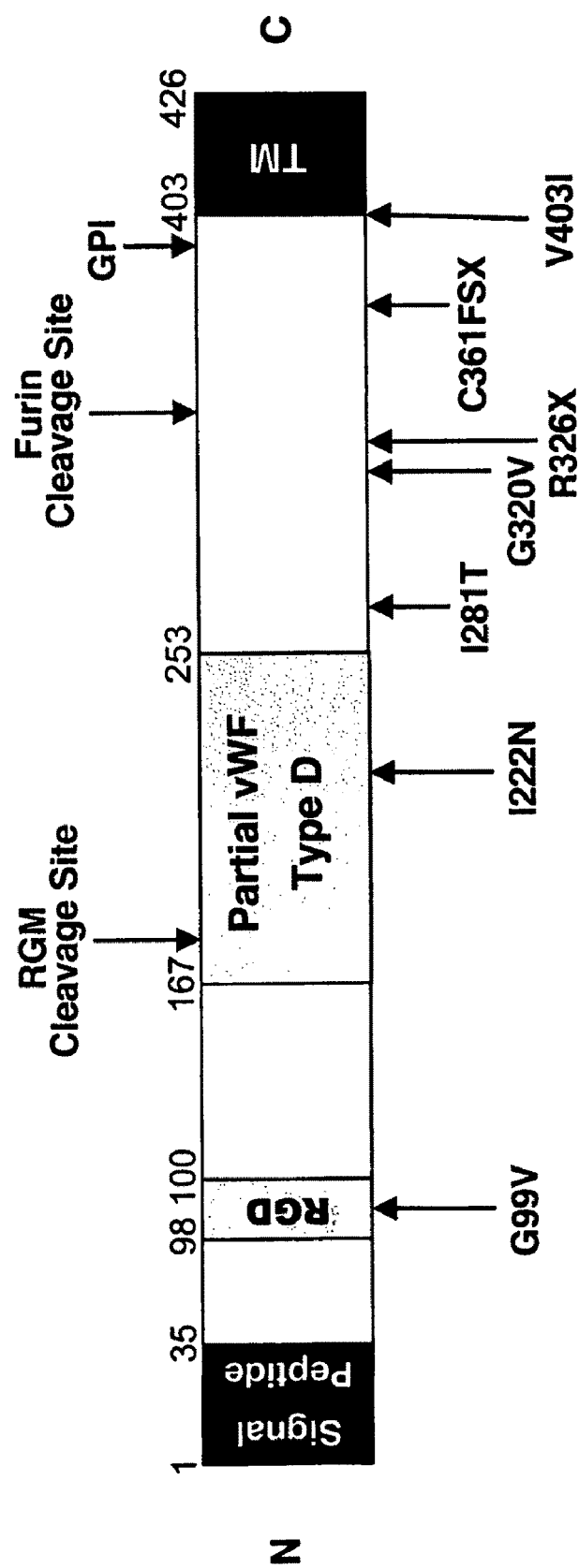
FIG. 7(a)—Structural features in the 426 aa translated open reading frame of LOC148738. RGD—cell attachment tri amino acid motif, vWF—Partial von Willebrand factor type D domain and TM—Transmembrane domain. The arrows mark a possible proteolytic site between positions 172 and 173, a furin cleavage site between positions 335 and 336 and a predicted GPI modification site at position 400.
Figure 7B:
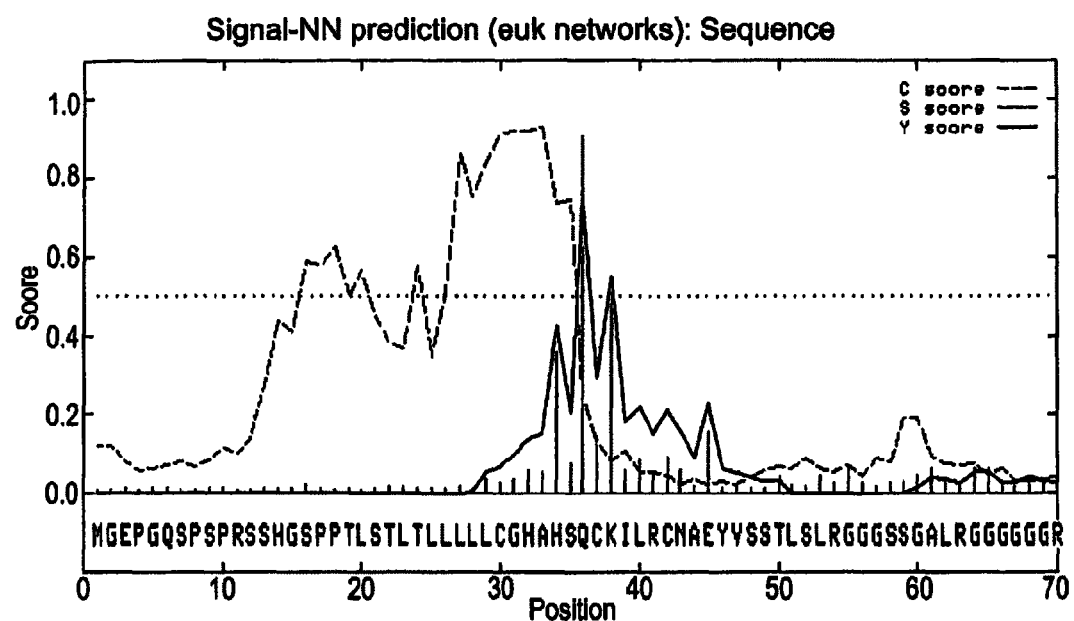
FIG. 7(b) shows the prediction of signal peptide (amino acids 1-70 of SEQ ID NO: 12) cleavage site in 426 aa translation of HFE2A using SignalP (Henrik Nielsen et al. *Protein Engineering*, 10, 1-6 (1997)). Peptide cleavage site is predicted to be between S35 and Q36.
Figure 7C:
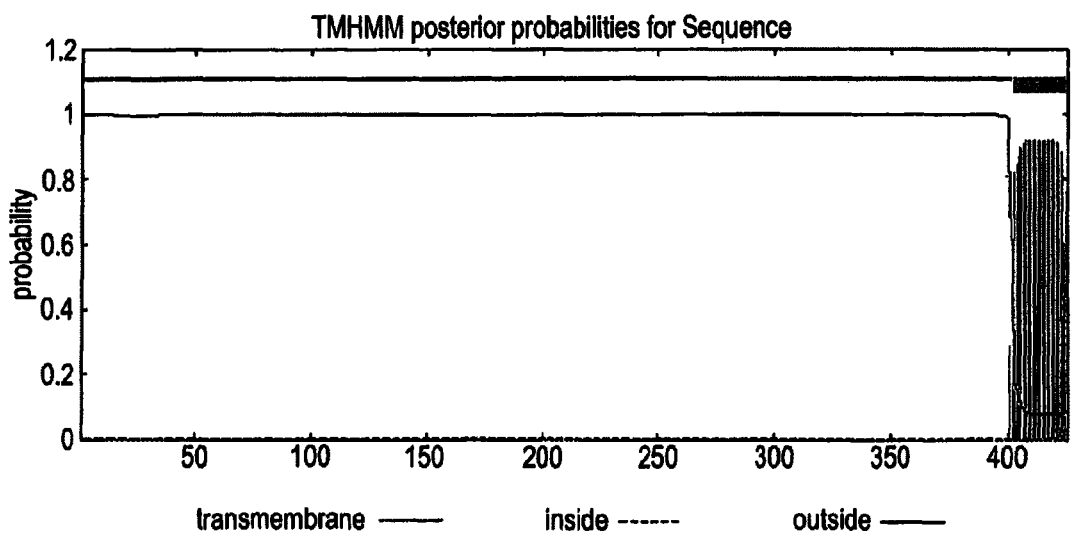
FIG. 7(c) shows the prediction of transmembrane regions in 426 aa translation of HFE2A using TMHMM. The transmembrane region is from residues 403-425.
Figure 9C:
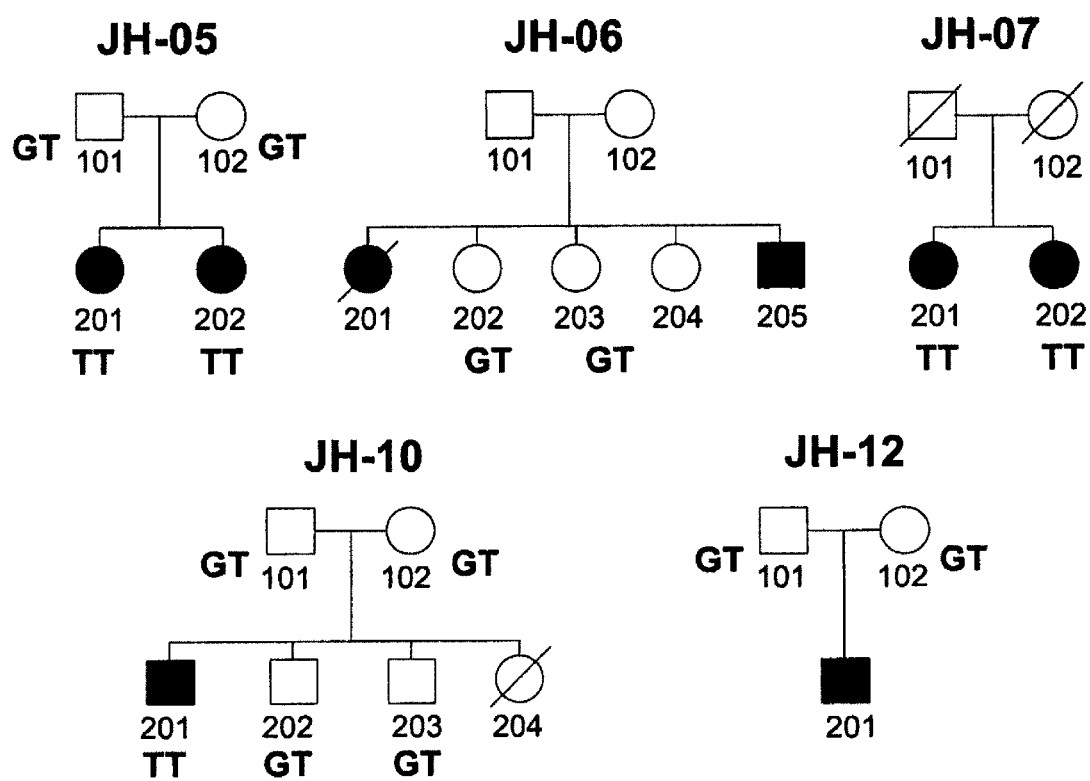
FIG. 9 (a)-(e)—shows family pedigrees used to identify genetic mutation causing juvenile hemochromatosis.
Figure 9D:
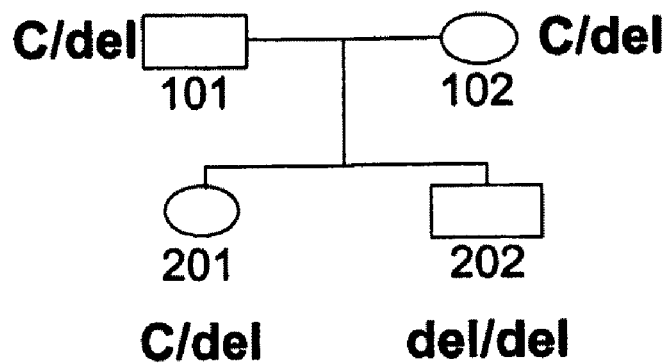
Figure 9E:
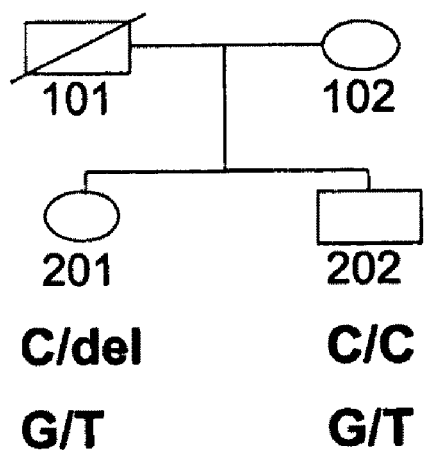

The 426 aa LOC148738 gene product (Protein3) has structural features consistent with a GPI (Glycosylphosphatidylinositol) anchored protein (FIG. 7a) including a N terminal hydrophobic signal peptide for access to the Endoplasmic Reticulum, where GPI anchor addition occurs (residues 1-35 FIG. 7b) and a C terminal hydrophobic domain/GPI addition signal sequence (residues 403-425 FIG. 7c) (Udenfriend S and Kodukula K Ann Rev Biochem 1995). The GPI predicting program big-Pi predictor predicts that this gene product is GPI modified, and that either amino acids 399 or 400 can act as the omega site (Eisenhaber et al., JMB, 292 (3), 741-758, 1999). Other features identified are a RGD—cell attachment tri amino acid motif (residues 98-100) (Ruoslahti, E. Annu. Rev. Cell Dev. Biol. 12, 697-715 (1996)) and a partial von Willebrand factor type D domain. von Willebrand factor type D domains are required for multimerization of von Willebrand factor (residues 167-253) (Jorieux, S. et al., Blood 1998 Dec. 15; 92(12):4663-70). In addition, the protein has a possible proteolytic cleavage site identified by sequence comparison with Chicken Repulsive Guidance Molecule (RGM) between residues 172 and 173 (FIG. 7e) (Monnier, P. P. et al. Nature 419, 392-394, 2002). Also present but not shown are N-glycosylation and O-glycosylation sites which appear to be consistent with consensus sequences.

FIG. 8 shows a protein domain analysis of HFE2A from a nucleotide/amino acid perspective. Features of the sequence are illustrated therein.

Further aspects of HFE2A Polypeptide function at the biochemical level may be determined by those skilled in the art using standard techniques. It is clear from the instant invention that HFE2A Polypeptide is directly involved in iron transport, as the absence of this gene in humans leads to the condition of juvenile hemochromatosis (type 2A) or HFE2A.

Sixteen human tissues were examined for HFE2A expression by probing Northern blots with a probe from exon 4. Significant HFE2A expression was detected in liver, heart (especially atria) and skeletal muscle (data not shown).

Based on publicly available ESTs (expressed sequence tags), fragments of this gene has also been found to be expressed in the following tissues:

Human HFE2A: skeletal muscle, liver, sciatic nerve, Liver and Spleen, prostate, heart;

Mouse HFE2A: mammary gland, heart, tongue, liver, xiphoid cartilage, medulla oblongata Rat HFE2A: brain, ovary, placenta, kidney, lung, liver, heart, muscle, spleen Therefore the HFE2A gene appears to be widely expressed in many tissues, but at reasonably low levels.

While not wishing to be bound to any particular mechanism of action of how HFE2A mutation causes juvenile hemochromatosis, or leads to adult onset hemochromatosis, it is possible to speculate on different roles the gene/protein of the invention may play in iron metabolism. For instance, the HFE2A protein may lie upstream or downstream of hepcidin in the iron metabolism pathway. One possibility is that the protein is the hepcidin receptor or a co-factor for the hepcidin receptor. Another possibility is that HFE2A functions in the transcription, translation and/or processing of hepcidin, and is necessary for proper functioning of hepcidin. HFE2A may be a hepcidin interacting protein. An alternate function is that the HFE2A protein may be a secreted factor from the bone marrow or liver, acting in a paracrine fashion, as a hormone or hormone-like compound regulator of hepcidin levels.

These possible mechanisms of action are suggestive for further exploration of the protein, but are not intended to be limiting on the scope of claims included below. In all of these scenarios, the functional consequences are the same, i.e. loss of function of HFE2A results in loss of the body's capacity to control iron metabolism through normal hepcidin function, thus precipitating the development of juvenile hemochromatosis, or adult onset hemochromatosis (possibly where other factors in the hepcidin/HFE2A metabolic pathway are not fully functional). Thus, modulating the activity of HFE2A is a method to regulate serum levels, biodistribubon, and/or metabolism of iron in the body.

Modulation of HFE2A is also a method for treating diseases which are not directly related to iron or iron metabolism. A function for HFE2A unrelated to its proposed role in iron metabolism is that of regulating blood volume. HFE2A is highly expressed in heart, especially in the right atrium, and therefore it is possible that HFE2A plays a hematological role, such as in sensing circulating blood volume and the regulation of blood volume. Alternatively, HFE2A may play a paracrine function in the heart protecting local myocytes from iron related disease. Compounds which modulate the activity of HFE2A are therefore useful in treating or preventing hematological disorders, cardiac disorders (including but not limited to cardiac failure, cardiomyopathy, disorders of fluid imbalance, and arrhythmias), and hormonal disorders. Also important, because hepcidin levels are stimulated in bacterial infections, inflammation, response to LPS injection, etc, HFE2A is a suitable therapeutic target for mediating aspects of these disorders, and could be important in treatment of bacterial sepsis, etc.

This invention establishes that the function of HFE2A is an essential regulator of iron in the human body, regardless of its exact mechanism of action. It is therefore a desirable drug target for treating diseases of iron metabolism in animals. For example, because HFE2A is directly implicated in JH and adult onset hemochromatosis according to this invention, the inventors recognize that JH and other diseases where iron metabolism is defective may be treatable by administering a chemical modulator of HFE2A. The disease may not necessarily be related to aberrant HFE2A gene or protein activity. For example, a compound which modulates HFE2A activity may compensate for insufficiencies in other aspects of the iron metabolism pathway. Or, a modulator of HFE2A may be used to treat a disease which is indirectly responding to iron levels in the blood.

As used in this disclosure the phrase "disease of iron metabolism" is therefore to be construed in its broadest context. This includes diseases where aberrant iron metabolism directly causes the disease, or where iron blood levels are disregulated causing disease, or where iron disregulation is a consequence of another disease, or where diseases can be treated by modulating iron levels, etc. More specifically, a disease of iron metabolism according to this disclosure includes iron overload disorders, iron deficiency disorders, disorders of iron biodistribution, other disorders of iron metabolism and other disorders potentially related to iron metabolism, etc. Even more specifically diseases of iron metabolism includes hemochromatosis, ferroportin mutation hemochromatosis, transferrin receptor 2 mutation hemochromatosis, juvenile hemochromatosis, neonatal hemochromatosis, hepcidin deficiency, transfusional iron overload, thalassemia, thalassemia intermedia, alpha thalassemia, sideroblastic anemia, porphyria, porphyria cutanea tarda, african iron overload, hyperferritinemia, ceruloplasmin deficiency, atransferrinemia, congenital dyserythropoietic anemia, anemia of chronic disease, anemia, hypochromic microcytic anemia, iron-deficiency anemia, conditions with hepcidin excess, Friedriek's Ataxia, gracile syndrome, Hallervan Spatz disease, Wilson's disease, pulmonary hemosiderosis, hepatocellular carcinoma, cancer, hepatitis, cirrhosis of liver, pica, chronic renal failure, insulin resistance, diabetes, atherosclerosis, neurodegenerative disorders, multiple sclerosis, Parkinson's Disease, Huntington's Disease, Alzheimer's Disease.

In particular, a modulator of HFE2A can usefully treat anemia of chronic disease. Worldwide, anemia of chronic disease (ACD, also know as Inflammatory Anemia) is the second most common form of anemia. ACD represents the most common form of anemia in hospitalized patients. ACD is an acquired disorder seen in patients with a variety of conditions including infection, malignancy and chronic inflammation. It is characterized by retention of iron by macrophages and decreased intestinal iron absorption, which leads to reduced iron availability for erythropoiesis. Early in the course of their disease, patients with ACD have a mild, normocytic anemia due to impaired iron recycling. Later, due to the reduced intestinal absorption they become franlkly iron deficient with a hypochromic microcytic picture. Initial studies examining the role of hepcidin in ACD show that excessive hepcidin production underlies ACD.

Loss-of-function of murine hepcidin leads to severe iron overload, mimicking the biochemical and clinical phenotype of JH. In contrast, in both animal models and human disease, hepcidin overexpression leads to macrophage iron retention and an iron deficient phenotype typical of the iron disturbances found in ACD. Existing therapy for ACD is mainly targeted to treating the underlying disorder, with no efficacious treatment specifically directed to amelioration of the iron phenotype. Therefore, therapeutic strategies to reduce hepcidin production, such as by inhibition of HFE2A represent an important novel approach to treating the iron disturbances seen in ACD.

In some cases the diseases and disorders included in the definition of "disease of iron metabolism" are not typically identified as being iron related. It is recognized by the instant invention that based on the tissue distribution of HFE2A (hemojuvelin) and its related protein, hepcidin, that iron metabolism may play a significant role in these disease processes. For example, it has recently been shown that hepcidin is very highly expressed in the murine pancreas suggesting that diabetes (Type I or Type II), insulin resistance, glucose intolerance and other disorders may be ameliorated by treating underlying iron metabolism disorders: (See Ilyin, G. et al. 2003 Febs. Letters 542 22-26). As such, these diseases are encompassed under the broad definition.

Method of Treatment Using HFE2A as a Therapeutic Target.

The discovery that mutations in HFE2A relate to clearly definable physiological outcomes in humans (namely juvenile hemochromatosis), now allows the inventors to establish, for the first time, that hemojuvelin, the HFE2A Gene and HFE2A Polypeptide are useful as therapeutic targets in humans for the treatment of diseases of iron metabolism. The words "therapeutic target" are intended to mean that therapeutic intervention is achieved with therapeutic agents that modulate the activity of the gene or protein. "Modulate" means to increase, to decrease, or to otherwise change the activity. Standard industrial processes are available to those skilled in the art to confirm the identity of the therapeutic agents which modulate the activity of the gene or protein, some of which are set out below.

In accordance with the foregoing, the present invention relates to a method for treating a disorder comprising administering to a person in need of such treatment an effective amount of a selective HFE2A agonist or antagonist, or a pharmaceutically acceptable salt thereof, or a pharmaceutical composition containing either entity.

In a preferred embodiment, said disorder is a disease of iron metabolism. In a further preferred embodiment, said administering is by oral or intravenous means.

Use of the HFE2A in Screening Assays for Identifying Therapeutic Agents and Classes of Potential Therapeutic Agents.

The present invention readily affords different means for identification of agents for treating diseases of iron metabolism according to their ability to modulate the activity of HFE2A. Exemplary assay methods useful for the identification of such compounds are detailed herein, although those skilled in the art will be aware of alternative means.

In one series of embodiments described in some detail below, assay methods involve testing libraries of chemical compounds, either one at a time or in combinations, in an assay format designed to measure a biological activity related to HFE2A. Those library compounds that modulate the biological activity in the desired fashion are thereby identified as therapeutic agents of the invention. In effect, a wide variety of compounds are sequentially tested against the assay to determine whether they influence a measurable biological activity of the assay. Assays may be based one or more of the diverse measurable biological activities of a gene or polypeptide corresponding to HFE2A.

"HFE2A activity" or "HFE2A biological activity" as used herein, especially relating to screening assays, is to be interpreted broadly and contemplates all directly or indirectly measurable and identifiable biological activities of the HFE2A gene, gene products and HFE2A Polypeptide. Relating to the purified HFE2A Polypeptide protein, HFE2A Polypeptide activity includes, but is not limited to, all those biological processes, interactions, binding behavior, binding-activity relationships, pKa, pD, enzyme kinetics, stability, and functional assessments of the protein. Relating to HFE2A Polypeptide activity in cell fractions, reconstituted cell fractions or whole cells, these activities include, but are not limited the rate at which HFE2A Polypeptide performs any measurable biological characteristic and all measurable consequences of these effects, including cell growth, development or behavior and other direct or indirect effects of HFE2A Polypeptide activity. Relating to HFE2A genes and transcription, HFE2A activity includes the rate, scale or scope of transcription of genomic DNA to generate RNA; the effect of regulatory proteins on such transcription, the effect of modulators of such regulatory proteins on such transcription; plus the stability and behavior of mRNA transcripts, post-transcription processing, mRNA amounts and turnover, all measurements of expression and translation of the mRNA into polypeptide sequences, and all measurements of protein expression levels or dynamics. Relating to HFE2A activity in organisms, this includes but is not limited biological activities which are identified by their absence or deficiency in disease processes or disorders caused by aberrant HFE2A biological activity in those organisms. Some of the known or suggested biological activities are set out in the description of HFE2A provided in the specification, however those skilled in the art will be able to identify further measurable activities of HFE2A with routine techniques. Broadly speaking, HFE2A biological activity can be determined by all these and other means for analyzing biological properties of proteins and genes that are known in the art.

It is also recognized that those skilled in the art may prefer to use forms of HFE2A corresponding to the sequences disclosed herein, although not necessarily the same. For example, while screening assays preferably employ HFE2A from human, mouse, rat or fugu, other assays may utilize HFE2A from a different organism, preferably a vertebrate, and most preferably from a mammalian species. Thus the invention encompasses the use of, including but not limited to, sheep, dog, cow or horse HFE2A, for the same purposes as set out more specifically herein for human HFE2A. The shared technical features of these forms of HFE2A, are that, when expressed, they have similar biological activity, and that they share functional similarity with HFE2A, as the case may be, such as may be determined by those skilled in the art. The HFE2A gene and/or HFE2A Polypeptide according to the invention may also be obtained from other mammalian species, other vertebrates, invertebrates and microorganisms based on the disclosure herein.

Thus, the polynucleotides for use in the screening assays of the invention that "correspond to" the polynucleotide encoding HFE2A (processed or unprocessed, including naturally occurring splice variants and alleles) are at least 40%, preferably at least 50%, more preferably at least 60%, especially at least 70%, even more preferably at least 80%, or even at least 85%, most preferably at least 90%, or even at least 95%, or most especially at least 98%, with the especially preferred embodiment of identical to, and especially having the sequence of, an RNA that would be encoded by, or be complementary to, such as by hybridization under reasonably stringent conditions, with an HFE2A polynucleotide (SEQ ID NO: 1-9, or 13-22). In addition, HFE2A protein sequences encoding the same polypeptides as any of the nucleic acid sequences corresponding to HFE2A, regardless of the percent identity of such sequences, are also specifically contemplated by any of the methods of the present invention that rely on any or all of said sequences, regardless of how they are otherwise described or limited. Thus, any such sequences are available for use in carrying out any of the methods disclosed according to the invention. Such sequences also include any open reading frames, as defined herein, present within an HFE2A polynucleotide.

Because of the processing that may take place in transforming the initial RNA transcript into the final mRNA, the sequences disclosed herein may represent less than the full genomic sequence. They may also represent sequences derived from alternate splicing of exons. Consequently, the genes present in the cell (and representing the genomic sequences) and the sequences disclosed herein, which are mostly cDNA sequences, may be identical or may be such that the cDNAs contain less than the full complement of exons found in the genomic sequence. Such genes and cDNA sequences are still considered corresponding sequences because they both encode similar RNA sequences. Thus, by way of non-limiting example only, a gene that encodes an RNA transcript, which is then processed into a shorter mRNA, is deemed to encode both such RNAs and therefore encodes an RNA corresponding to an HFE2A sequence as disclosed herein. (Those skilled in the art understand that the word "encode" and its derivatives mean, in this field "can be transcribed into" or "can be translated into"). Thus, the sequences disclosed herein correspond to genes contained in the cells and are used to determine relative levels of transcription because they represent the same sequences or are complementary to RNAs encoded by these genes. Such genes also include different alleles and splice variants that may occur in the cells used in the processes of the invention.

As used herein, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula:

Percent Identity=100[1−(C/R)]

wherein C is the number of differences between the Reference Sequence and the Compared Sequence over the length of alignment between the Reference Sequence and the Compared Sequence wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the hereinabove calculated Percent Identity is less than the specified Percent Identity.

Where context indicates that sequences have been analyzed using the NCBI Blast tools, reports of sequence score, alignment, identity %, postive % and gaps % have been generated based on these calculations: For the segment pair, the alignment score is the sum of the scoring matrix values. The theory of amino acid substitution matrices is described in [1], and applied to DNA sequence comparison in [2]. The number of positives is the number of residues for which the alignment score has a positive value. Experimentation has shown that the BLOSUM-62 matrix [3] is among the best for detecting most weak protein similarities. [1] Altschul, S. F. (1991) "Amino acid substitution matrices from an information theoretic perspective." J. Mol. Biol. 219:555-565. [2] States, D. J., Gish, W. & Altschul, S. F. (1991) "Improved sensitivity of nucleic acid database searches using application-specific scoring matrices." Methods 3:66-70. [3] Henikoff, S. & Henikoff, J. G. (1992) "Amino acid substitution matrices from protein blocks." Proc. Natl. Acad. Sci. USA 89:10915-10919.

As used herein, the terms "portion," "segment," and "fragment," when used in relation to polypeptides, refer to a continuous sequence of nucleotide residues, sequence forms a subset of a larger sequence. Such terms include the products produced by treatment of said polynucleotides with any of the common endonucleases, or any stretch of polynucleotides that could be synthetically synthesized. These may include exonic and intronic sequences of the corresponding genes.

The instant invention provides numerous assays which measure an activity of HFE2A and are useful for the testing of compounds to identify which ones affect such activity. In terms of formatting the assays, the assays may use whole cells, cell extracts or reconstituted cell extracts, or purified or semi-purified proteins, or they may be larger scale tissue or whole animal assays. Common assays use measurements based on fluorescence, luminescence, radioactivity, or other measures of protein or gene transcript levels, amounts, or stability. Polypeptide assays may also include those wherein the HFE2A polypeptide is attached to a solid support, such as a resin or other polymer, especially where this is part of a column procedure for determining activity. Alternatively, batch procedures may also be used.

In one aspect, the present invention relates to a method for identifying an agent that modulates the activity of an HFE2A polypeptide, comprising:

a) contacting a test compound with an HFE2A polypeptide and under conditions supporting an activity of said polypeptide; and b) determining a change in said activity of said HFE2A polypeptide as a result of said contacting, wherein a change in the activity identifies said test compound as an agent that modulates the activity of an HFE2A-polypeptide.

In a preferred embodiment, said gene has the sequence of SEQ ID NO: 1-9.

In a preferred embodiment, the observed change in activity in step (b) is a decrease or an increase in activity, most preferably wherein said change in activity is the result of binding to said polypeptide by said chemical agent of step (b). In a preferred embodiment, such agents are useful for treating a disease of iron metabolism.

In other preferred embodiments, the polypeptide is part of an intact cell, preferably a mammalian cell, and which may be a recombinant cell. For HFE2A, cells of greatest interest include macrophages, hepatocytes, intestinal cells, heart cells (especially atrial cells), pancreatic cell, skeletal muscle cell and cells of the bone marrow, although cells from other tissues may be employed. In one such embodiment, said cell has been engineered to comprise said polypeptide, including by genetic engineering, especially where the cell does not possess the polypeptide absent said engineering. Thus, the present invention specifically contemplates embodiments in which the cell is engineered by other than genetic engineering, such as where the activity of a polypeptide is to be enhanced and the cell has been engineered to contain, or have on its surface, said polypeptide but wherein the polypeptide is present due to physical insertion of the polypeptide into the membrane or cytoplasm of the cell and not through expression of a gene contained in the cell. Methods well known in the art, such as use of polyethylene glycol, viruses, and the like, are available to effect such insertions and the details of such procedures need not be further described herein.

In one preferred embodiment of such method, the polypeptide is a polypeptide that reacts with an antibody that reacts with, or is specific for, a polypeptide having an amino acid sequence at least 95% identical to, more preferably at least 98% identical to, the sequence of SEQ ID NO: 10-12 and where any difference in amino acid sequence is due only to conservative amino acid substitutions. In an especially preferred embodiment, the polypeptide has the amino acid sequence of SEQ ID NO: 10-12.

The HFE2A Polypeptide assays of the invention may employ compound screening technology such as (but not limited to) the ability of various dyes to change color, or fluorescent signaling/quenching in response to changes in assay conditions resulting from the activity of the polypeptides. Compound screening assays can also be based upon the ability of test compounds to modulate the interaction of the target peptide (HFE2A Polypeptide) and known or discovered interacting proteins or protein receptors. Such interacting proteins can be identified by a variety of methods known in the art, including, for example, radioimmunoprecipitation, co-immunoprecipitation, use of epitope-tagged constructs in pull down experiments, co-purification by extraction and chromatography techniques, and yeast two-hybrid screening. Such interactions can be further assayed by means including but not limited to direct detection methods such as surface plasmon resonance, fluorescence with fluorophores or fluorochromes and quenching with chromophores, radiolabelled proteins, fluorescence polarization, confocal fluorescence imaging or scintillation proximity techniques. Indirect interactions may also be monitored through cell viability assays, second messenger reporting such as, G-protein coupled receptor assays, cAMP detection, nitric oxide synthase, phosphodiesterase activity, or lipid modification such as sphingomyelinase, inositol triphosphate assays.

Agents that have the effect of modulating the half-life of HFE2A Polypeptide are also useful for treating diseases of iron, metabolism. By way of non-limiting example, an assay for this kind of agent comprises cells expressing a wild-type HFE2A Polypeptide wherein such polypeptides are transiently metabolically labeled during translation, contacted with a candidate compound, and the half-life of the polypeptide is determined using standard techniques. Compounds that modulate the half-life of the polypeptide are useful compounds in the present invention.

In one such assay for which the polypeptides encoded by genes disclosed herein are useful, the purified or semi-purified HFE2A polypeptide (or a fragment thereof or an epitope-tagged form or fragment thereof is bound to a suitable support (e.g., nitrocellulose or an antibody or a metal agarose column in the case of, for example, a his-tagged form of said polypeptide). Binding to the support is preferably done under conditions that allow proteins associated with the polypeptide to remain associated with it. Such conditions may include use of buffers that minimize interference with protein-protein interactions. If desired, other proteins (e.g., a cell lysate) are added, and allowed time to associate with the polypeptide. The immobilized polypeptide is then washed to remove proteins or other cell constituents that may be non-specifically associated with it the polypeptide or the support. The immobilized polypeptide can then be used for multiple purposes. In a compound screening embodiment, such as that provided by Neogenesis Pharmaceuticals, Inc. (Cambridge, Mass.) the bound HFE2A Polypeptide will be employed in an automated ligand identification system, with low, medium or high-throughput capacity. In this case a pool of test compounds are exposed to HFE2A under conditions (i.e. buffers, temperatures, etc.) which promote specific binding of the test compounds to the protein. Compounds with non-specific binding are separated from the mixture. HFE2A/ligand complexes are then collected, and bound ligands are released and measured by mass spectrometer. A data analysis system correlates mass data with the list of compound masses included in the original test compound mixture. In an alternative embodiment, compounds can be tested for their ability to interfere with interactions between HFE2A Polypeptide and other bound molecules (which are presumably HFE2A Polypeptide interacting proteins). Compounds which can successfully displace interacting proteins are thereby identified as HFE2A Polypeptide modulating agents of the invention. Other well known protein binding assays, which use purified or semi-purified target protein, can also be employed to identify test compounds with specific binding affinity for the protein.

In an alternative embodiment designed to identify HFE2A Polypeptide interacting proteins, the immobilized polypeptide is dissociated from its support, and proteins bound to it are released (for example, by heating), or, alternatively, associated proteins are released from the polypeptide without releasing the latter polypeptide from the support. The released proteins and other cell constituents can be analyzed, for example, by SDS-PAGE gel electrophoresis, Western blotting and detection with specific antibodies, phospho-amino acid analysis, protease digestion, protein sequencing, or isoelectric focusing. Normal and mutant forms of such polypeptide can be employed in these assays to gain additional information about which part of the polypeptide a given factor is binding to. In addition, when incompletely purified polypeptide is employed, comparison of the normal and mutant forms of the protein can be used to help distinguish true binding proteins. Such an assay can be performed using a purified or semipurified protein or other molecule that is known to interact with a polypeptide encoded by an HFE2A polynucleotide.

This assay may include the following steps.

1. Harvest the encoded polypeptide and couple a suitable fluorescent label to it;

2. Label an interacting protein (or other molecule) with a second, different fluorescent label. Use dyes that will produce different quenching patterns when they are in close proximity to each other versus when they are physically separate (i.e., dyes that quench each other when they are close together but fluoresce when they are not in close proximity);

3. Expose the interacting molecule to the immobilized polypeptide in the presence or absence of a compound being tested for its ability to interfere with an interaction between the two; and 4. Collect fluorescent readout data.

An alternative assay for such protein interaction is the Fluorescent Resonance Energy Transfer (FRET) assay. This assay can be performed as follows.

1. Provide the encoded protein or a suitable polypeptide fragment thereof and couple a suitable FRET donor (e.g., nitro-benzoxadiazole (NBD)) to it;

2. Label an interacting protein (or other molecule) with a FRET acceptor (e.g., rhodamine);

3. Expose the acceptor-labeled interacting molecule to the donor-labeled polypeptide in the presence or absence of a compound being tested for its ability to interfere with an interaction between the two; and 4. Measure fluorescence resonance energy transfer.

Quenching and FRET assays are related. Either one can be applied in a given case, depending on which pair of fluorophores is used in the assay.

The description of the HFE2A provided herein teaches a wide variety of biological activities of HFE2A that may be useful for the development of low, medium or high-throughput screening assays.

One useful biological activity that works for a variety of assays is ligand binding (i.e. assays which either inhibit or enhance HFE2A binding with a ligand). The hepcidin protein (OMIM: 606464; See Roetto, A. et al. 2003. *Nature Genet.* 33: 21-22) may be a ligand of HFE2A. Those skilled in the art may find other ligands. Assays based on whole cells, cell extracts or purified proteins may be developed which-measure the capacity of a test compound to inhibit or enhance HFE2A binding with a specific ligand.

Cell function assays can be designed. In these assays, a measurable cell function which is dependent on HFE2A activity can be measured to determine inhibition or enhancement by test compounds. Such functions include cell growth assays, such as where compounds are evaluated for their ability to influence axonal growth, in assays such as those described in PCT patent publication WO 02/051438, incorporated herein by reference in its entirety. Based on the presence of RGD and von Willibrand factor-like domains, HFE2A may be involved in cell-cell adhesion. An assay can be designed which relies on the biological activity of HFE2A induced adhesion, and measures a test compound's ability to modulate adhesion.

In other cell based assays, an HFE2A protein response is first calibrated. For example HFE2A may modulate release of iron by macrophages to transferrin. Or, HFE2A may modulate transport of iron across a CaCo2 membrane. Alternatively, HFE2A may induce a change in NRAMP2 iron transport behavior in an assay. One may assay for compounds which modulate these induced responses to HFE2A and thereby find a modulator of a biological activity of HFE2A. Signaling assays can be developed based on possible functions of HFE2A as a signaling molecule. Iron transport assays that may be adapted include iron uptake in an HFE-CHO cell model for duodenal crypt cells. This can be adapted to assay in 96-well plates wherein test compounds will reduce iron uptake. Similarly, test compounds may inhibit 59Fe-bound transferrin uptake in human hepatoma cells (HLF). Assays that may be suitable for adaptation include those described in Su, M. A. et al. Blood, Vol. 92 No. 6 (Sep. 15), 1998: pp. 2157-2163; Nunez M T, et al. J Nutr 1996 September; 126 (9):2151-8; Tandy S, et al. J Biol Chem 2000 Jan. 14; 275(2): 1023-9; or Feeney G P and Worwood M. Biochim Biophys Acta 2001 Apr. 23; 1538(2-3):242-51). HFE2A shares sequence similarity and similar structural domains with the human repulsive guidance molecule (RGM), (FIG. 3) and to chicken RGM-like molecule (FIG. 5). RGMs are a family of proteins involved in neural development and immune response (see WO 02/051438), though assignment of at least some of these functions to HFE2A protein must be considered doubtful, as protein and mRNA expression is not found in neural cells. In any case, related proteins are known to act locally on the cell membrane as receptors, initiating intracellular signals, and systemically as a cleaved soluble protein. Like the chicken RGM, HFE2A has a putative extracellular cleavage site suggesting that it acts as a soluble peptide. One proposed mechanism of action could be that this secreted molecule interacts with proteins on the basal-lateral surface of the intestinal epithelial cells, like hepcidin, and modulates the apical surface uptake of iron from diet. This interaction could be direct, at the basal surface of the intestinal cells, or via an upstream interaction resulting in modulating iron uptake. This direct or indirect effect can be assayed in a cell culture system.

An example of a compound screening assay which relies on an HFE2A induced response (i.e. an HFE2A biological activity) is a Caco2 HFE2A induced iron transport assay. Caco2 cells are a human colorectal carcinoma cell line and considered the standard for measuring intestinal absorption. These cells grown to confluence form distinct apical and basalatoral surfaces and tight junctions. Grown on permeable membranes in Transwell plate inserts, Caco2 cells become polarized with the basalatorial surface of the cell on the membrane and exposed to the B chamber solutes, while the apical side of the cell is exposed to solutes in the A chamber. This system is useful to measure active transport of iron through the intestinal epithelium from A to B, mimicking transport from the intestinal lumen through the cell to the blood. A response to HFE2A can be induced by adding HFE2A to the B (baso-lateral) chamber of the CaCo2 assay. Recombinant HFE2A can be produced in mammalian cells and the purified protein directly added to the B chamber. Alternatively, cultured cells can be transfected with HFE2A constructs and then express HFE2A protein. Appropriate cells for transfection would be HepG2 or RAW cells, human liver carcinoma cells or mouse macrophage cells, respectively. These two cell types are known to be involved in iron metabolism, and likely express HFE2A. The media from these transfected "donor" cells containing HFE2A can now be applied to the B chamber of the Caco2 cells, "acceptor" of the conditioned media, and iron absorption from the A chamber can be monitored. The transfected donor cells could also be grown on the bottom of the B chamber surface, thus directly releasing HFE2A into the B chamber, within millimeters from the basal surface of the acceptor cells.

Whether HF2A acts as a receptor, intracellular signal molecule or secreted protein, this multicellular communication system can be applied to measure an HFE2A induced response. The assay may measure iron transport, iron uptake from the A chamber, iron absorption and/or cell secretion of iron to the B chamber. This cell communication system can thereafter be applied to primary drug compound screening for iron modulation in intestinal absorption.

Using whole cells or cell extracts, assays can be developed for compounds which increase or decrease GPI cleavage or secretion of HFE2A or for compounds which increase or decrease N-glycosylation of HFE2A. Assays that measure compounds which modulate post-translational modifiers of HFE2A can be used to identify potential therapeutic agents.

Some assays preferably employ purified or semi-purified HFE2A protein assays. This protein may be the GPI-linked form, or the cleaved, soluble form. $I^{125}$ labelled HFE2A may be useful for these assays. Such assays include aggregation, assays which are designed based on the tendency of HFE2A to aggregate or homodimerize via the RGD or von Willibrand factor-like domains. In this assay, compounds are tested for their ability to enhance or prevent aggregation of homophilic dimerization domains. In this case, the protein-protein interaction assays above can use two pools of HFE2A, each labelled with a different fluorophore. In some embodiments a GPI-cleaved form of HFE2A may be used with the GPI-linked form. An alternate semi-purified format includes yeast 2-hybrid and/or phage display formats, wherein HFE2A binding regions are incorporated into both bait and prey vectors. This format would provide a moderately high throughput screening assay, suitable for radioimmunoassay or plate format.

In addition it is to be noted that HFE2A may interact with other known proteins of the iron metabolic pathway: Transferrin, Tf receptor, Hfe, hepcidin, p97 or other iron transporters, and receptors thereof. This interaction is a useful activity which may be used as the basis for a screening assay.

Additionally, drug screening assays can also be based upon polypeptide functions deduced upon antisense interference with the gene function. Intracellular localization of HFE2A, or effects which occur upon a change in intracellular localization of such proteins, can also be used as an assay for drug screening.

In accordance with the foregoing, the present invention provides the amino acid sequence of a protein, designated hemojuvelin or HFE2A, that is found in tissues of the human body (for example, SEQ ID NO: 10-12 from humans) and which is associated with hereditary transmission of juvenile hemochromatosis. In addition, several mutations, have been found in this sequence derived from individuals found to have juvenile hemochromatosis. Thus, agents that interact with hemojuvelin or HFE2A represent candidate compounds for evaluation as therapeutic agents of the invention.

Another broad category of screening assays is transcription assays. These assays seek to identify compounds which modulate (i.e. increase or decrease) transcription of the HFE2A gene. Relating to transcription assays, in one aspect the present invention relates to a method for identifying an agent that modulates the activity of a polynucleotide whose transcription contributes to amelioration of a disease of iron metabolism, comprising:

a) contacting under physiological conditions a chemical agent with a polynucleotide corresponding to the promoter region of HFE2A (in a preferred embodiment, the promoter has the sequence of SEQ ID NO: 19); and b) detecting a change in the transcription of said polynucleotide as a result of said contacting;

thereby identifying an agent that modulates transcription of said polynucleotide or gene activity.

Such modulation is preferably a decrease or an increase in transcription.

In preferred embodiments, such transcription is measured by measuring the amount of a transcription product. In a convenient embodiment, the promoter region of HFE2A is operably linked to a reporter gene, that is, a gene whose transcription is conveniently measured (for example, reporter genes such as Green Fluorescent Protein, luciferase, chloramphenicol acetyl-transferase (CAT), and the like).

In preferred embodiments, the polynucleotide whose transcription is to be measured or monitored is present in an intact cell, preferably a mammalian cell, most preferably a cell selected from among macrophages, hepatocytes, intestinal cells, hematopoietic cells, pancreatic cell, skeletal muscle cell and other cells of the bone marrow, neurological, CNS or spinal cells, although cells from other tissues may also be used. In additional preferred embodiments, such an intact cell is a cell that has been engineered to comprise said polynucleotide, such as by genetic engineering, preferably wherein the cell does not express the subject gene or polynucleotide absent having been engineered to do so. Alternatively, non-recombinant cells can be employed, as for example, in cells of tissues or cell lines where the transcription of HFE2A is constitutive, or can be induced.

In accordance with the disclosure herein, upstream untranslated regions and promoter regions of HFE2A Gene are readily obtained from SEQ ID No. 19 or 22 and other publicly retrievable sequence databases. Such genomic or untranslated regions may be included in plasmids comprising the identified gene, such as in assays to identify compounds which modulate transcription thereof. In one such assay, the upstream genomic region is ligated to a reporter gene, and incorporated into a transcription plasmid. The plasmid is transfected into a cell, and the recombinant cell is exposed to test compound(s). Those compounds which increase or decrease the expression of the reporter gene are then modulators of the gene/protein, and are considered therapeutic agents of the invention.

The invention also claims recombinant cells engineered to express a polynucleotide or polypeptide as disclosed herein. The gene disclosed herein as being involved in HFE2A in an animal can be used, or a fragment thereof can be used, as a tool to express a protein, where such genes encode a protein, in an appropriate cell in vitro, or can be cloned into expression vectors which can be used to produce large enough amounts of protein to use in in vitro assays for drug screening. Alternatively, the expression construct may employ the genomic promoter region of HFE2A and link it to a gene, such as a reporter gene, whose expression level is easily measured. Expression systems which may be employed include baculovirus, herpes virus, adenovirus, adeno-associated virus, bacterial systems, and eucaryotic systems such as CHO cells. Naked DNA and DNA-liposome complexes can also be used. The invention thus claims recombinant cell lines containing a heterologous HFE2A gene.

Such recombinant cells may be used in transcription assays for analyzing the levels of transcription of HFE2A Gene or a suitable reporter gene after contacting said cells with agents that may have therapeutic properties. The levels of gene transcription can be quantified by Northern blot analysis or RT-PCR, or, alternatively, by measuring the amount of protein produced, by one of a number of methods known in the art, or by measuring the levels of biological activity of polypeptides encoded thereby or other genes. In this way, the gene transcription can serve as a marker, indicative of the physiological response of the cells to the agent. Accordingly, this response state may be determined before, and at various points during, treatment of the individual with the agent.

Recombinant cell lines are also preferred for the preparation of purified protein, if a purified protein assay is desired. Those skilled in the art are capable of producing recombinant cell lines and extracting protein fractions containing highly purified proteins. These samples can be used in a variety of binding assays to identify compounds which interact with the proteins. Compounds that interact are therapeutic agents of the invention, or analogs thereof.

Target selectivity is an important aspect of the development of therapeutic agents. The present invention specifically contemplates the identification of chemical agents, especially small organic molecules, that agonize or antagonize the transcription of HFE2A Gene, as defined herein, or the activity of the HFE2A Polypeptide (such as SEQ ID NO: 10-12 from humans) encoded thereby, with high specificity and that have little or no effect on other genes and/or polypeptides.

Thus, in one such preferred embodiment, the methods disclosed herein for identifying an agent that modulates, preferably inhibits, expression of a gene corresponding to HFE2A, preferably having the sequence of SEQ ID NO: 1-9 from humans, or on the activity of a polypeptide encoded thereby, comprises first identifying such agent and then testing such agent for effects on expression or activity of at least one other gene or polypeptide, preferably a gene or polypeptide with important physiological consequences that are preferably not disturbed by therapeutic intervention, and demonstrating little or no effect.

In another aspect, the invention provides a method for computationally identifying a compound of the invention. The method involves (a) determining the crystal structure of an active site of a HFE2A Polypeptide protein (i.e. through x-ray crystallography or other techniques); and (b) through computational modeling, identifying a compound which interacts with the active site, thereby identifying a compound, or its analog, as a compound which is useful for modulating the activity of such a polypeptide. This process is sometimes referred to as in silico screening. Sophisticated software for testing the probability of test compounds to interact with the target protein, which can test tens of millions of computer generated compounds, Is available to those skilled in the art.

Potential therapeutic compounds identified using the methods of the invention are usually tested in animal model systems to confirm the putative efficacy. Thus, in a further aspect, the present invention relates to a method for identifying a therapeutic agent, comprising:

a) administering to an animal an agent found to have activity using an assay or screening method as disclosed herein, and b) detecting in said animal a change in iron metabolism due to said administering, thereby identifying an agent for the treatment a disease of iron metabolism.

Those skilled in the art are aware that typical measurements of iron metabolism that may be modulated in animal models (i.e., as a result of treatment with a potential therapeutic agent) include transferrin saturation, hepcidin levels, radioactive iron uptake in the gut, liver iron content, whole body iron content, anemia indices. Specialized mouse models for study include anemic mice, iron overload mice, hemochromatosis mice (hfe/hfe), Hpx mice (hypotransferrinemic mouse), and others.

In a further aspect, the present invention relates to a method for treating a condition in an animal afflicted with a disease of iron metabolism comprising administering to said animal an effective amount of an agent first identified by an assay method of the invention. Preferably, said animal is a human patient, such as a patient afflicted with a disease of iron metabolism.

The screening assays of the invention thus simplify the evaluation, identification and development of therapeutic agents for the treatment of diseases of iron metabolism.

The invention also includes antibodies and immuno-reactive substances which target, interact with or bind to hemojuvelin, HFE2A Polypeptide or epitopes thereof. Polypeptides encoded by the polynucleotides disclosed herein can be used as an antigen to raise antibodies, including monoclonal antibodies. Such antibodies will be useful for a wide variety of purposes, including but not limited to, therapeutic agents, functional studies, drug screening assays, and/or diagnostic agents. Monitoring the influence of agents (e.g., small organic compounds) on the expression or biological activity of the HFE2A polypeptides identified according to the invention can be applied not only in basic drug screening, but also in clinical trials. For example, the effectiveness of an agent determined by a screening assay as described herein to increase or decrease gene transcription, protein levels, or biological activity can be monitored in clinical trails of subjects exhibiting symptoms of diseases of iron metabolism due to inadequate gene transcription, protein levels, or biological activity (for example, the individuals studied herein. Alternatively, the effectiveness of an agent determined by a screening assay to modulate transcription of HFE2A Gene, as well as structurally and functionally related genes, including genes with high homology thereto, and including protein levels, or biological activity can be monitored in clinical trials of subjects exhibiting decreased altered gene transcription, protein levels, or biological activity. In such clinical trials, the transcription or activity of the genes or polypeptides disclosed herein and, preferably, other genes that have been implicated in, for example, iron metabolism, can be used to ascertain the effectiveness of a particular drug.

In a preferred embodiment, the present invention provides a method for monitoring the effectiveness of treatment of a subject with an agent (e.g., an agonist, antagonist, peptidomimetic, protein, peptide, antibody, nucleic acid, small molecule, or other drug candidate identified by the screening assays described herein) including the steps of (i) determining that a patient requires treatment for an iron metabolism disease or disorder; (ii) administering an effective amount of an agent identified using one of the screening assays disclosed herein; (iii) ascertaining an improvement in iron metabolism following said administration and (vi) altering the administration of the agent to the subject accordingly. For example, increased administration of the agent may be desirable to decrease the expression or activity of gene or encoded polypeptide, i.e., to increase the effectiveness of the agent.

Where the patient is non-human, biopsy samples can be taken to show a decrease in gene transcription, such as by measuring levels of protein, mRNA, or genomic DNA post-administration samples and comparing the level of expression or activity of said protein, mRNA, or genomic DNA in the pre-administration sample with that of the corresponding post administration sample or samples, thereby showing the effects of drug administration on one or more of the genes disclosed herein and concomitant reduction in problems with iron metabolism.

Purified or semi-purified HFE2A protein, or fragments thereof, or proteins corresponding to HFE2A, and any biochemically modified versions thereof, are themselves therapeutic agents of the invention. Recombinant or non-recombinant forms of these proteins or fragments can be administered to persons in need thereof for the treatment of disorders, such as diseases of iron metabolism. Those skilled in the art are familiar with techniques for generating such agents, and for determining conditions of administration.

Specific compounds which will modulate the gene expression or gene transcript levels in a cell of HFE2A include antisense nucleic acids, ribozymes and other nucleic acid compositions which specifically hybridize with the HFE2A gene (including exons or introns of such genes, promoters, 3'-tails, and the like). These specific compounds are compounds of the invention, and are useful for treating the diseases discussed previously. Design and manufacturing of such compounds are well known to those skilled in the art.

Specific compounds which modulate the activity of HFE2A include antibodies (polyclonal or monoclonal) and modified antibodies or fragments of antibodies which specifically bind to an epitope of said polypeptide. These specific compounds are compounds of the invention, and are useful for treating the diseases previously discussed. Design and manufacturing of such compounds are well known to those skilled in the art. In particular, humanized antibodies tend to be preferred, such as those generated using techniques provided by Abgenix, Inc. (Freemont, Calif.), Medarex, Inc. (Princeton, N.J.), Protein Design Labs, Inc. (Freemont, Calif.), Genentech (South San Francisco, Calif.), and others.

Specific compounds which modulate the activity of HFE2A in the body include gene therapy vectors comprising all or a part of the HFE2A gene sequence or mutant HFE2A sequence. As is well known to those skilled in the art, gene therapy allows the delivery of HFE2A in an organism to cells where it is taken up and expressed, thus changing the level or amount of HFE2A Polypeptide protein in such cell. These vectors thereby modulate the activity of HFE2A in the body and are useful for the therapeutic indications disclosed herein.

Specific compounds which modulate the activity of HFE2A in the body include small organic molecules. Such compounds may be naturally occurring, or they may be synthetic. Collections and combinatorial libraries of such compounds are widely available from commercial sources. As know to those skilled in the art, a screening assay, such as the assays disclosed in the instant specification, can be easily adapted to identify therapeutic agents which have the desired HFE2A modulating ability. Agonists, antagonists, or mimetics found to be effective at reducing disorders of iron metabolism may be confirmed as useful in animal models (for example, mice, chimpanzees, etc.). In other embodiments, treatment with a compound of the invention may be combined with other therapeutic agents to achieve a combined, possibly even synergistic, effect.

Candidate modulators may be purified (or substantially purified) molecules or may be one component of a mixture of compounds (e.g., an extract or supernatant obtained from cells). In a mixed compound assay, gene expression is tested against progressively smaller subsets of the candidate compound pool (e.g., produced by standard purification techniques, such as HPLC or FPLC) until a single compound or minimal compound mixture is demonstrated to modulate gene or protein activity or expression in a manner having therapeutic effects.

Lead Optimization and Analog Development and Selection

In general, novel drugs having therapeutic properties are identified from libraries, possibly large libraries, of both natural product or synthetic (or semi-synthetic) extracts or chemical libraries according to methods known in the art. Those skilled in the field or drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

De-replication (e.g., taxonomic de-replication, biological de-replication, and chemical de-replication, or any combination thereof) or the elimination of replicates or repeats of materials already known for their therapeutic activities may be employed whenever possible.

When a crude extract is found to have therapeutic activities, further fractionation of the positive lead extract is possible to isolate chemical constituent responsible for the observed effect. Thus, the goal of the extraction, fractionation, and purification process is the careful characterization and identification of a chemical entity within the crude extract having such therapeutic activities. The same assays described herein for the detection of activities in mixtures of compounds can be used to purify the active component and to test derivatives thereof. Methods of fractionation and purification of such heterogeneous extracts are known in the art. If desired, compounds shown to be useful agents for the treatment of pathogenicity are chemically modified according to methods known in the art. Compounds identified as being of therapeutic value are subsequently analyzed using any standard animal model of an iron metabolism disorder known in the art.

In general, these screening methods provide a ready means for selecting either natural product extracts or synthetic compounds of interest from a large population (i.e. a chemical library, for example, one produced by combinatorial means) which are further evaluated and condensed to a few active core structures. Multiple analogs of such core structures may be developed and tested to identify those preferred analogs which have improved characteristics as therapeutic agents.

Improved analogs may also include compounds with improved stability, biodistribution, pharmacokinetics or other desirable features for therapeutic agents which are not directly related to modulation of the therapeutic target. In a preferred embodiment, the improved analog of the invention is effectively delivered, either by physiological means or assisted means, to cells of the body expressing the HFE2A Polypeptide protein. Analog compounds are systematically screened to evaluate whether they modulate the identified biological activity and those that effectively do so are then therapeutic agents, or further analogs thereof, according to the invention.

Therapeutic Agents and Uses Thereof

Those skilled in the art are familiar with the necessary steps for pre-clinical and human clinical trials which are used to establish efficacy and safety of the new chemical entities and compounds first identified by the invention for use in treating the diseases mentioned herein.

Compounds first identified as useful therapeutic agents using one or more of the assays of the invention may be administered with a pharmaceutically-acceptable diluent, carrier, or excipient, in unit dosage form. Conventional pharmaceutical practice may be employed to provide suitable formulations or compositions to administer such compositions to patients. Although oral administration is preferred, any appropriate route of administration may be employed, for example, intravenous, parenteral, subcutaneous, intramuscular, intracranial, intraorbital, ophthalmic, intraventricular, intracapsular, intraspinal, intrathecal, epidural, intracisternal, intraperitoneal, intranasal, or aerosol administration. Therapeutic formulations may be in the form of liquid solutions or suspension; for oral administration, formulations may be in the form of tablets or capsules; and for intranasal formulations, in the form of powders, nasal drops, or aerosols.

Methods well known in the art for making formulations are found in, for example, Remington: The Science and Practice of Pharmacy, (19th ed.) ed. A. R. Gennaro AR., 1995, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for agonists of the invention include ethylenevinyl acetate copolymer particles, osmotic pumps, implantable infusion systems, and liposomes. Formulations for inhalation may contain excipients, or example, lactose, or may be aqueous solutions containing, for example, polyoxyethylene-9-lauryl ether, glycocholate and deoxycholate, or may be oily solutions for administration in the form of nasal drops, or as a gel.

Combination therapies are also contemplated by the inventors. An therapeutic agent identified by one of the screening methods disclosed herein may be administered along with another agent intended to treat a coincident conditions, such as where therapeutic and antitumor agents are given together or contemporaneously.

The present invention also relates to a process that comprises a method for producing a product, such as by generating test data to facilitate identification of such product, comprising identifying an agent according to one of the disclosed processes for identifying such an agent (i.e., the therapeutic agents identified according to the assay procedures disclosed herein) wherein said product is the data collected with respect to said agent as a result of said identification process, or assay, and wherein said data is sufficient to convey the chemical character and/or structure and/or properties of said agent. For example, the present invention specifically contemplates a situation whereby a user of an assay of the invention may use the assay to screen for compounds having the desired enzyme modulating activity and, having identified the compound, then conveys that information (i.e., information as to structure, dosage, etc) to another user who then utilizes the information to reproduce the agent and administer it for therapeutic or research purposes according to the invention. For example, the user of the assay (user 1) may screen a number of test compounds without knowing the structure or identity of the compounds (such as where a number of code numbers are used the first user is simply given samples labeled with said code numbers) and, after performing the screening process, using one or more assay processes of the present invention, then imparts to a second user (user 2), verbally or in writing or some equivalent fashion, sufficient information to identify the compounds having a particular modulating activity (for example, the code number with the corresponding results). This transmission of information from user 1 to user 2 is specifically contemplated by the present invention.

In accordance with the foregoing, the present invention relates to a method for producing test data with respect to the modulation of HFE2A gene expression by a compound, comprising:
  (a) a genetic construct comprising a reporter gene operably linked to an HFE2A promoter under conditions supporting expression of said reporter gene;
  (b) determining a change in expression of said reporter gene as a result of said contacting, wherein said change shows modulation, and
  (c) producing test data with respect to the gene modulating activity of said test compound based on a change in expression of the determined genes indicating gene modulating activity.

In another such embodiment, the present invention relates to a method for producing test data with respect to the modulation of an HFE2A polypeptide activity by a compound, comprising:
  (a) contacting a test compound with an HFE2A polypeptide and under conditions promoting an activity of said HFE2A polypeptide;
  (b) determining a change in activity of said polypeptide as a result of said contacting, wherein said change shows modulation, and
  (c) producing test data with respect to the HFE2A polypeptide modulating activity of said test compound based on a change in an HFE2A polypeptide activity indicating modulating activity.

Diagnostics and Pharmacogenomics

In a further embodiment, the invention relates to diagnostic and pharmacogenomic compounds, kits and methods. This aspect relates to analysis HFE2A Gene (HFE2A, hemojuvelin gene) for the diagnosis, including prognosis of onset or severity of onset, of juvenile hemochromatosis, adult onset hemochromatosis, a disorder of iron metabolism, or in the selection of a therapeutic agent for a patient (i.e. pharmacogenomics). It also relates to the use of HFE2A diagnosis to classify patients having or at risk of having a disease of iron metabolism.

For example, nucleic acid analysis can be used to identify the HFE2A mutations disclosed herein, thus confirming the diagnosis of juvenile hemochromatosis.

Using the nucleic acid sequences disclosed in this invention, both the wild-type (non-disease associated) sequences (SEQ ID No. 1-9) and the disease associated (mutated) sequences (SEQ ID Nos. 14, 16, and 18), those skilled in the art are capable of developing numerous different types of nucleic acid diagnostic methods, compounds and kits. Techniques include DNA sequencing, hybridization probing, single stranded conformational analysis, PCR based techniques such as mismatch amplification, and myriad other well known methods. All such analysis can be performed on a small sample of blood, saliva, urine or other tissue provided by the patient.

Alternatively, using the protein sequences disclosed in this invention (SEQ ID No. 10-12) protein based analyses such as antibody based assays (Elisa, Radioimmunoassay and the like) can be employed to identify the expression, amount or presence or absence of a normal or mutant HFE2A protein (HFE2A Polypeptide), such as those mutant polypeptides that result from the mutations disclosed herein.

Gene transcription, both comparable and absolute, as well as biological activity, and mutational analysis can each serve as a diagnostic tool for a disease of iron metabolism; thus determination of the amount of HFE2A mRNA can be used to diagnose the presence or absence of a mutation correlated with such a disease.

Based on the instant invention, those skilled in the art will also be able to develop other biochemical, chemical and diagnostic assays of HFE2A, mutation which are suitable for use with animal tissue samples.

A valuable embodiment of the invention will be to use the diagnostic assays to classify patients having or at risk of having a disease of iron metabolism. There are many risk factors for diseases of iron metabolism, such as enhanced serum ferritin levels, transferrin receptor saturation, or identification of a mutation in a gene for hemochromatosis (i.e. the Hfe gene). Not all of these risk factors lead to the development of a disease of iron metabolism. Using the teaching of the invention, it is now possible to take patients at risk of having a disease of iron metabolism based on a known risk factor and further assessing them for mutations in HFE2A, wherein a mutation in HFE2A (in one or both copies of the gene) indicates a statistically greater chance of developing the disease of iron metabolism. This discovery particularly aids in diagnosis and prognosis of the risk of adult onset hemochromatosis, which correlates only loosely with the known mutations in the Hfe gene.

What follows is an example of the diagnostic benefit of HFE2A in relation to adult onset hemochromatosis. Nucleic acid or protein analysis used to identify HFE2A mutations disclosed herein, could be used to predict onset or severity of adult hemochromatosis. Adult hemochromatosis displays a wide variability in clinical penetrance. In some human subjects homozygous for HFE mutations there is early onset of a severe phenotype, while in other subjects homozygous for HFE mutations, they remain clinically normal. Assessment of HFE2A gene may be informative for which patients will manifest adult disease and which ones will remain relatively symptom free.

A patient was found to be heterozygous for a mutation in the Hfe1 gene at H63D. This mutation is considered a mild mutation which does not always result in onset of hemochromatosis. A second diagnostic test was then performed on the HFE2A gene. It revealed the following homozygous mutation:

| Mutation in HFE2a | Type | Sequence |
|---|---|---|
| c.569C>A, p.A190D | WT | gtccaaggagCttggcctcta (SEQ ID NO: 31) |
|  | MT | gtccaaggagAttggcctcta (SEQ ID NO: 32) |

The patient developed adult onset hemochromatosis. Thus, detection of mutations in HFE2A is useful in identifying and classifying patients at risk of developing hemochromatosis, because of a known risk factor (such as Hfe1 mutation), and determining which patients will develop the disease.

This invention therefore discloses a method of classifying a patient at risk of developing a disease of iron metabolism, comprising
  a) performing a first assessment for a disease of iron metabolism, and
  b) performing a diagnostic assay on HFE2A,
    wherein a finding of mutation in HFE2A classifies said patient as having a statistically higher risk of developing said disease.

Pharmacogenomics deals with clinically significant hereditary variations in the response to drugs due to altered drug disposition and abnormal action in affected persons (Eichelbaum, M., Clin. Exp. Pharmacol. Physiol., 23:983-985, 1996; Linder, M. W., Clin. Chem., 43:254-266, 1997). In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). Altered drug action may occur in a patient having a polymorphism (e.g., an single nucleotide polymorphism or SNP) in promoter, intronic, or exonic sequences of HFE2A Gene. Thus by determining the presence and prevalence of polymorphisms allow for prediction of a patient's response to a particular therapeutic agent.

This pharmacogenomic analysis can lead to the tailoring of drug treatments according to patient genotype, including prediction of side effects upon administration of therapeutic agents, particularly therapeutic agents for treating disorders disclosed in this specification. Pharmacogenomics allows for the selection of agents (e.g., drugs) for therapeutic or prophylactic treatment of an individual based on the genotype of the individual (e.g., the genotype of the individual is examined to determine the ability of the individual to respond to a particular agent).

Diagnostics employing a gene or protein corresponding to HFE2A Gene (HFE2A) can also be useful in selecting patients for clinical trials of a potential therapeutic agent. Patients can be stratified according to the DNA or protein sequence of HFE2A Gene and their response to drug treatment can be evaluated. Such stratification can greatly reduce the number of patients required to establish efficacy for a potential therapeutic agent.

The invention thus comprises compounds, reagents and kits which are designed to identify the presence or absence of mutations in the HFE2A gene.

EXAMPLE 1

Identification of the Genetic Mutation Responsible for Juvenile Hemochromatosis 2A (HFE2A)

3. We have collected ten Greek families including 13 individuals with JHH. Pedigrees of these families are shown in FIGS. 9a-9d. Of these families (JH3-12), five have been reported previously (JH3-7) (Papanikolaou, G. et al. *Linkage to chromosome* 1q in Greek families with juvenile hemochromatosis. Blood Cells Mol. Dis. 27, 744-749 (2001)). Only one family, JH7, is known to be consanguineous. We confirmed that the disease is consistent with linkage to 1q21 (HFE2A; OMIM 602390) in the new families by using 25 genotype markers, including six new microsatellite markers identified from genomic sequence. While the Build 31 human genome sequence assembly contains gaps and duplications, we were able to estimate the size of the linkage interval, and define the linkage boundaries and gene content based on existing sequence contigs. Homozygosity mapping in JH7 defined the limits of the candidate region in an ~1.7 Mb interval between markers CA3AL590452 (141595604-141595847 bp) and CA1AL596177 (143293543-143293826 bp). (The primer sequences for each marker are in Table 6).

Homozygosity in this region was also observed in affected individuals from seven families without known consanguinity. We obtained six different Greek haplotypes by constructing haplotypes using an additional 12 markers. Affected individuals from families JH3, 5, 6, 7, 10, 11 and 12 shared alleles for at least 6 of 7 markers in the linked interval. Affected individuals from JH4 and 8 displayed different homozygous haplotypes.

TABLE 6

| D No. | Forward Primer | Reverse Primer |
|---|---|---|
| CA3AL 590452 | cacttgagcccaggaatttg (SEQ ID NO: 55) | gactcactgcagccttgacc (SEQ ID NO: 56) |
| CA1AL 596177 | gtgtgctacaagtttgccgaat (SEQ ID NO: 57) | gcttgaaactgggagttgga (SEQ ID NO: 58) |

TABLE 6-continued

| D No. | Forward Primer | Reverse Primer |
|---|---|---|
| CA1AL 355505 | gggaaatggtcccataattcct (SEQ ID NO: 59) | cgccctgccAATATGTTCT (SEQ ID NO: 60) |
| D1S44 | GGTACTTAGCCTCGAAA TGAGA (SEQ ID NO: 61) | GTGTCACACAACTGGTT G GT (SEQ ID NO: 62) |

Identification of Mutations in HFE2A

Mutations in HFE2A, (LOC148738) ENSG00000168509, transcript ENST00000306561, Ensembl v.12.31.1, November, 2002.

We first sequenced one of three coding exons (ENSE00001277351, v.12.31.1) in this gene. Sequencing was initially limited to those probands that probably carried unique haplotypes, from families JH3 and 4. The first mutation identified was in JH4-203, a T to C transition in the 3' exon (c.842T>C, p. I281T). JH4-203 is homozygous for this SNP. Two siblings and one child, all unaffected, are heterozygous for this SNP. This SNP was not present in any other JH probands or family members and not present in 74 European and 74 Greek control chromosomes.

The second genetic variation identified within this exon is a G to T transversion (c.959G>T, p.G320V). This SNP was homozygous in the JH3 proband. The JH3 affected is homozygous for the c.959T allele and one unaffected sib is heterozygous for this SNP. This SNP was not present in 128 European and 37 Greek control chromosomes. After sequencing all family members of the 10 JH families, it was determined that this SNP is homozygous in the affected individuals from families JH5, JH6, JH7, JH10, and heterozygous in the JH11 proband and both parents of the JH12 proband.

A third variation, a deletion at nucleotide 1079 (c.1079delC, p.C361fsX366) was identified in the hornozygous state in the JH8. This results in 5 unique amino acids and a premature stop. This SNP was also present in the JH11 proband, indicating that this individual is a compound heterozygote.

Additional Information About the Sequences Disclosed in the SEQ ID Listing in This Specification:

LOC148738 Exons

Exons 1, 3a, 3b and 4 may also be found at Gene ENSG00000168509 (Ensembl) and REFSEQ NM_145277.1 (NCBI). Exon 2 may be inferred from an ensembl prediction based on the sequence AK098165.1.

To simplify sequence searching, exon sequence coordinates are provided below based on the NCBI 31 assembly of the human genome. The SEQ ID NOs for these are:

SEQ ID NO. 1—Exon1 ENSE00001155188
Start: 142000393, End: 142000541 Chr: 1
SEQ ID NO. 2—Exon2
Start: 142001790, End: 142001993 Chr:1
SEQ ID NO. 3—Exon3a ENSE00001155182
Start: 142002394, End: 142002430 Chr:1
SEQ ID NO. 4—Exon3b ENSE00001277320
Start: 142002394, End: 142002953 Chr: 1
SEQ ID NO. 7—Transcript 2 ENST00000317920
Exons 1, 3a, 4, translation_start: 208
SEQ ID NO. 8—Transcript 3 Exons 1, 3b, 4 translation_start: 392
SEQ ID NO. 9—Transcript 4 Exons 1, 2, 3b, 4 translation_start: 257

LOC148738 Translated Proteins

Protein 1 is the protein translation of Transcript 1 and Transcript 2 and is similar to the Ensembl protein ENSP00000320072 and the NCBI protein NP_660320.1. Protein 2 is the protein translation of Transcript 2 and may be found in the protein translation of AK098165.1. Protein 3 is similar to the predicted Ensembl Protein ENSP00000304614. SEQ ID NOs are as follows:

SEQ ID NO. 10—Protein 1 ENSP00000320072
Translated from Transcript 1 and Transcript 2
SEQ ID NO. 11—Protein 2—
Translated from Transcript 3
SEQ ID NO. 12—Protein 3 ENSP00000304614
Translated from Transcript 4

HFE2A Promoter Sequences for Human, Mouse and Rat

For SEQ ID Nos. 19-21, the promoter sequence is deemed to begin 1500 bp 5' of the transcriptional start site.

Human Genomic DNA fragment including HFE2A promoter region and exons have SEQ ID NOs as follows:

SEQ ID NO. 22—Human Genomic DNA fragment including HFE2A promoter region and exons
SEQ ID NO. 23—similar to gi|24308189|ref|NP_064596.1|Human RGM
SEQ ID No. 24—Similar to ENSESTP00000023393 Human HFE2A paralog on chromosome 5, sequence starting from first methionine
SEQ ID NO. 25—Similar to ENSMUSESTP00000016634 Mouse HFE2A
SEQ ID No. 26—Similar to gi|21758120|dbj|BAC05248.1| Rat HFE2A annotated as from *Homo sapiens* but nucleotide sequence identified as from rat
SEQ ID No. 27—Similar to SINFRUP00000138308 Fugu HFE2A, N-terminus not defined
SEQ ID No. 28—Similar to gi|22651834|gb|AAM95449.1| Chicken RGM Those skilled in the art will be familiar with numerous variations of the compositions and methods disclosed above, all of which are encompassed by the claims further set out below.

What is claimed is:

1. An isolated antisense molecule complementary to SEQ ID NO: 2 or 3, or wherein said antisense molecule is the complement of the oligonucleotide of SEQ ID NO: 13, 15, 17, 29, 31, 33, 37, 39, 41, 43, 45, 47, 49, 51 or 53, wherein said antisense molecule modulates iron transport across a cell membrane.

2. The isolated antisense molecule of claim 1, wherein said antisense molecule is an RNA.

3. A method for inhibiting hemojuvelin activity in a cell, comprising contacting a cell with an isolated antisense molecule of claim 1, wherein said antisense molecule inhibits hemojuvelin activity in said cell.

4. The method of claim 3, wherein said antisense molecule is the complement of the oligonucleotide of SEQ ID NO: 13, 15, 17, 29, 31, 33, 37, 39, 41, 43, 45, 47, 49, 51 or 53.

5. The method of claim 3, wherein said antisense molecule is an RNA.

6. The method of claim 3, wherein said cell is a member selected from the group consisting of a macrophage, inflammatory cell, Liver cell, intestinal cell, hematopoietic cell, pancreatic cell, skeletal muscle cell, a cell of the nervous system or a Caco2 cell.

7. The method of claim 6, wherein said cell is a Caco2 cell.

8. The method of claim 6, wherein said cell is a macrophage.

9. The method of claim 6, wherein said cell is a hepatocyte.

10. The method of claim 6, wherein said cell is an intestinal cell.

11. The method of claim 6, wherein said cell is a CHO cell.

12. A method for modulating iron transport across the membrane of a cell, comprising contacting a cell with an isolated antisense molecule of claim 1, wherein said antisense molecule modulates iron transport across said cell.

13. The method of claim 12, wherein said antisense molecule is the complement of the oligonucleotide of SEQ ID NO: 13, 15, 17, 29, 31, 33, 37, 39, 41, 43, 45, 47, 49, 51 or 53.

14. The method of claim 6, wherein said antisense molecule is an RNA.

15. The method of claim 12, wherein said modulation of iron transport across a cell membrane results in release of iron by said cell.

16. The method of claim 12, wherein said modulation of iron transport across a cell membrane results in iron uptake by said cell.

17. The method of claim 12, wherein said cell is a member selected from the group consisting of a macrophage, inflammatory cell, Liver cell, intestinal cell, hematopoietic cell, pancreatic cell, skeletal muscle cell, a cell of the nervous system or a Caco2 cell.

18. The method of claim 17, wherein said cell is a Caco2 cell.

19. The method of claim 17, wherein said cell is a macrophage.

20. The method of claim 17, wherein said cell is a hepatocyte.

21. The method of claim 17, wherein said cell is an intestinal cell.

22. The method of claim 17, wherein said cell is a CHO cell.

23. A method for inhibiting hepcidin production in a cell, comprising contacting a cell with an isolated antisense molecule of claim 1, wherein said antisense molecule inhibits hepcidin production in said cell.

24. The method of claim 23, wherein said antisense molecule is the complement of the oligonucleotide of SEQ ID NO: 13, 15, 17, 29, 31, 33, 37, 39, 41, 43, 45, 47, 49, 51 or 53.

25. The method of claim 23, wherein said antisense molecule is an RNA.

26. The method of claim 23, wherein said cell is a member selected from the group consisting of a macrophage, inflammatory cell, Liver cell, intestinal cell, hematopoietic cell, pancreatic cell, skeletal muscle cell, a cell of the nervous system or a Caco2 cell.

27. The method of claim 26, wherein said cell is a Caco2 cell.

28. The method of claim 26, wherein said cell is a macrophage.

29. The method of claim 26, wherein said cell is a hepatocyte.

30. The method of claim 26, wherein said cell is an intestinal cell.

31. The method of claim 26, wherein said cell is a CHO cell.

32. The isolated antisense molecule of claim 1, wherein said antisense molecule is complementary to SEQ ID NO: 2 or 3.

33. The isolated antisense molecule of claim 32, wherein said antisense molecule is an RNA.

34. The isolated antisense molecule of claim 1, wherein said antisense molecule is the complement of the oligonucleotide of SEQ ID NO: 13, 15, 17, 29, 31, 33, 37, 39, 41, 43, 45, 47, 49, 51 or 53.

35. The isolated antisense molecule of claim 34, wherein said antisense molecule is an RNA.

* * * * *